United States Patent
Jaroch et al.

(10) Patent No.: US 6,777,409 B2
(45) Date of Patent: Aug. 17, 2004

(54) NONSTEROIDAL ANTIINFLAMMATORY AGENTS

(75) Inventors: Stefan Jaroch, Berlin (DE); Manfred Lehmann, Berlin (DE); Norbert Schmees, Berlin (DE); Bernd Buchmann, Hohen Neuerdorf (DE); Harmur Rehwinkel, Berlin (DE); Peter Droescher, Weimar (DE); Werner Skuballa, Berlin (DE); Konrad Krolikiewicz, Berlin (DE); Hartwig Hennekes, Berlin (DE); Heike Schaecke, Berlin (DE); Arndt Schottelius, Berlin (DE)

(73) Assignee: Schering Aktiengesellschaft Patents, Berlin (DE)

(*) Notice: Subject to any disclaimer, the term of this patent is extended or adjusted under 35 U.S.C. 154(b) by 0 days.

(21) Appl. No.: 09/916,195

(22) Filed: Jul. 27, 2001

(65) Prior Publication Data

US 2002/0077356 A1 Jun. 20, 2002

(30) Foreign Application Priority Data

Jul. 28, 2000 (DE) .......................................... 100 38 639

(51) Int. Cl.$^7$ ..................... A61K 31/536; C07D 265/02
(52) U.S. Cl. ..................... 514/230.5; 514/470; 544/63; 549/307
(58) Field of Search ........................... 544/63; 549/307; 514/230.5, 470

(56) References Cited

U.S. PATENT DOCUMENTS

| 6,245,804 B1 | 6/2001 | Lehmann et al. ............ 514/443 |
| 6,323,199 B1 | * 11/2001 | Lehmann et al. ........ 514/230.5 |
| 6,344,454 B1 | * 2/2002 | Lehmann et al. ........ 514/230.5 |

FOREIGN PATENT DOCUMENTS

| WO | WO 9854159 | 12/1998 |
| WO | WO 0032584 | 6/2000 |

OTHER PUBLICATIONS

Lehmann et al., Chemical Abstracts, vol. 130:52321, 1998.*

* cited by examiner

*Primary Examiner*—Richard L. Raymond
(74) *Attorney, Agent, or Firm*—Millen, White, Zelano, Branigan, P.C.

(57) ABSTRACT

The compound of formula 1

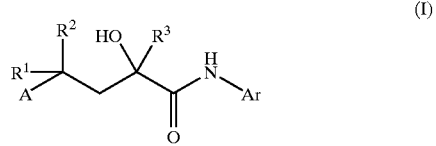

useful in the treatment of inflammation.

48 Claims, No Drawings

NONSTEROIDAL ANTIINFLAMMATORY AGENTS

This invention relates to the use of nonsteroidal compounds for the production of pharmaceutical agents for treatment of inflammations, selected compounds and production processes thereof.

In addition to a large number of steroid compounds, which bind well to the glucocorticoid receptor and have an antiinflammatory action (glucocorticoids), nonsteroidal compounds are known that namely bind to the glucocorticoid receptor, for which to date no antiinflammatory action has been shown, however [cf. Nature Medicin 4 (1998) 92, Mol. Pharmacol. 52 (1997) 571]. In addition, nonsteroidal compounds were described that are derived from steroidal compounds, have an affinity to the glucocorticoid receptor and probably have an antiinflammatory action that is mediated by the receptor [J. Med. Chem. 36, (1993), 3278–3285]. In animal experiments, however, these compounds did not show any advantages relative to steroidal glucocorticoids, i.e., it was not possible to separate the antiinflammatory action from the metabolic effects, e.g., suppression of the suprarenal function.

From WO 98/54159, nonsteroidal compounds are known that have a high gestagenic activity. In the document, there is the observation that the claimed compounds partially also have action on the glucocorticoid and/or mineral corticoid receptor. In this connection, however, there is neither actual mention of compounds nor disclosure of test results. That is to say that from the pool of generically claimed compounds of WO 98/54159, compounds that are not specified in more detail are known that have both high gestagenic activity and action on the glucocorticoid receptor. In terms of industrial applicability, however, compounds that have a selectivity with respect to the above-mentioned actions are advantageous.

In turn, from WO 00/32584, phenol derivatives that have a dissociation of action between antiinflammatory action and undesirable metabolic side effects are known as nonsteroidal antiinflammatory agents.

The compounds that are disclosed in the prior art are still in need of improvement with respect to their dissociation of action between antiinflammatory action and the undesirable side effects.

The object was therefore to make available new nonsteroidal antiinflammatory agents that show a dissociation of action that is at least as good or better than the compounds of the prior art.

Nonsteroidal compounds have now been found that bind well to the glucocorticoid receptor and, mediated by this bond, produce an antiinflammatory action. In the experiment, these compounds show a significantly better or at least equally good dissociation of action between antiinflammatory and undesirable actions and are superior to the previously described nonsteroidal glucocorticoids or have at least just as good an action.

According to this invention, the following compounds of general formula I that have an antiinflammatory action are suitable for use for the production of pharmaceutical agents:

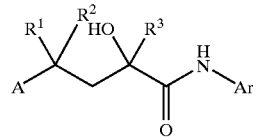

in which $R^1$ and $R^2$ are the same or different and stand for a hydrogen atom, a $C_1$–$C_5$ alkyl group, or, together with the C-atom of the chain, stand for a ring with a total of 3–7 links, $R^3$ stands for a straight-chain or branched $C_1$–$C_5$ alkyl group or a straight-chain or branched, partially or completely fluorinated $C_1$–$C_5$ alkyl group, A stands for the group

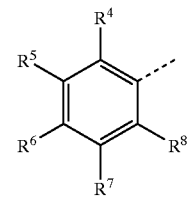

(the dashed line means the interface site), in which $R^4$ to $R^8$ are the same or different from one another and mean a hydrogen atom, a halogen atom, a cyano group, a nitro group, a $COOR^9$ group whereby $R^9$ stands for a hydrogen atom, a straight-chain or branched $C_1$–$C_5$ alkyl group or a benzyl group, a $CONR^{10}$ group, whereby $R^{10}$ stands for a hydrogen atom or a straight-chain or branched $C_1$–$C_5$ alkyl group, an $NHR^{11}$ group, whereby $R^{11}$ stands for a hydrogen atom, a straight-chain or branched $C_1$–$C_5$ alkyl group, a straight-chain or branched, partially or completely fluorinated $C_1$–$C_5$ alkyl group, a $C_1$–$C_5$ acyl group, an —$SO_2$—($C_1$–$C_5$) alkyl group or an —$SO_2$-phenyl group that is optionally substituted by halogen or a $C_1$–$C_5$ alkyl group, a straight-chain or branched $C_1$–$C_5$ alkyl group, a straight-chain or branched $C_2$–$C_5$ alkenyl group, a straight-chain or branched $C_2$–$C_5$ alkinyl group, a straight-chain or branched $C_1$–$C_5$ alkyl group that is partially or completely substituted by fluorine atoms, a $C_1$–$C_5$ acyl group, an aryl radical or a heteroaryl radical, $R^4$ and $R^5$ together with the two carbon atoms of ring A mean a saturated or unsaturated carbocyclic ring with a total of 5–7 links, Ar stands for a ring system, selected from the group of general partial formula 1 or 2,

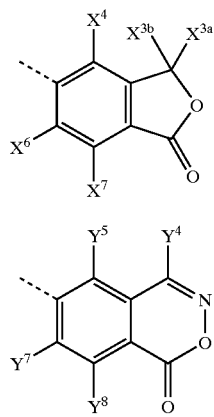

in which
- radicals $X^{3a}$, $X^{3b}$, $X^4$, $X^6$, $X^7$ (in partial formula 1) and $Y^4$, $Y^5$, $Y^7$, and $Y^8$ (in partial formula 2) are the same or different and mean a hydrogen atom, a straight-chain or branched $C_1$–$C_5$ alkyl group, or a straight-chain or branched, partially or completely fluorinated $C_1$–$C_5$ alkyl group,
- radicals $X^4$, $X^6$, $X^7$ (in partial formula 1) or $Y^5$, $Y^7$, $Y^8$ (in partial formula 2) in addition are the same or different and mean a hydrogen atom, a halogen atom, a hydroxy group, a $C_1$–$C_5$ alkoxy group or a $C_1$–$C_5$ alkanoyloxy group, as well as their racemates or separately present stereoisomers, and optionally their physiologically compatible salts.

The compounds of general formula I according to the invention can be present as different stereoisomers because of the presence of asymmetry centers. Both the racemates and the separately present stereoisomers are part of the subject matter of this invention.

A special subject of this invention are the isomers that turn the plane of polarized light in the way that they are referred to as (+)-compounds.

The substituents that are defined as groups or radicals in the compounds of general formula I can have the meanings below in each case.

The $C_1$–$C_5$ alkyl groups $R^1$, $R^2$, $R^3$, $R^4$, $R^5$, $R^{12}$, $X^n$, and $Y^o$ can be straight-chain or branched and can stand for a methyl-, ethyl-, n-propyl-, iso-propyl-, n-butyl, iso-butyl, tert-butyl or n-pentyl, 2,2-dimethylpropyl-, 2-methylbutyl- or 3-methylbutyl group. A methyl group or ethyl group is preferred.

If $R^1$ and $R^2$ together with the C-atom of the chain form a 3- to 7-membered ring, the latter optionally can be substituted by 1–2 oxygen atoms and can be, for example, a cyclopropyl, cyclobutyl, cyclopentyl, cyclohexyl or cycloheptyl ring.

For a partially or completely fluorinated $C_1$–$C_5$ alkyl group, the partially or completely fluorinated alkyl groups that appear above are considered. Of the latter, the trifluoromethyl group or pentafluoroethyl group, as well as partially fluorinated alkyl groups, for example the 5,5,5,4,4-pentafluoropentyl group or 5,5,5,4,4,3,3-heptafluoropentyl group, are preferred. The trifluoromethyl group and the pentafluoroethyl group are preferred.

The substituents of phenyl ring A, independently of one another, can have the meanings that are defined in the claims, such as a hydrogen atom, a halogen atom, a cyano group, a nitro group, an $NHR^{11}$ group, whereby $R^{11}$ stands for a hydrogen atom, a straight-chain or branched $C_1$–$C_5$ alkyl group, a straight-chain or branched, partially or completely fluorinated $C_1$–$C_5$ alkyl group, a $C_1$–$C_5$ acyl group, an —$SO_2$—($C_1$–$C_5$)alkyl group or an —$SO_2$-phenyl group that is optionally substituted by halogen or a $C_1$–$C_5$ alkyl group, a straight-chain or branched $C_1$–$C_5$ alkyl group, a straight-chain or branched $C_2$–$C_5$ alkenyl group, a straight-chain or branched $C_2$–$C_5$ alkinyl group, a straight-chain or branched $C_1$–$C_5$ alkyl group that is partially or completely substituted by fluorine atoms, a $C_1$–$C_5$ acyl group, an aryl radical or a heteroaryl radical.

Preferred are phenyl rings A, which carry 1–3 non-hydrogen substituents.

In addition, $R^4$ and $R^5$ together with the two carbon atoms of ring A can mean a saturated or unsaturated carbocyclic ring with a total of 5 to 7 links, such as, for example, indane, naphthalene, tetrahydronaphthalene, benzocycloheptane.

A subject of the invention is the use of the compounds of general formula I in which $R^4$ to $R^8$ are the same or different from one another and mean a hydrogen atom, a halogen atom, a cyano group, a nitro group, a $COOR^9$ group, whereby $R^9$ stands for a hydrogen atom, a straight-chain or branched $C_1$–$C_5$ alkyl group or a benzyl group, a $CONR^{10}$ group, whereby $R^{10}$ stands for a hydrogen atom or a straight-chain or branched $C_1$–$C_5$ alkyl group, an $NHR^{11}$ group, whereby $R^{11}$ stands for a hydrogen atom, a straight-chain or branched $C_1$–$C_5$ alkyl group, a straight-chain or branched, partially or completely fluorinated $C_1$–$C_5$ alkyl group, a $C_1$–$C_5$ acyl group, a —$SO_2$—($C_1$–$C_5$)alkyl group or an —$SO_2$-phenyl group that is optionally substituted by halogen or a $C_1$–$C_5$ alkyl group, a straight-chain or branched $C_1$–$C_5$ alkyl group, a straight-chain or branched $C_2$–$C_5$ alkenyl group, a straight-chain or branched $C_2$–$C_5$ alkinyl group, a straight-chain or branched $C_1$–$C_5$ alkyl group that is partially or completely substituted by fluorine atoms, a $C_1$–$C_5$ acyl group, an aryl radical or a heteroaryl radical.

The designation halogen atom or halogen means a fluorine, chlorine, bromine or iodine atom. Preferred is a fluorine, chlorine or bromine atom.

For a $C_2$–$C_5$ alkenyl group, for example, a vinyl, 2-substituted vinyl group, 1-propenyl, 2-propenyl, 2- or 3-substituted 2-propenyl group, 1-butenyl, 2-butenyl, 3-butenyl, 1-methyl-2-propenyl, 2-methyl-2-propenyl, 1-pentenyl, 1-methyl-1-butenyl, 2-methyl-1-butenyl, and 3-methyl-1-butenyl group are considered. Preferred are the alkenyl groups, which carry the double bond in 1- or 2-position. As substituents for the vinyl group or the propenyl group, primarily the methyl group or the ethyl group is suitable.

A $C_2$–$C_5$ alkinyl group is defined as, for example, an ethinyl, 1-propinyl, 2-propinyl, 1-butinyl, 2-butinyl, 3-methyl-1-butinyl, 4-methyl-1-butinyl or 1-pentinyl group. Preferred are the alkinyl groups that carry a triple bond in 1-position or 2-position.

With the $C_1$–$C_5$ acyl group, for example, a formyl, acetyl, propionyl, n-butyroyl, 2-methylpropionyl, n-valeroyl, 2-methylbutyroyl, 3-methylbutyroyl or a pivaloyl group is meant.

With a sulfonyl($C_1$–$C_5$) alkyl group $R^{11}$, for example, a methylsulfonyl group or an ethylsulfonyl group is meant.

For the sulfonylphenyl group $R^{11}$ that is optionally substituted by halogen or a $C_1$–$C_5$ alkyl group, 2-chloro (phenylsulfonyl), 3-chloro(phenylsulfonyl), 4-chloro (phenylsulfonyl), 2-methyl(phenylsulfonyl), 3-methyl (phenylsulfonyl), and 4-methyl(phenylsulfonyl) can be mentioned. The sulfonyl group is bonded with its free valency to the nitrogen atom of the $NHR^{11}$ group.

Aryl means a phenyl group or a substituted phenyl group.

As substituents of the aryl group, halogen atoms, the cyano, nitro, $C_1$–$C_5$ alkoxy, amino, hydroxy, carboxy and $C_1$–$C_5$ alkanoyl groups, branched and unbranched $C_1$–$C_5$ alkyl groups, branched and unbranched $C_1$–$C_5$ alkyl groups, which can be partially or completely fluorinated, are suitable.

Heteroaryl comprises aromatic heterocyclic 5- and 6-rings, which can contain in the ring 1–3 additional heteroatoms from the group of oxygen, nitrogen or sulfur. Preferred are heterocyclic five-membered rings. In particular, furyl, thienyl, pyridyl, thiazolyl, oxazolyl, oxadiazolyl, and imidazolyl can be mentioned.

The heteroaryl groups optionally can be substituted by branched and unbranched $C_1$–$C_5$ alkyl groups, branched and unbranched $C_1$–$C_5$ alkyl groups that can be fluorinated and/or halogen atoms.

The hydroxy groups that are possible for radicals $X^n$, $Y^o$ can optionally be defined below as ethers or esters:

As a $C_1$–$C_5$ alkyl group for etherification of hydroxy groups, the above-mentioned alkyl groups are suitable, especially a methyl group or ethyl group.

As a $C_1$–$C_5$ alkanoyl group for esterification of hydroxy groups, a formyl, acetyl, propionyl, butyryl, iso-butyryl, valeryl or iso-valeryl or pivaloyl group is considered, preferably an acetyl group.

As a $C_1$–$C_5$ acyl group for esterification of hydroxy groups, for example, the above-mentioned alkanoyl groups, preferably in turn an acetyl group, or a benzoyl, toluoyl, phenylacetyl, acryloyl, cinnamoyl or cyclohexylcarbonyl group, can be mentioned.

As a $C_1$–$C_5$ alkanoyloxy group for $X^4$, $X^6$, $X^7$, $Y^4$, $Y^5$, $Y^7$ or $Y^8$, a formyloxy, acetoxy, propionyloxy, butyryloxy, iso-butyryloxy, valeryloxy or iso-valeryloxy group is considered, preferably an acetoxy group.

Preferred are compounds in which Ar stands for partial formula 2, and $Y^4$ means a methyl group.

Especially preferred are compounds in which Ar stands for partial formula 2, $Y^4$ means a methyl group, and the other substituents $Y^5$, $Y^7$ and $Y^8$ mean hydrogen.

Nonsteroidal compounds as such with a mixed profile that consists of gestagenic and androgenic activity in different manifestations are already the subject of WO 98/54159. The compounds of general formula I according to claim 1 that are to be used according to this patent application for the production of pharmaceutical agents with antiinflammatory action fall within the scope of the general formula that is contained in WO 98/54159, but are not preferred as a group or directly disclosed as compounds there. They are thus novel and also meet the patenting requirement of inventive activity because of the antiinflammatory action that was found and that is dissociated from undesirable metabolic effects or other effects.

Undesirable actions/effects in the context of this invention are metabolic actions or else bonds to other steroid receptors.

The compounds of general formula I cited by name below fall namely within the scope of the general formula that is cited in WO 98/54159 but are not previously described by name there. They are thus novel and also meet the patenting requirement of inventive activity because of the antiinflammatory action that was found and that is dissociated from undesirable side effects.

These compounds as such therefore also belong to the subject matter of this invention and are listed below.

Their naming is to be illustrated in the following example:

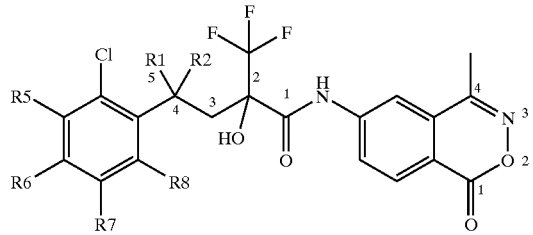

6-[4-(2-Chloro-3-$R^5$-4-$R^6$-5-$R^7$-6-$R^8$-phenyl)-2-hydroxy-4-methyl-2-trifluoromethylvaleroylamino]-4-methyl-2,3-benzoxazin-1-one The following compounds are the subject of this invention:

5-[4-(5-Fluoro-2-methylphenyl)-2-hydroxy-4-methyl-2-trifluoromethylvaleroylamino]-phthalide 6-[4-(2-chloro-5-fluorophenyl)-2-hydroxy-4-methyl-2-trifluoromethylvaleroylamino]-4-methyl-2,3-benzoxazin-1-one 5-[4-(5-fluoro-2-nitrophenyl)-2-hydroxy-4-methyl-2-trifluoromethylvaleroylamino]-phthalide 6-[4-(5-fluoro-2-nitrophenyl)-2-hydroxy-4-methyl-2-trifluoromethylvaleroylamino]-4-methyl-2,3-benzoxazin-1-one 5-[4-(3-fluoro-4-nitrophenyl)-2-hydroxy-4-methyl-2-trifluoromethylvaleroylamino]-phthalide 6-[4-(3-fluoro-4-nitrophenyl)-2-hydroxy-4-methyl-2-trifluoromethylvaleroylamino]-4-methyl-2,3-benzoxazin-1-one 6-[4-(2-bromo-5-fluorophenyl)-2-hydroxy-4-methyl-2-trifluoromethylvaleroylamino]-4-methyl-2,3-benzoxazin-1-one 6-[4-(indan-4'-yl)-2-hydroxy-4-methyl-2-trifluoromethylvaleroylamino]-4-methyl-2,3-benzoxazin-1-one (−) 6-[4-(indan-4'-yl)-2-hydroxy-4-methyl-2-trifluoromethylvaleroylamino]-4-methyl-2,3-benzoxazin-1-one (+) 6-[4-(indan-4'-yl)-2-hydroxy-4-methyl-2-trifluoromethylvaleroylamino]-4-methyl-2,3-benzoxazin-1-one 6-[4-(5-fluoro-2-vinylphenyl)-2-hydroxy-4-methyl-2-trifluoromethylvaleroylamino]-4-methyl-2,3-benzoxazin-1-one (−) 6-[4-(5-fluoro-2-vinylphenyl)-2-hydroxy-4-methyl-2-trifluoromethylvaleroylamino]-4-methyl-2,3-benzoxazin-1-one (+) 6-[4-(5-fluoro-2-vinylphenyl)-2-hydroxy-4-methyl-2-trifluoromethylvaleroylamino]-4-methyl-2,3-benzoxazin-1-one 6-[2-hydroxy-4-methyl-2-trifluoromethyl-4-(4-trifluoromethyphenyl)-valeroylamino]-4-methyl-2,3-benzoxazin-1-one (−) 6-[2-hydroxy-4-methyl-2-trifluoromethyl-4-(4-trifluoromethylphenyl)-valeroylamino]-4-methyl-2,3-benzoxazin-1-one (+) 6-[2-hydroxy-4-methyl-2-trifluoromethyl-4-(4-trifluoromethylphenyl)-valeroylamino]-4-methyl-2,3-benzoxazin-1-one 6-[4-(2-bromo-3,5-difluorophenyl)-2-hydroxy-4-methyl-2-trifluoromethylvaleroylamino]-4-methyl-2,3-benzoxazin-1-one (−) 6-[4-(2-bromo-3,5-difluorophenyl)-2-hydroxy-4-methyl-2-trifluoromethylvaleroylamino]-4-methyl-2,3-benzoxazin-1-one (+) 6-[4-(2-bromo-3,5-difluorophenyl)-2-hydroxy-4-methyl-2-trifluoromethylvaleroylamino]-4-methyl-2,3-benzoxazin-1-one 6-[4-(3,5-difluorophenyl)-2-hydroxy-4-methyl-2-trifluoromethylvaleroylamino]-4-methyl-2,3-benzoxazin-1-one (−) 6-[4-(3,5-difluorophenyl)-2-hydroxy-4-methyl-2-trifluoromethylvaleroylamino]-4-methyl-2,3-benzoxazin-1-one (+) 6-[4-(3,5-difluorophenyl)-2-hydroxy-4-methyl-2-trifluoromethylvaleroylamino]-4-methyl-2,3-benzoxazin-1-one 6-[4-(2-cyano-5-fluorophenyl)-2-hydroxy-4-methyl-2-trifluoromethylvaleroylamino]-4-methyl-2,3-benzoxazin-1-one 6-[4-(2-ethenyl-5-fluorophenyl)-2-hydroxy-4-methyl-2-trifluoromethylvaleroylamino]-4-methyl-2,3-benzoxazin-1-one 6-[4-(2-ethyl-5-fluorophenyl)-2-hydroxy-4-methyl-2-trifluoromethylvaleroylamino]-4-methyl-2,3-benzoxazin-1-one 6-[4-(5-fluoro-2-phenylphenyl-2-hydroxy-4-methy-2-trifluoromethylvaleroylamino]-4-methyl-2,3-benzoxazin-1-one 6-[4-{5-fluoro-2-(furan-2'-yl)phenyl}-2-hydroxy-4-methyl-2-trifluoromethylvaleroylamino]-4-methyl-2,3-benzoxazin-1-one 6-[4-(2-bromo-3,5-difluorophenyl)-2-hydroxy-4-methyl-2-trifluoromethylvaleroylamino]-4-methyl-2,3-benzoxazin-1-one 6-[2-hydroxy-4-methyl-2-trifluoromethyl-4-(1-naphthyl)-valeroylamino]-4-methyl-2,3-benzoxazin-1-one (−) 6-[2-hydroxy-4-methyl-2-trifluoromethyl-4-(1-naphthyl)-valeroylamino]-4-methyl-2,3-benzoxazin-1-one (+) 6-[2-hydroxy-4-methyl-2-trifluoromethyl-4-(1-naphthyl)-valeroylamino]-4-methyl-2,3-benzoxazin-1-one 6-[4-(2-chlorophenyl)-2-hydroxy-4-methyl-2-trifluoromethylvaleroyl]-amino-4-methyl-2,3-benzoxazin-1-one (−)-6-[4-(2-chlorophenyl)-2-hydroxy-4-methyl-2-trifluoromethylvaleroyl]-amino-4-methyl-2,3-benzoxazin-1-one (+)-6-[4-(2-chlorophenyl)-2-hydroxy-4-methyl-2-trifluoromethylvaleroyl]-amino-4-methyl-2,3-benzoxazin-1-one 6-[4-(2-chloro-3-fluoro-phenyl)-2-hydroxy-4-methyl-2-trifluoromethylvaleroyl]-amino-4-methyl-2,3-benzoxazin-1-one (−)-6-[4-(2-chloro-3-fluoro-phenyl)-2-hydroxy-4-methyl-2-trifluoromethylvaleroyl]-amino-4-methyl-2,3-benzoxazin-1-one (+)-6-[4-(2-chloro-3-fluoro-phenyl)-2-hydroxy-4-methyl-2-trifluoromethylvaleroyl]-amino-4-methyl-2,3-benzoxazin-1-one 6-[4-(2-chloro-4-fluoro-phenyl)-2-hydroxy-4-methyl-2-trifluoromethylvaleroyl]-amino-4-methyl-2,3-benzoxazin-1-one (−)-6-[4-(2-chloro-4-fluoro-phenyl)-2-hydroxy-4-methyl-2-trifluoromethylvaleroyl]-amino-4-methyl-2,3-benzoxazin-1-one (+)-6-[4-(2-chloro-4-fluoro-phenyl)-2-hydroxy-4-methyl-2-trifluoromethylvaleroyl]-amino-4-methyl-2,3-benzoxazin-1-one 6-[4-(2-chloro-6-fluoro-phenyl)-2-hydroxy-4-methyl-2-trifluoromethylvaleroyl]-amino-4-methyl-2,3-benzoxazin-1-one (−)-6-[4-(2-chloro-6-fluoro-phenyl)-2-hydroxy-4-methyl-2-trifluoromethylvaleroyl]-amino-4-methyl-2,3-benzoxazin-1-one (+)-6-[4-(2-chloro-6-fluoro-phenyl)-2-hydroxy-4-methyl-2-trifluoromethylvaleroyl]-amino-4-methyl-2,3-benzoxazin-1-one 6-[4-(2,3-dichlorophenyl)-2-hydroxy-4-methyl-2-trifluoromethylvaleroyl]-amino-4-methyl-2,3-benzoxazin-1-one (−)-6-[4-(2,3-dichlorophenyl)-2-hydroxy-4-methyl-2-trifluoromethylvaleroyl]-amino-4-methyl-2,3-benzoxazin-1-one (+)-6-[4-(2,3-dichlorophenyl)-2-hydroxy-4-methyl-2-trifluoromethylvaleroyl]-amino-4-methyl-2,3-benzoxazin-1-one 6-[4-(2,4-dichlorophenyl)-2-hydroxy-4-methyl-2-trifluoromethylvaleroyl]-amino-4-methyl-2,3-benzoxazin-1-one (−)-6-[4-(2,4-dichlorophenyl)-2-hydroxy-4-methyl-2-trifluoromethylvaleroyl]-amino-4-methyl-2,3-benzoxazin-1-one (+)-6-[4-(2,4-dichlorophenyl)-2-hydroxy-4-methyl-2-trifluoromethylvaleroyl]-amino-4-methyl-2,3-benzoxazin-1-one 6-[4-(2,5-dichlorophenyl)-2-hydroxy-4-methyl-2-trifluoromethylvaleroyl]-amino-4-methyl-2,3-benzoxazin-1-one (−)-6-[4-(2,5-dichlorophenyl)-2-hydroxy-4-methyl-2-trifluoromethylvaleroy]-amino-4-methyl-2,3-benzoxazin-1-one (+)-6-[4-(2,5-dichlorophenyl)-2-hydroxy-4-methyl-2-trifluoromethylvaleroyl]-amino-4-methyl-2,3-benzoxazin-1-one 6-[4-(4-bromo-2-chlorophenyl)-2-hydroxy-4-methyl-2-trifluoromethylvaleroy]-amino-4-methyl-2,3-benzoxazin-1-one (−)-6-[4-(4-bromo-2-chlorophenyl)-2-hydroxy-4-methyl-2-trifluoromethylvaleroyl]-amino-4-methyl-2,3-benzoxazin-1-one (+)-6-[4-(4-bromo-2-chlorophenyl)-2-hydroxy-4-methyl-2-trifluoromethylvaleroyl]-amino-4-methyl-2,3-benzoxazin-1-one 6-[4-(2-chloro-3-methoxyphenyl)-2-hydroxy-4-methyl-2-trifluoromethylvaleroyl]-amino-4-methyl-2,3-benzoxazin-1-one (−)-6-[4-(2-chloro-3-methoxyphenyl)-2-hydroxy-4-methyl-2-trifluoromethylvaleroyl]-amino-4-methyl-2,3-benzoxazin-1-one (+)-6-[4-(2-chloro-3-methoxyphenyl)-2-hydroxy-4-methyl-2-trifluoromethylvaleroyl]-amino-4-methyl-2,3-benzoxazin-1-one 6-[4-(2-chloro-3-hydroxyphenyl)-2-hydroxy-4-methyl-2-trifluoromethylvaleroyl]-amino-4-methyl-2,3-benzoxazin-1-one (−)-6-[4-(2-chloro-3-hydroxyphenyl)-2-hydroxy-4-methyl-2-trifluoromethylvaleroyl]-amino-4-methyl-2,3-benzoxazin-1-one (+)-6-[4-(2-chloro-3-hydroxyphenyl)-2-hydroxy-4-methyl-2-trifluoromethylvaleroyl]-amino-4-methyl-2,3-benzoxazin-1-one 6-[4-(2-fluorophenyl)-2-hydroxy-4-methyl-2-trifluoromethylvaleroylamino]-4-methyl-2,3-benzoxazin-1-one (−)-6-[4-(2-fluorophenyl)-2-hydroxy-4-methyl-2-trifluoromethylvaleroylamino]-4-methyl-2,3-benzoxazin-1-one (+)-6-[4-(2-fluorophenyl)-2-hydroxy-4-methyl-2-trifluoromethylvaleroylamino]-4-methyl-2,3-benzoxazin-1-one 6-[4-(2,3-difluorophenyl)-2-hydroxy-4-methyl-2-trifluoromethylvaleroylamino]-4-methyl-2,3-benzoxazin-1-one (−)-6-[4-(2,3-difluorophenyl)-2-hydroxy-4-methyl-2-trifluoromethylvaleroylamino]-4-methyl-2,3-benzoxazin-1-one (+)-6-[4-(2,3-difluorophenyl)-2-hydroxy-4-methyl-2-trifluoromethylvaleroylamino]-4-methyl-2,3-benzoxazin-1-one (−)-6-[4-(2,3-difluorophenyl)-2-hydroxy-4-methyl-2-trifluoromethylhexanoylamino]-4-methyl-2,3-benzoxazin-1-one (+)-6-[4-(2,3-difluorophenyl)-2-hydroxy-4-methyl-2-trifluoromethylhexanoylamino]-4-methyl-2,3-benzoxazin-1-one 6-[4-(2,4-difluorophenyl)-2-hydroxy-4-methyl-2-trifluoromethylvaleroylamino]-4-methyl-2,3-benzoxazin-1-one (−)-6-[4-(2,4-difluorophenyl)-2-hydroxy-4-methyl-2-trifluoromethylvaleroylamino]-4-methyl-2,3-benzoxazin-1-one (+)-6-[4-(2,4-difluorophenyl)-2-hydroxy-4-methyl-2-trifluoromethylvaleroylamino]-4-methyl-2,3-benzoxazin-1-one 6-[4-(2,5-difluorophenyl)-2-hydroxy-4-methyl-2-trifluoromethylvaleroylamino]-4-methyl-2,3-benzoxazin-1-one (−)-6-[4-(2,5-difluorophenyl)-2-hydroxy-4-methyl-2-trifluoromethylvaleroylamino]-4-methyl-2,3-benzoxazin-1-one (+)-6-[4-(2,5-difluorophenyl)-2-hydroxy-4-methyl-2-trifluoromethylvaleroylamino]-4-methyl-2,3-benzoxazin-1-one 6-[4-(2,6-difluorophenyl)-2-hydroxy-4-methyl-2-trifluoromethylvaleroylamino]-4-methyl-2,3-benzoxazin-1-one (−)-6-[4-(2,6-difluorophenyl)-2-hydroxy-4-methyl-2-trifluoromethylvaleroylamino]-4-methyl-2,3-benzoxazin-1-one (+)-6-[4-(2,6-difluorophenyl)-2-hydroxy-4-methyl-2-trifluoromethylvaleroylamino]-4-methyl-2,3-benzoxazin-1-one 6-[4-(2,3,5-trifluorophenyl)-2-hydroxy-4-methyl-2-trifluoromethylvaleroylamino]-4-methyl-2,3-benzoxazin-1-one (−)-6-[4-(2,3,5-trifluorophenyl)-2-hydroxy-4-methyl-2-trifluoromethylvaleroylamino]-4-methyl-2,3-benzoxazin-1-one (+)-6-[4-(2,3,5-trifluorophenyl)-2-hydroxy-4-methyl-2-trifluoromethylvaleroylamino]-4-methyl-2,3-benzoxazin-1-one 6-[4-(2,3,4-trifluorophenyl)-2-hydroxy-4-methyl-2-trifluoromethylvaleroylamino]-4-methyl-2,3-benzoxazin-1-one (−)-6-[4-(2,3,4-trifluorophenyl)-2-hydroxy-4-methyl-2-trifluoromethylvaleroylamino]-4-methyl-2,3-benzoxazin-1-one (+)-6-[4-(2,3,4-trifluorophenyl)-2-hydroxy-4-methyl-2-trifluoromethylvaleroylamino]-4-methyl-2,3-benzoxazin-1-one 6-[4-(3-chloro-2-fluorophenyl)-2-hydroxy-4-methyl-2-trifluoromethylvaleroylamino]-4-methyl-2,3-benzoxazin-1-one (−)-6-[4-(3-chloro-2-fluorophenyl)-2-hydroxy-4-methyl-2-trifluoromethylvaleroyl-amino]-4-methyl-2,3-benzoxazin-1-one (+)-6-[4-(3-chloro-2-fluorophenyl)-2-hydroxy-4-methyl-2-trifluoromethylvaleroylamino]-4-methyl-2,3-benzoxazin-1-one 6-[4-(4-chloro-2-fluorophenyl)-2-hydroxy-4-methyl-2-trifluoromethylvaleroylamino]-4-methyl-2,3-benzoxazin-1-one (−)-6-[4-(4-chloro-2-fluorophenyl)-2-hydroxy-4-methyl-2-trifluoromethylvaleroyl-amino]-4-methyl-2,3-benzoxazin-1-one (+)-6-[4-(4-chloro-2-fluorophenyl)-2-hydroxy-4-methyl-2-trifluoromethylvaleroyl-amino]-4-methyl-2,3-benzoxazin-1-one 6-[4-(2-fluoro-3-methoxyphenyl)-2-hydroxy-4-methyl-2-trifluoromethylvaleroylamino]-4-methyl-2,3-benzoxazin-1-one (−) 6-[4-(2-fluoro-3-methoxyphenyl)-2-hydroxy-4-methyl-2-trifluoromethylvaleroyl-amino]-4-methyl-2,3-benzoxazin-1-one (+) 6-[4-(2-fluoro-3-methoxyphenyl)-2-hydroxy-4-methyl-2-trifluoromethylvaleroylamino]-4-methyl-2,3-benzoxazin-1-one 6-[4-(2-bromophenyl)-2-hydroxy-4-methyl-2-trifluoromethylvaleroylamino]-4-methyl-2,3-benzoxazin-1-one (−)-6-[4-(2-bromophenyl)-2-hydroxy-4-methyl-2-trifluoromethylvaleroylamino]-4-methyl-2,3-benzoxazin-1-one (+)-6-[4-(2-bromophenyl)-2-hydroxy-4-methyl-2-trifluoromethylvaleroylamino]-4-methyl-2,3-benzoxazin-1-one 6-[4-(2-trifluoromethyl-phenyl)-2-hydroxy-4-methyl-2-trifluoromethylvaleroyl]-amino-4-methyl-2,3-benzoxazin-1-one (−)-6-[4-(2-trifluoromethyl-phenyl)-2-hydroxy-4-methyl-2-trifluoromethylvaleroyl]-amino-4-methyl-2,3-benzoxazin-1-one (+)-6-[4-(2-trifluoromethyl-phenyl)-2-hydroxy-4-methyl-2-trifluoromethylvaleroyl]-amino-4-methyl-2,3-benzoxazin-1-one 6-[4-(4-fluoro-2-trifluoromethyl-phenyl)-2-hydroxy-4-methyl-2-trifluoromethyl-valeroyl]-amino-4-methyl-2,3-benzoxazin-1-one (−)-6-[4-(4-fluoro-2-trifluoromethyl-phenyl)-2-hydroxy-4-methyl-2-trifluoromethyl-valeroyl]-amino-4-methyl-2,3-benzoxazin-1-one (+)-6-[4-(4-fluoro-2-trifluoromethyl-phenyl)-2-hydroxy-4-methyl-2-trifluoromethyl-valeroyl]-amino-4-methyl-2,3-benzoxazin-1-one 6-[4-(5-fluoro-2-trifluoromethyl-phenyl)-2-hydroxy-4-methyl-2-trifluoromethyl-valeroyl]-amino-4-methyl-2,3-benzoxazin-1-one (−)-6-[4-(5-fluoro-2-trifluoromethyl-phenyl)-2-hydroxy-4-methyl-2-trifluoromethyl-valeroyl]-amino-4-methyl-2,3-benzoxazin-1-one (+)-6-[4-(5-fluoro-2-trifluoromethyl-phenyl)-2-hydroxy-4-methyl-2-trifluoromethyl-valeroyl]-amino-4-methyl-2,3-benzoxazin-1-one 6-[4-(5-chloro-2-trifluoromethyl-phenyl)-2-hydroxy-4-methyl-2-trifluoromethyl-valeroyl]-amino-4-methyl-2,3-benzoxazin-1-one (−)-6-[4-(5-chloro-2-trifluoromethyl-phenyl)-2-hydroxy-4-methyl-2-trifluoromethyl-valeroyl]-amino-4-methyl-2,3-benzoxazin-1-one (+)-6-[4-(5-chloro-2-trifluoromethyl-phenyl)-2-hydroxy-4-methyl-2-trifluoromethyl-valeroyl]-amino-4-methyl-2,3-benzoxazin-1-one 6-[3-{1-(2-chlorophenyl)-cyclopropyl}-2-hydroxy-2-trifluoromethylpropionyl]-amino-4-methyl-2,3-benzoxazin-1-one (−) 6-[3-{1-(2-chlorophenyl)-cyclopropyl}-2-hydroxy-2-trifluoromethylpropionyl]-amino-4-methyl-2,3-benzoxazin-1-one (+) 6-[3-{1-(2-chlorophenyl)-cyclopropyl}-2-hydroxy-2-trifluoromethylpropionyl]-amino-4-methyl-2,3-benzoxazin-1-one 6-[3-{1-(2-chlorophenyl)-cyclobutyl}-2-hydroxy-2-trifluoromethylpropionyl]-amino-4-methyl-2,3-benzoxazin-1-one (−)-6-[3-{1-(2-chlorophenyl)-cyclobutyl}-2-hydroxy-2-trifluoromethylpropionyl]-amino-4-methyl-2,3-benzoxazin-1-one (+)-6-[3-{1-(2-chlorophenyl)-cyclobutyl}-2-hydroxy-2-trifluoromethylpropionyl]-amino-4-methy-2,3-benzoxazin-1-one 6-[3-{1-(2-chlorophenyl)-cyclopentyl}-2-hydroxy-2-trifluoromethylpropionyl]-amino-4-methyl-2,3-benzoxazin-1-one (−)-6-[3-{1-(2-chlorophenyl)-cyclopentyl}-2-hydroxy-2-trifluoromethylpropionyl]-amino-4-methyl-2,3-benzoxazin-1-one (+)-6-[3-{1-(2-chlorophenyl)-cyclopentyl}-2-hydroxy-2-trifluoromethylpropionyl]-amino-4-methyl-2,3-benzoxazin-1-one 6-[3-{1-(2-chloro-4-fluorophenyl)-cyclopropyl}-2-hydroxy-2-trifluoromethylpropionyl]-amino-4-methyl-2,3-benzoxazin-1-one (−)-6-[3-{1-(2-chloro-4-fluorophenyl)-cyclopropyl}-2-hydroxy-2-trifluoromethyl-propionyl]-amino-4-methyl-2,3-benzoxazin-1-one (+)-6-[3-{1-(2-chloro-4-fluorophenyl)-cyclopropyl}-2-hydroxy-2-trifluoromethyl-propionyl]-amino-4-methyl-2,3-benzoxazin-1-one 6-[3-{1-(2-chloro-4-fluorophenyl)-cyclobutyl}-2-hydroxy-2-trifluoromethylpropionyl]-amino-4-methyl-2,3-benzoxazin-1-one (−)-6-[3-{1-(2-chloro-4-fluorophenyl)-cyclobutyl}-2-hydroxy-2-trifluoromethyl-propionyl]-amino-4-methyl-2,3-benzoxazin-1-one (+)-6-[3-{1-(2-chloro-4-fluorophenyl)-cyclobutyl}-2-hydroxy-2-trifluoromethyl-propionyl]-amino-4-methyl-2,3-benzoxazin-1-one 6-[3-{1-(2-chloro-5-fluorophenyl)-cyclopropyl}-2-hydroxy-2-trifluoromethylpropionyl]-amino-4-methyl-2,3-benzoxazin-1-one (−)-6-[3-{1-(2-chloro-5-fluorophenyl)-cyclopropyl}-2-hydroxy-2-trifluoromethylpropionyl]-amino-4-methyl-2,3-benzoxazin-1-one (+)-6-[3-{1-(2-chloro-5-fluorophenyl)-cyclopropyl}-2-hydroxy-2-trifluoromethyl-propionyl]-amino-4-methyl-2,3-benzoxazin-1-one 6-[3-{1-(2-chloro-5-fluorophenyl)-cyclobutyl}-2-hydroxy-2-trifluoromethylpropionyl]-amino-4-methyl-2,3-benzoxazin-1-one (−)-6-[3-{1-(2-chloro-5-fluorophenyl)-cyclobutyl}-2-hydroxy-2-trifluoromethyl-propionyl]-amino-4-methyl-2,3-benzoxazin-1-one (+)-6-[3-{1-(2-chloro-5-fluorophenyl)-cyclobutyl}-2-hydroxy-2-trifluoromethyl-propionyl]-amino-4-methyl-2,3-benzoxazin-1-one 6-[3-{1-(2,4-dichlorophenyl)-cyclopropyl}-2-hydroxy-2-trifluoromethylpropionyl]-amino-4-methyl-2,3-benzoxazin-1-one (−)-6-[3-{1-(2,4-dichlorophenyl)-cyclopropyl}-2-hydroxy-2-trifluoromethylpropionyl]-amino-4-methyl-2,3-benzoxazin-1-one (+)-6-[3-{1-(2,4-dichlorophenyl)-cyclopropyl}-2-hydroxy-2-trifluoromethylpropionyl]-amino-4-methyl-2,3-benzoxazin-1-one 6-[3-{1-(2,4-dichlorophenyl)-cyclobutyl}-2-hydroxy-2-trifluoromethylpropionyl]-amino-4-methyl-2,3-benzoxazin-1-one (−)-6-[3-{1-(2,4-dichlorophenyl)-cyclobutyl}-2-hydroxy-2-trifluoromethylpropionyl]-amino-4-methyl-2,3-benzoxazin-1-one (+)-6-[3-{1-(2,4-dichlorophenyl)-cyclobutyl}-2-hydroxy-2-trifluoromethylpropionyl]-amino-4-methyl-2,3-benzoxazin-1-one 6-[3-{1-(2-trifluoromethyl-phenyl)-cyclopropyl}-2-hydroxy-2-trifluoromethylpropionyl]-amino-4-methyl-2,3-benzoxazin-1-one (−)-6-[3-{1-(2-trifluoromethyl-phenyl)-cyclopropyl}-2-hydroxy-2-trifluoromethylpropionyl]-amino-4-methyl-2,3-benzoxazin-1-one (+)-6-[3-{1-(2-trifluoromethyl-phenyl)-cyclopropyl}-2-hydroxy-2-trifluoromethylpropionyl]-amino-4-methyl-2,3-benzoxazin-1-one 6-[3-{1-(2-trifluoromethyl-phenyl)-cyclobutyl}-2-hydroxy-2-trifluoromethylpropionyl]-amino-4-methyl-2,3-benzoxazin-1-one (−)-6-[3-{1-(2-trifluoromethyl-phenyl)-cyclobutyl}-2-hydroxy-2-trifluoromethylpropionyl]-amino-4-methyl-2,3-benzoxazin-1-one (+)-6-[3-{1-(2-trifluoromethyl-phenyl)-cyclobutyl}-2-hydroxy-2-trifluoromethylpropionyl]-amino-4-methyl-2,3-benzoxazin-1-one 6-[3-{1-(2-trifluoromethyl-phenyl)-cyclohexyl}-2-hydroxy-2-trifluoromethylpropionyl]-amino-4-methyl-2,3-benzoxazin-1-one (−) 6-[3-{1-(2-trifluoromethyl-phenyl)-cyclohexyl}-2-hydroxy-2-trifluoromethylpropionyl]-amino-4-methyl-2,3-benzoxazin-1-one (+) 6-[3-{1-(2-trifluoromethyl-phenyl)-cyclohexyl}-2-hydroxy-2-trifluoromethylpropionyl]-amino-4-methyl-2,3-benzoxazin-1-one 6-[3-{1-(5-fluoro-2-trifluoromethyl-phenyl)-cyclopropyl}-2-hydroxy-2-trifluoromethylpropionyl]-amino-4-methyl-2,3-benzoxazin-1-one (−)-6-[3-{1-(5-fluoro-2-trifluoromethyl-phenyl)-cyclopropyl}-2-hydroxy-2-trifluoromethylpropionyl]-amino-4-methyl-2,3-benzoxazin-1-one (+)-6-[3-{1-(5-fluoro-2-trifluoromethyl-phenyl)-cyclopropyl}-2-hydroxy-2-trifluoromethylpropionyl]-amino-4-methyl-2,3-benzoxazin-1-one 6-[3-{1-(5-fluoro-2-trifluoromethyl-phenyl)-cyclobutyl}-2-hydroxy-2-trifluoromethylpropionyl]-amino-4-methyl-2,3-benzoxazin-1-one (−)-6-[3-{1-(5-fluoro-2-trifluoromethyl-phenyl)-cyclobutyl}-2-hydroxy-2-trifluoromethylpropionyl]-amino-4-methyl-2,3-benzoxazin-1-one (+)-6-[3-{1-(5-fluoro-2-trifluoromethyl-phenyl)-cyclobutyl}-2-hydroxy-2-trifluoromethylpropionyl]-amino-4-methyl-2,3-benzoxazin-1-one 6-[3-{1-(2-fluorophenyl)-cyclopropyl}-2-hydroxy-2-trifluoromethylpropionylamino]-4-methyl-2,3-benzoxazin-1-one (−)-6-[3-{1-(2-fluorophenyl)-cyclopropyl}-2-hydroxy-2-trifluoromethylpropionylamino]-4-methyl-2,3-benzoxazin-1-one (+)-6-[3-{1-(2-fluorophenyl)-cyclopropyl}-2-hydroxy-2-trifluoromethylpropionylamino]-4-methyl-2,3-benzoxazin-1-one 6-[3-{1-(2-fluorophenyl)-cyclobutyl}-2-hydroxy-2-trifluoromethylpropionylamino]-4-methyl-2,3-benzoxazin-1-one (−)-6-[3-{1-(2-fluorophenyl)-cyclobutyl}-2-hydroxy-2-trifluoromethylpropionylamino]-4-methyl-2,3-benzoxazin-1-one (+)-6-[3-{1-(2-fluorophenyl)-cyclobutyl}-2-hydroxy-2-trifluoromethylpropionylamino]-4-methyl-2,3-benzoxazin-1-one 6-[3-{1-(2-fluorophenyl)-cyclopentyl}-2-hydroxy-2-trifluoromethylpropionylamino]-4-methyl-2,3-benzoxazin-1-one (−)-6-[3-{1-(2-fluorophenyl)-cyclopentyl}-2-hydroxy-2-trifluoromethylpropionylamino]-4-methyl-2,3-benzoxazin-1-one (+)-6-[3-{1-(2-fluorophenyl)-cyclopentyl}-2-hydroxy-2-trifluoromethylpropionylamino]-4-methyl-2,3-benzoxazin-1-one 6-[3-{1-(2-fluorophenyl)-cyclohexyl}-2-hydroxy-2-trifluoromethylpropionylamino]-4-methyl-2,3-benzoxazin-1-one (−)-6-[3-{1-(2-fluorophenyl)-cyclohexyl}-2-hydroxy-2-trifluoromethylpropionylamino]-4-methyl-2,3-benzoxazin-1-one (+)-6-[3-{1-(2-fluorophenyl)-cyclohexyl}-2-hydroxy-2-trifluoromethylpropionylamino]-4-methyl-2,3-benzoxazin-1-one 6-[3-{1-(2,3-difluorophenyl)-cyclopropyl}-2-hydroxy-2-trifluoromethylpropionylamino]-4-methyl-2,3-benzoxazin-1-one (−)-6-[3-{1-(2,3-difluorophenyl)-cyclopropyl}-2-hydroxy-2-trifluoromethylpropionylamino]-4-methyl-2,3-benzoxazin-1-one (+)-6-[3-{1-(2,3-difluorophenyl)-cyclopropyl}-2-hydroxy-2-trifluoromethylpropionyl-amino]-4-methyl-2,3-benzoxazin-1-one 6-[3-{1-(2,3-difluorophenyl)-cyclobutyl}-2-hydroxy-2-trifluoromethylpropionylamino]-4-methyl-2,3-benzoxazin-1-one (−) 6-[3-{1-(2,3-difluorophenyl)-cyclobutyl}-2-hydroxy-2-trifluoromethylpropionylamino]-4-methyl-2,3-benzoxazin-1-one (+) 6-[3-{1-(2,3-difluorophenyl)-cyclobutyl}-2-hydroxy-2-trifluoromethylpropionylamino]-4-methyl-2,3-benzoxazin-1-one 6-[3-{1-(2,5-difluorophenyl)-cyclopropyl}-2-hydroxy-2-trifluoromethylpropionylamino]-4-methyl-2,3-benzoxazin-1-one (−)-6-[3-{1-(2,5-difluorophenyl)-cyanopropyl}-2-hydroxy-2-trifluoromethylpropionylamino]-4-methyl-2,3-benzoxazin-1-one (+)-6-[3-{1-(2,5-difluorophenyl)-cyclopropyl}-2-hydroxy-2-trifluoromethylpropionylamino]-4-methyl-2,3-benzoxazin-1-one 6-[3-{1-(2,3,5-trifluorophenyl)-cyclopropyl}-2-hydroxy-2-trifluoromethylpropionylamino]-4-methyl-2,3-benzoxazin-1-one (−)-6-[3-{1-(2,3,5-trifluorophenyl)-cyclopropyl}-2-hydroxy-2-trifluoromethylpropionylamino]-4-methyl-2,3-benzoxazin-1-one (+)-6-[3-{1-(2,3,5-trifluorophenyl)-cyclopropyl}-2-hydroxy-2-trifluoromethylpropionyl-amino]-4-methyl-2,3-benzoxazin-1-one 6-[3-{1-(2,3,5-trifluorophenyl)-cyclobuty}1-2-hydroxy-2-trifluoromethylpropionylamino]-4-methyl-2,3-benzoxazin-1-one (−)-6-[3-{1-(2,3,5-trifluorophenyl)-cyclobutyl}-2-hydroxy-2-trifluoromethylpropionylamino]-4-methyl-2,3-benzoxazin-1-one (+)-6-[3-{1-(2,3,5-trifluorophenyl)-cyclobutyl}-2-hydroxy-2-trifluoromethylpropionyl-amino]-4-methyl-2,3-benzoxazin-1-one 6-[3-{1-(2-bromophenyl)-cyclopropyl}-2-hydroxy-2-trifluoromethylpropionylamino]-4-methyl-2,3-benzoxazin-1-one (−)-6-[3-{1-(2-bromophenyl)-cyclopropyl}-2-hydroxy-2-trifluoromethylpropionylamino]-4-methyl-2,3-benzoxazin-1-one (+)-6-[3-{1-(2-bromophenyl)-cyclopropyl}-2-hydroxy-2-trifluoromethylpropionylamino]-4-methyl-2,3-benzoxazin-1-one 6-[2-hydroxy-4-methyl-4-(3-methyl-2-nitrophenyl)-2-trifluoromethylvaleroylamino]-4-methyl-2,3-benzoxazin-1-one (−) 6-[2-hydroxy-4-methyl-4-(3-methyl-2-nitrophenyl)-2-trifluoromethylvaleroylamino]-4-methyl-2,3-benzoxazin-1-one (+) 6-[2-hydroxy-4-methyl-4-(3-methyl-2-nitrophenyl)-2-trifluoromethylvaleroylamino]-4-methyl-2,3-benzoxazin-1-one 5-[4-(2-amino-5-fluorophenyl)-2-hydroxy-4-methyl-2-trifluoromethylvaleroyl-amino]-phthalide (−) 5-[4-(2-amino-5-fluorophenyl)-2-hydroxy-4-methyl-2-trifluoromethylvaleroyl-amino]-phthalide (+) 5-[4-(2-amino-5-fluorophenyl)-2-hydroxy-4-methyl-2-trifluoromethylvaleroyl-amino]-phthalide 6-[4-(2-amino-5-fluorophenyl)-2-hydroxy-4-methyl-2-trifluoromethylvaleroyl-amino]-4-methyl-2,3-benzoxazin-1-one (−)-6-[4-(2-amino-5-fluorophenyl)-2-hydroxy-4-methyl-2-trifluoromethylvaleroyl-amino]-4-methyl-2,3-benzoxazin-1-one (+) 6-[4-(2-amino-5-fluorophenyl)-2-hydroxy-4-methyl-2-trifluoromethylvaleroylamino]-4-methyl-2,3-benzoxazin-1-one 6-[4-(2-acetylamino-5-fluorophenyl)-2-hydroxy-4-methyl-2-trifluoromethyl-valeroylamino]-4-methyl-2,3-benzoxazin-1-one (−) 6-[4-(2-acetylamino-5-fluorophenyl)-2-hydroxy-4-methyl-2-trifluoromethyl-valeroylamino]-4-methyl-2,3-benzoxazin-1-one (+) 6-[4-(2-acetylamino-5-fluorophenyl)-2-hydroxy-4-methyl-2-trifluoromethyl-valeroylamino]-4-methyl-2,3-benzoxazin-1-one 5-[4-(2-acetylamino-5-fluorophenyl)-2-hydroxy-4-methyl-2-trifluoromethyl-valeroylamino]-phthalide (−) 5-[4-(2-acetylamino-5-fluorophenyl)-2-hydroxy-4-methyl-2-trifluoromethyl-valeroylamino]-phthalide (+) 5-[4-(2-acetylamino-5-fluorophenyl)-2-hydroxy-4-methyl-2-trifluoromethyl-valeroylamino]-phthalide 5-[4-(5-fluoro-2-mesylaminophenyl)-2-hydroxy-4-methyl-2-trifluoromethyl-valeroylamino]-phthalide (−) 5-[4-(5-fluoro-2-mesylaminophenyl)-2-hydroxy-4-methyl-2-trifluoromethyl-valeroylamino]-phthalide (+) 5-[4-(5-fluoro-2-mesylaminophenyl)-2-hydroxy-4-methyl-2-trifluoromethyl-valeroylamino]-phthalide 6-[4-(2-bromo-3-methoxyphenyl)-2-hydroxy-4-methyl-2-trifluoromethyl-valeroylamino]-4-methyl-2,3-benzoxazin-1-one (−) 6-[4-(2-bromo-3-methoxyphenyl)-2-hydroxy-4-methyl-2-trifluoromethyl-valeroylamino]-4-methyl-2,3-benzoxazin-1-one (+) 6-[4-(2-bromo-3-methoxyphenyl)-2-hydroxy-4-methyl-2-trifluoromethyl-valeroylamino]-4-methyl-2,3-benzoxazin-1-one 6-[4-(2-bromo-3-hydroxyphenyl)-2-hydroxy-4-methyl-2-trifluoromethyl-valeroylamino]-4-methyl-2,3-benzoxazin-1-one (−) 6-[4-(2-bromo-3-hydroxyphenyl)-2-hydroxy-4-methyl-2-trifluoromethyl-valeroylamino]-4-methyl-2,3-benzoxazin-1-one (+) 6-[4-(2-bromo-3-hydroxyphenyl)-2-hydroxy-4-methyl-2-trifluoromethyl-valeroylamino]-4-methyl-2,3-benzoxazin-1-one 6-[4-(2-bromo-3-hydroxyphenyl)-2-hydroxy-4-methyl-2-trifluoromethyl-valeroylamino]-4-methyl-2,3-benzoxazin-1-one (−)-6-[4-(2-bromo-3-hydroxyphenyl)-2-hydroxy-4-methyl-2-trifluoromethyl-valeroylamino]-4-methyl-2,3-benzoxazin-1-one (+)-6-[4-(2-bromo-3-hydroxyphenyl)-2-hydroxy-4-methyl-2-trifluoromethyl-valeroylamino]-4-methyl-2,3-benzoxazin-1-one 6-[4-(2,3-difluorophenyl)-2-hydroxy-4-methyl-2-trifluoromethylcaproylamino]-4-methyl-2,3-benzoxazin-1-one (−) 6-[4-(2,3-difluorophenyl)-2-hydroxy-4-methyl-2-trifluoromethylcaproylamino]-4-methyl-2,3-benzoxazin-1-one (+) 6-[4-(2,3-difluorophenyl)-2-hydroxy-4-methyl-2-trifluoromethylcaproylamino]-4-methyl-2,3-benzoxazin-1-one 6-[4-(2,6-difluorophenyl)-2-hydroxy-4-methyl-4-trifluoromethylcaproylamino]-4-methyl-2,3-benzoxazin-1-one (−) 6-[4-(2,6-difluorophenyl)-2-hydroxy-4-methyl-4-trifluoromethylcaproylamino]-4-methyl-2,3-benzoxazin-1-one (+) 6-[4-(2,6-difluorophenyl)-2-hydroxy-4-methyl-4-trifluoromethylcaproylamino]-4-methyl-2,3-benzoxazin-1-one 6-{3-[4-(2-chloro-5-fluorophenyl)-tetrahydropyran-4-yl]-2-hydroxy-2-trifluoromethylpropionylamino}-4-methyl-2,3-benzoxazin-1-one (−) 6-{3-[4-(2-chloro-5-fluorophenyl)-tetrahydropyran-4-yl]-2-hydroxy-2-trifluoromethylpropionylamino}-4-methyl-2,3-benzoxazin-1-one (+) 6-{3-[4-(2-chloro-5-fluorophenyl)-tetrahydropyran-4-yl]-2-hydroxy-2-trifluoromethylpropionylamino}-4-methyl-2,3-benzoxazin-1-one A special aspect of this invention are the above-indicated 2,3-benzoxazin-1-ones.

Another aspect of this invention are the above-indicated compounds, whose 2,3-benzoxazin-1-one in 3-position carries a methyl group.

If the compounds of general formula I are present as salts, this can be, for example, in the form of hydrochloride, sulfate, nitrate, phosphate, pivalate, maleate, fumarate, tartrate, benzoate, mesylate, citrate or succinate.

If the compounds according to the invention are present as racemic mixtures, they can be separated into the pure, optically active forms according to the methods of racemate separation that are familiar to one skilled in the art. For example, the racemic mixtures can be separated into the pure isomers by chromatography on an even optically active carrier material (CHIRALPAK AD$^{(R)}$). It is also possible to esterify the free hydroxy group in a racemic compound of general formula I with an optically active acid and to separate the diastereoisomer esters that are obtained by fractionated crystallization or by chromatography and to saponify the separated esters in each case to form the optically pure isomers. As an optically active acid, for example, mandelic acid, camphorsulfonic acid or tartaric acid can be used.

Process for the Production of the Compounds According to the Invention

The compounds according to the invention can be obtained by the chain C(R$^1$)(R$^2$)—CH$_2$—C(OH)(R$^3$)—B—NH—Ar being built up starting from a commercially available phenyl compound or a phenyl compound that is available according to known methods, whereby radical R$^3$ is introduced in the last step or the ring system of formulas (1) or (2) (=Ar) is introduced with the formation of the amide bond B—NH—Ar.

Compounds that were produced according to one of the processes below and in which A is a substituted aromatic ring, optionally can be substituted selectively at this aromatic radical according to known processes. Examples of this process are the catalytic hydrogenation of multiple bonds, the nitration and the halogenation. Halogen and nitro substitutions offer, moreover, possible further modifications. Thus, for example, aryl bromides can be reacted with boron, tin or zinc reagents under palladium catalysis in the way that is known to one skilled in the art. Nitro compounds can be reduced to aniline derivatives, for example hydrogenolytically, or with metals, such as, e.g., iron or zinc. The aniline derivatives can be further reacted after diazotization in a known way, for example in terms of Sandmeyer reactions.

(A)

An α-ketocarboxylic acid of general formula II

in which A, $R^1$ and $R^2$ have the meanings that are indicated in formula I,
is either optionally esterified with a compound of general formula $$(R^{12})_3SiR^3 \qquad (III)$$

in which $R^3$ has the meaning that is indicated in general formula I, and $R^{12}$ means a $C_1$–$C_5$ alkyl group,
in the presence of a catalyst, or is reacted with an alkyl metal compound, for example a Grignard reagent or a lithium alkyl, to form a compound of formula IV

As catalyst, fluoride salts or basic compounds, such as alkali carbonates, are suitable (J. Am. Chem. Soc. 111, 393 (1989)).

The ester is optionally cleaved again and then reacted with a compound of general formula V $$Ar—NH—R^{13} \qquad , (V)$$

whereby $R^{13}$ means a hydrogen atom or a $C_1$–$C_5$ acyl group, and Ar has the meaning that is indicated in general formula I,
whereby then radical $R^{13}$ is cleaved off to obtain a compound of formula I or is reacted directly with a compound of general formula $$Ar—NH—R^{13} \qquad (V)$$

whereby $R^{13}$ means a hydrogen atom or a $C_1$–$C_5$ acyl group, and Ar has the meaning that is indicated in general formula I, optionally after activation of the acid function by, e.g., conversion into the acid chloride, whereby then radical $R^{13}$ is cleaved off in any sequence and is reacted with a compound of general formula III $$(R^{12})_3—SiR^3 \qquad (III)$$

in which $R^3$ and $R^{12}$ have the above-indicated meanings, to obtain a compound of formula I.

(B)

A compound of general formula VI

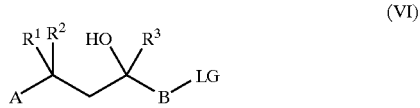

in which A, B, $R^1$, $R^2$, and $R^3$ have the meaning that is indicated in formula I and LG means any leaving group, is reacted with a compound of general formula V $$Ar—NH—R^{13} \qquad (V)$$

whereby $R^{13}$ means a hydrogen atom or a $C_1$–$C_5$ acyl group, and Ar has the meaning that is indicated in general formula I, whereby then radical $R^{13}$ is cleaved off to obtain a compound of formula I.

In this case, the compound of general formula VI can optionally also be formed only as intermediate product, which can be isolated, if desired, or else can be produced only in situ, e.g., this can be an acid chloride that is formed intermediately from a corresponding carboxylic acid. As leaving groups, in this respect, for example, a fluorine, chlorine or bromine atom, or, if no intermediate acid chloride is formed, the mesylate radical or tosylate radical, can be mentioned.

The binding of substances to the glucocorticoid receptor (GR) is examined with the aid of a recombinantly produced receptor. Cytosol preparations of Sf9 cells, which had been infected with recombinant baculoviruses, which code for the GR, are used for the binding studies. In comparison to the reference substance [$^3$H]-dexamethasone, the substances show a high to very high affinity to the GR.

In addition, these compounds in the mineral corticoid receptor (MR)-binding test with use of cytosol preparations that consist of Sf9 cells, which had been infected with baculoviruses that code for the MR, and with use of [$^3$H]-aldosterone as a reference substance, show affinities to the MR.

As an essential molecular mechanism for the antiinflammatory action of glucocorticoids, the GR-mediated inhibition of the transcription of cytokines, adhesion molecules, enzymes and other pro-inflammatory factors can be seen. This inhibition is produced by an interaction of the GR with other transcription factors, e.g., AP-1 and NF-kappa-B (for a survey, see Cato, A. C. B. and Wade, E., BioEssays 18, 371–378, 1996).

The compounds of general formula I according to the invention inhibit the secretion of the cytokine IL-8 that is triggered by lipopolysaccharide (LPS) in human monocyte cell line THP-1. The concentration of the cytokines was determined in the supernatant with use of commercially available ELISA kits.

The antiinflammatory actions of the compounds of general formula I were tested in the animal experiment by testing in the croton oil-induced inflammation in rats and mice (J. Exp. Med. (1995), 182, 99–108). In this connection, croton oil in ethanolic solution was administered topically to the animals' ears. The test substances were also administered topically or systemically simultaneously with or two hours before the croton oil. After 16–24 hours, the ear weight was measured as a yardstick of the inflammatory edema, the peroxidase activity was measured as a yardstick of the invasions of granuloctyes, and the elastase activity was measured as a yardstick of the invasions of neutrophilic granuloctyes. In this test, the compounds of general formula I inhibit the three above-mentioned inflammation parameters both after topical administration and after systemic administration.

One of the most frequent undesirable effects of a glucocorticoid therapy is the so-called "steroid diabetes" [cf. Hatz, H. J., Glucocorticoide: Immunologische Grundlagen, Pharmakologie und Therapierichtlinien [Glucocorticoids: Immunological Bases, Pharmacology and Therapy Guidelines], Wissenschaftliche Verlagsgesellschaft mbH, Stuttgart, 1998]. The reason for this is the stimulation of the gluconeogenesis in the liver by induction of the enzymes that are responsible for this effect and by free amino acids, which develop from the degradation of proteins (catabolic action of glucocorticoids). A key enzyme of the catabolic metabolism in the liver is the tyrosinamino transferase (TAT). The activity of this enzyme can be determined photometrically from liver homogenates and represents a good yardstick of the undesirable metabolic actions of the glucocorticoids. To measure the TAT induction, the animals are sacrificed 8 hours after the test substances are administered, the livers are removed, and the TAT activity in the homogenate is measured. In this test, at doses at which they have an antiinflammatory action, the compounds of general formula I induce little or no tyrosinamino transferase.

In summary, the new compounds of general formula I compared to the previously used steroidal glucocorticoids have the following advantages:

nonsteroidal structure (i.e., the substances are also effective in patients who, because of an allergic reaction to the steroid basic structures of conventional glucocorticoids, can no longer access the latter for therapy (cf. Lutz, M E, el-Azhary R A, Mayo Clin. Proc. 72, 1141–1144, 1997).

good antiinflammatory action with little metabolic action

Because of their antiinflammatory and additional antiallergic, immunosuppressive and antiproliferative actions, the compounds of general formula I according to the invention can be used as medications for treatment or prophylaxis of the following pathologic conditions in mammals and humans: In this case, the term "DISEASE" stands for the following indications:

(i) Lung diseases, which coincide with inflammatory, allergic and/or proliferative processes:
Chronically obstructive lung diseases of any origin, mainly bronchial asthma
bronchitis of different origins
all forms of restrictive lung diseases, mainly allergic alveolitis,
all forms of pulmonary edema, mainly toxic pulmonary edema
sarcoidoses and granulomatoses, especially Boeck's disease (ii) Rheumatic diseases/auto-immune diseases/degenerative joint diseases, which coincide with inflammatory, allergic and/or proliferative processes:
All forms of rheumatic diseases, especially rheumatoid arthritis, acute rheumatic fever, polymyalgia rheumatica,
reactive arthritis
inflammatory soft-tissue diseases of other origins
arthritic symptoms in degenerative joint diseases (arthroses)
traumatic arthritides
collagen diseases of other origins, e.g., systemic lupus erythematodes, scleroderma, polymyositis, dermatomyositis, Sjögren's syndrome, Still syndrome, Felty's syndrome (iii) Allergies, which coincide with inflammatory and/or proliferative processes:
All forms of allergic reactions, e.g., Quincke's edema, hay fever, insect bites, allergic reactions to pharmaceutical agents, blood derivatives, contrast media, etc., anaphylactic shock, urticaria, contact dermatitis (iv) Vascular diseases (vasculitis)
Panarteritis nodosa, temporal arteritis, erythema nodosum (v) Dermatological diseases, which coincide with inflammatory, allergic and/or proliferative processes:
Atopic dermatitis (mainly in children)
psoriasis
pityriasis rubra pilaris
erythematous diseases, triggered by different noxae, e.g., radiation, chemicals, burns, etc.
bullous dermatoses
diseases of the lichenoid group
itching (e.g., of allergic origins)
seborrheal eczema
rosacea
pemphigus vulgaris
erythema exudativum multiforme
balanitis
vulvitis
hair loss, such as alopecia areata
cutaneous T-cell lymphoma (vi) Nephropathies, which coincide with inflammatory, allergic and/or proliferative processes:
Nephrotic syndrome
all nephritides (vii) Liver diseases, which coincide with inflammatory, allergic and/or proliferative processes:
Acute liver cell decomposition
acute hepatitis of different origins, e.g., virally-, toxically- or pharmaceutical agent-induced
chronically aggressive and/or chronically intermittent hepatitis (viii) Gastrointestinal diseases, which coincide with inflammatory, allergic and/or proliferative processes:
Regional enteritis (Crohn's disease)
ulcerative colitis
gastritis
reflux esophagitis
gastroenteritides of other origins, e.g., native sprue (ix) Proctological diseases, which coincide with inflammatory, allergic and/or proliferative processes:
Anal eczema
fissures
hemorrhoids
idiopathic proctitis (x) Eye diseases, which coincide with inflammatory, allergic and/or proliferative processes:
Allergic keratitis, uveitis, iritis
conjunctivitis
blepharitis
optic neuritis
chorioiditis
sympathetic ophthalmia (xi) Diseases of the ear-nose-throat area, which coincide with inflammatory, allergic and/or proliferative processes:
Allergic rhinitis, hay fever
otitis externa e.g., caused by contact dermatitis, infection, etc.
otitis media (xii) Neurological diseases, which coincide with inflammatory, allergic and/or proliferative processes:
Cerebral edema, mainly tumor-induced cerebral edema
multiple sclerosis
acute encephalomyelitis meningitis different forms of convulsions, e.g., infantile nodding spasms (xiii) Blood diseases, which coincide with inflammatory, allergic and/or proliferative processes:

Acquired hemolytic anemia idiopathic thrombocytopenia (xiv) Tumor diseases, which coincide with inflammatory, allergic and/or proliferative processes:

Acute lymphatic leukemia malignant lymphoma lymphogranulomatoses lymphosarcoma extensive metastases, mainly in breast, bronchial and prostate cancers (xv) Endocrine diseases, which coincide with inflammatory, allergic and/or proliferative processes:

Endocrine orbitopathy thyrotoxic crisis de Quervain's thyroiditis

Hashimoto's thyroiditis hyperthyroidism (xvi) Organ and tissue transplants, graft-versus-host disease (xvii) Severe shock conditions, e.g., anaphylactic shock, systemic inflammatory response syndrome (SIRS)

(xviii) Substitution therapy, with:

Innate primary suprarenal insufficiency, e.g., congenital adrenogenital syndrome acquired primary suprarenal insufficiency, e.g., Addison's disease, autoimmune adrenalitis, meta-infective, tumors, metastases, etc.

innate secondary suprarenal insufficiency, e.g., congenital hypopituitarism acquired secondary suprarenal insufficiency, e.g., meta-infective, tumors, etc.

(xix) vomiting, which coincides with inflammatory, allergic and/or proliferative processes:

e.g., in combination with a 5-$HT_3$-antagonist in cytostatic-agent-induced vomiting (xx) Pain with inflammatory origins, e.g., lumbago.

The compounds of general formula I according to the invention can also be used for therapy and prophylaxis of additional pathologic conditions that are not mentioned above, for which synthetic glucocorticoids are now used (see in this connection Hatz, H. J., Glucocorticoide: Immunologische Grundlagen, Pharmakologie und Therapierichtlinien, Wissenschaftliche Verlagsgesellschaft mbH, Stuttgart, 1998).

All previously mentioned indications (i) to (xx) are described in detail in Hatz, H. J., Glucocorticoide: Immunologische Grundlagen, Pharmakologie und Therapierichtlinien, Wissenschaftliche Verlagesgesellschaft mbH, Stuttgart, 1998.

For the therapeutic actions in the above-mentioned pathologic conditions, the suitable dose is different and it depends on, for example, the active strength of the compound of general formula I, the host, the type of administration and the type and severity of the conditions that are to be treated, as well as the use as prophylactic agent or therapeutic agent.

In addition, the invention provides (i) The use of a compound of the invention according to formula I or its mixture for the production of a medication for treating a DISEASE;

(ii) a process for treating a DISEASE, and said process comprises an administration of an amount of compound according to the invention, whereby the amount suppresses the disease and whereby the amount of compound is given to a patient who requires such a medication;

(iii) a pharmaceutical composition for treating a DISEASE, and said treatment comprises one of the compounds according to the invention or its mixture and at least one pharmaceutical adjuvant and/or vehicle.

In general, satisfactory results are to be expected in animals when the daily doses comprise a range of 1 μg to 100,000 μg of the compound according to the invention per kg of body weight. In larger mammals, for example humans, a recommended daily dose lies in the range of 1 μg to 100,000 μg per kg of body weight. Preferred is a dose of 10 to 30,000 μg per kg of body weight, more preferably a dose of 10 to 10,000 μg per kg of body weight. For example, this dose is suitably administered several times daily. For treating acute shock (e.g., anaphylactic shock), individual doses can be given that lie considerably above the above-mentioned doses.

The formulation of the pharmaceutical preparations based on the new compounds is carried out in a way that is known in the art, by the active ingredient being processed with the vehicles, fillers, substances that influence decomposition, binding agents, humectants, lubricants, absorbents, diluents, flavoring correctives, staining agents, etc. that are commonly used in galenicals and converted into the desired form of administration. In this case, reference is to be made to Remington's Pharmaceutical Science, 15th Ed. Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments, both for systemic and for local therapy.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%–20% in these preparations to achieve an adequate pharmacological action.

The invention also comprises the compounds of general formula I according to the invention as therapeutic active ingredients. In addition, the compounds of general formula I according to the invention are part of the invention as therapeutic active ingredients together with pharmaceutically compatible and acceptable adjuvants and vehicles. The invention also comprises a pharmaceutical composition that contains one of the pharmaceutically active compounds according to the invention or mixture thereof and a pharmaceutically compatible salt or pharmaceutically compatible adjuvant and vehicle.

The examples below are used for a more detailed explanation of the invention without intending that it be limited to these examples. The syntheses of important precursors, which are not disclosed within the scope of the experimental part, are already prior art and can be deduced in the example from WO 98/54159.

Experimental Part

EXAMPLE 1

6-[4-(5-Fluoro-2-methylphenyl)-2-hydroxy-4-methyl-2-trifluoromethylvaleroylamino]-4-methyl-2,3-benzoxazin-1-one

EXAMPLE 2

5-[4-(5-Fluoro-2-methylphenyl)-2-hydroxy-4-methyl-2-trifluoromethylvaleroylamino]phthalide Precursors 2-(5-Fluoro-2-methylphenyl)-2-methylpropionitrile 5.25 g of (5-fluoro-2-methylphenyl)acetonitrile and 5.25 ml of methyl iodide are dissolved in 70 ml of dimethylformamide and mixed with 2.7 g of sodium hydride (80%) for 2.5 hours while being cooled with ice. After 3 hours at 0° C. and 16 hours at room temperature, it is mixed with ice water and ethyl acetate, acidified with 1 M hydrochloric acid, and the ethyl acetate phase is washed with water, dried ($Na_2SO_4$) and concentrated by evaporation. 6.1 g of 2-(5-fluoro-2-methylphenyl)-2-methylpropionitrile is obtained as an oil.

2-(5-Fluoro-2-methylphenyl)-2-methylpropionaldehyde 6.1 g of 2-(5-fluoro-2-methylphenyl)-2-methylpropionitrile, dissolved in 60 ml of toluene, is mixed at −70° C. for 45 minutes with 44 ml of 1.2 M diisobutylaluminum hydride solution in toluene. After 4 hours at −78° C., 120 ml of ethyl acetate is added in drops. It is heated to room temperature and washed three times with 2N sulfuric acid and once with water. The ethyl acetate phase is dried ($Na_2SO_4$) and concentrated by evaporation. After distillation, 5.3 g of 2-(5-fluoro-2-methylphenyl)-2-methylpropionaldehyde of boiling point 120° C./0.031 hPa is obtained.

4-(5-Fluoro-2-methylphenyl)-4-methyl-2-oxovaleric acid

A solution of 8.04 ml of 2-diethylphosphono-2-ethoxyacetic acid-ethyl ester in 40 ml of tetrahydrofuran is mixed with 16.5 ml of a 2 M solution of lithium diisopropylamide in tetrahydrofuran-heptane-toluene within 20 minutes while being cooled with ice, and it is stirred for 30 minutes at 0° C. Within 30 minutes, a solution of 5.2 g of 2-(5-fluoro-2-methylphenyl)-2-methylpropionaldehyde in 30 ml of tetrahydrofuran is added in drops to it at 0° C. After 20 hours at room temperature, 2N sulfuric acid is added, it is extracted with ethyl acetate, dried ($Na_2SO_4$) and concentrated by evaporation. The crude product is saponified with 100 ml of 2 M sodium hydroxide solution. 5 g of acid is obtained, which is refluxed for several hours with 450 ml of 2N sulfuric acid while being stirred vigorously. After extraction with ethyl acetate and washing with water, 4 g of 4-(5-fluoro-2-methylphenyl)-4-methyl-2-oxovaleric acid is obtained as a yellowish oil.

5-[4-(5-Fluoro-2-methylphenyl)-4-methyl-2-oxovaleroylamino]-phthalide 950 mg of 4-(5-fluoro-2-methylphenyl)-4-methyl-2-oxovaleric acid in 15 ml of dimethylacetamide is mixed at −10° C. with 0.322 ml of thionyl chloride, stirred for 30 minutes at −10° C. and for 1 hour at 0° C. and purified with 750 mg of 5-aminophthalide. After 16 hours at room temperature, it is mixed with 2 M hydrochloric acid and ethyl acetate, the organic phase is washed neutral with water, dried ($Na_2SO_4$) and concentrated by evaporation. After chromatography on silica gel with hexane-ethyl acetate (3:2) and recrystallization from diisopropyl ether, 486 mg of 5-[4-(5-fluoro-2-methylphenyl)-4-methyl-2-oxovaleroylamino]phthalide of flash point 153° C. is obtained.

6-[4-(5-Fluoro-2-methylphenyl)-4-methyl-2-oxovaleroylamino]-4-methyl-2,3-benzoxazin-1-one was obtained analogously to 5-[4-(5-fluoro-2-methylphenyl)-4-methyl-2-oxovaleroylamino]phthalide with use of 4-(5-fluoro-2-methylphenyl)-4-methyl-2-oxovaleric acid and 6-amino-2,3-benzoxazin-1-one, flash point 186° C.

6-[4-(5-Fluoro-2-methylphenyl)-2-hydroxy-4-methyl-2-trifluoromethylvaleroylamino]-4-methyl-2,3-benzoxazin-1-one

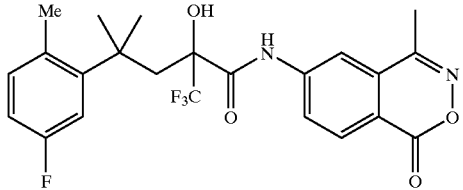

514 mg of 6-[4-(5-fluoro-2-methylphenyl)-4-methyl-2-oxovaleroylamino]-4-methyl-2,3-benzoxazin-1-one in 10 ml of dimethylformamide is purified at 0° C. with 192 mg of cesium carbonate and 0.44 ml of trifluoromethyl (trimethyl)silane. After 1 hour at 0° C. and 16 hours at room temperature, it is again cooled to 0° C. and mixed with 1.3 ml of a 1 M tetrabutylammonium fluoride solution in tetrahydrofuran. After 30 minutes at 0° C., 2N sulfuric acid and ethyl acetate are added, the ethyl acetate phase is washed with water, dried ($Na_2SO_4$) and concentrated by evaporation. After chromatography on silica gel with hexane-ethyl acetate (3:2), 220 mg of 6-[4-(5-fluoro-2-methylphenyl)-2-hydroxy-4-methyl-2-trifluoromethylvaleroylamino]-4-methyl-2,3-benzoxazin-1-one, flash point 175–176° C., is obtained.

5-[4-(5-Fluoro-2-methylphenyl)-2-hydroxy-4-methyl-2-trifluoromethylvaleroylamino]phthalide

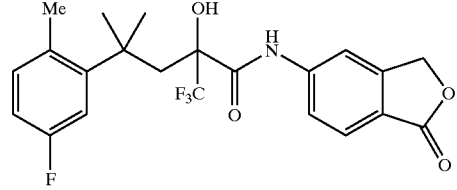

is obtained analogously to Example 1 from 5-[4-(5-fluoro-2-methylphenyl)-4-methyl-2-oxovaleroylamino]phthalide, flash point 165–168° C.

Separation of the Enantiomers from Example 1

The enantiomer mixture of Example 1 is separated by chromatography on chiral support medium (CHIRALPAK AD®, DAICEL Company) with hexane/ethanol (9:1, vv). Thus obtained from 140 mg of racemate are:

(−) 6-[4-(5-Fluoro-2-tolyl)-2-hydroxy-4-methyl-2-trifluoromethylvaleroylamino]-4-methyl-2,3-benzoxazin-1-one as a first fraction: 57 mg, [flash point 203–204° C., $\alpha_D$=−92.70° (c=0.5 in tetrahydrofuran)] and (+) 6-[4-(5-Fluoro-2-tolyl)-2-hydroxy-4-methyl-2-trifluoromethylvaleroylamino]-4-methyl-2,3-benzoxazin-1-one as a second fraction: 56 mg, [flash point 202–203° C.].

EXAMPLE 3

6-[4-(2-Chloro-5-fluorophenyl)-2-hydroxy-4-methyl-2-trifluoromethylvaleroyl-amino]-4-methyl-2,3-benzoxazin-1-one Precursors 2-(2-Chloro-5-fluorophenyl)-2-methylpropionitrile Analogously to the process that is described for 2-(5-fluoro-2-methylphenyl)-2-methyl-propionitrile, 2-(2-chloro-5-fluorophenyl)-2-methylpropionitrile is synthesized, boiling point 100° C./0.04 hPa.

2-(2-Chloro-5-fluorophenyl)-2-methylpropionaldehyde

Analogously to the process that is described for 2-(5-fluoro-2-methylphenyl)-2-methylpropionaldehyde, 2-(2-chloro-5-fluorophenyl)-2-methylpropionaldehyde, boiling point 120° C./0.04 hPa, is obtained.

4-(2-Chloro-5-fluorophenyl)-4-methyl-2-oxovaleric acid

Analogously to the process that is described for 4-(5-fluoro-2-methylphenyl)-4-methyl-2-oxovaleric acid, 4-(2-chloro-5-fluorophenyl)-4-methyl-2-oxovaleric acid is obtained as an oil.

6-[4-(2-Chloro-5-fluorophenyl)-4-methyl-2-oxovaleroylamino]-4-methyl-2,3-benzoxazin-1-one is obtained from 4-(2-chloro-5-fluorophenyl)-4-methyl-2-oxovaleric acid and 6-amino-2,3-benzoxazin-1-one analogously to 5-[4-(5-fluoro-2-methylphenyl)-4-methyl-2-oxovaleroylamino]phthalide, flash point 198–199° C.

6-[4-(2-Chloro-5-fluorophenyl)-2-hydroxy-4-methyl-2-trifluoromethylvaleroylamino]-4-methyl-2,3-benzoxazin-1-one

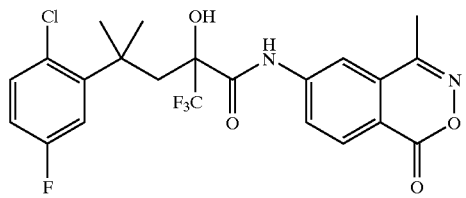

was obtained analogously to Example 1 from 6-[4-(2-chloro-5-fluorophenyl)-4-methyl-2-oxovaleroylamino]-2,3-benzoxazin-1-one, flash point 201–203° C.

Separation of the Enantiomers of Example 3

The enantiomer mixture of Example 3 is separated by chromatography on chiral support medium (CHIRALPAK AD(R), DAICEL Company) with hexane/ethanol (19:1, vv). Thus obtained from 190 mg of racemate are:

(−) 6-[4-(2-Chloro-5-fluorophenyl)-2-hydroxy-4-methyl-2-trifluoromethylvaleroylamino]-4-methyl-2,3-benzoxazin-1-one as a first fraction: 61 mg, [flash point 247–249° C., $\alpha_D = -74.2°$ (c=0.5 in tetrahydrofuran)], and (+)-6-[4-(2-Chloro-5-fluorophenyl)-2-hydroxy-4-methyl-2-trifluoromethylvaleroylamino]-4-methyl-2,3-benzoxazin-1-one as a second fraction: 74 mg, [flash point 247–249° C.].

Analogously to Example 3, the compounds of Tables 1–3 are obtained.

Chlorine Compounds

TABLE 1

| Compound | R5 | R6 | R7 | R8 | R1/R2 | Flash point [° C.] | Isomerism or $[\alpha]_D$ |
|---|---|---|---|---|---|---|---|
| 1 | H | H | H | H | $CH_3$ | 169–171 | racemate |
| 2 | H | H | H | H | $CH_3$ | 198 | −173.3 |
| 3 | H | H | H | H | $CH_3$ | 199 | (+)-form |
| 4 | F | H | H | H | $CH_3$ | 189–192 | racemate |
| 5 | F | H | H | H | $CH_3$ | 189–192 | −89.1 |
| 6 | F | H | H | H | $CH_3$ | 220–223 | +78.2 |
| 7 | H | F | H | H | $CH_3$ | 208–209 | racemate |
| 8 | H | F | H | H | $CH_3$ | 179 | −77.1 |
| 9 | H | F | H | H | $CH_3$ | 181–182 | +74.6 |
| 10 | H | H | H | F | $CH_3$ | 222–224 | racemate |
| 11 | H | H | H | F | $CH_3$ | 232–235 | −110.0 |
| 12 | H | H | H | F | $CH_3$ | 230–233 | +106.0 |
| 13 | Cl | H | H | H | $CH_3$ | 228–230 | racemate |
| 14 | Cl | H | H | H | $CH_3$ | 252–254 | −32.8 |
| 15 | Cl | H | H | H | $CH_3$ | 255–256 | +29.3 |
| 16 | H | Cl | H | H | $CH_3$ | 249–253 | racemate |
| 17 | H | Cl | H | H | $CH_3$ | 253–255 | −126.2 |
| 18 | H | Cl | H | H | $CH_3$ | 252–256 | (+)-form |
| 19 | H | H | Cl | H | $CH_3$ | 210–211 | −96.7 |
| 20 | H | H | Cl | H | $CH_3$ | 208–209 | 100.8 |
| 21 | H | Br | H | H | $CH_3$ | 155–157 | racemate |
| 22 | H | Br | H | H | $CH_3$ | 151–152 | −16.6 |
| 23 | H | Br | H | H | $CH_3$ | 150–155 | (+)-form |
| 24 | OH | H | H | H | $CH_3$ | 235–241 | −75.3 |
| 25 | OH | H | H | H | $CH_3$ | 236–240 | +76.0 |

Fluorine Compounds

TABLE 2

| Compound | R5 | R6 | R7 | R8 | R1/R2 | Flash point [° C.] | Isomerism or $[\alpha]_D$ |
|---|---|---|---|---|---|---|---|
| 26 | H | H | H | H | $CH_3$ | 220 | −85.5 |
| 27 | H | H | H | H | $CH_3$ | 227 | (+)-form |
| 28 | F | H | H | H | $CH_3$ | 204 | racemate |
| 29 | F | H | H | H | $CH_3$ | 204–205 | −90.3 |
| 30 | F | H | H | H | $CH_3$ | 204–205 | +83.0 |
| 31 | H | F | H | H | $CH_3$ | 175–176 | −83.8 |
| 32 | H | F | H | H | $CH_3$ | 176–177 | (+)-form |
| 33 | H | H | F | H | $CH_3$ | 174 | −81.5 |
| 34 | H | H | F | H | $CH_3$ | 174–176 | (+)-form |
| 35 | H | H | H | F | $CH_3$ | 205–210 | racemate |
| 36 | H | H | H | F | $CH_3$ | 230–240 | −71.3 |
| 37 | H | H | H | F | $CH_3$ | 240–245 | (+)-form |
| 38 | F | H | F | H | $CH_3$ | 209 | racemate |
| 39 | Cl | H | H | H | $CH_3$ | 189–192 | −64.0 |
| 40 | Cl | H | H | H | $CH_3$ | 184–187 | (+)-form |

TABLE 2-continued

| Compound | R5 | R6 | R7 | R8 | R1/R2 | Flash point [° C.] | Isomerism or [α]_D |
|---|---|---|---|---|---|---|---|
| 41 | H | Cl | H | H | CH₃ | 239–141 | racemate |
| 42 | H | Cl | H | H | CH₃ | 210–215 | −67.7 |
| 43 | H | Cl | H | H | CH₃ | 198–199 | (+)-form |
| 44 | OCH₃ | H | H | H | CH₃ | 197–200 | racemate |

Bromine Compounds

TABLE 3

| Compound | R5 | R6 | R7 | R8 | R1/R2 | Flash point [° C.] | Isomerism or [α]_D |
|---|---|---|---|---|---|---|---|
| 45 | H | H | H | H | CH₃ | 186–191 | racemate |
| 46 | H | H | H | H | CH₃ | 209–211 | −65.0 |
| 47 | H | H | H | H | CH₃ | 205–207 | +66.0 |

EXAMPLE 4

5-[4-(5-Fluoro-2-nitrophenyl)-2-hydroxy-4-methyl-2-trifluoromethylvaleroyl-amino]phthalide Precursors 2-(3-Fluorophenyl)-2-methylpropionitrile Analogously to the process that is described for 2-(5-fluoro-2-methylphenyl)-2-methylpropionitrile, 2-(3-fluorophenyl)-2-methylpropionitrile is synthesized, boiling point 102–103° C./0.029 hPa.

2-(3-Fluorophenyl)-2-methylpropionaldehyde

Analogously to the process that is described for 2-(5-fluoro-2-methylphenyl)-2-methylpropionaldehyde, 2-(3-fluorophenyl)-2-methylpropionaldehyde, boiling point 120° C./0.04 hPa, is obtained.

4-(3-Fluorophenyl)-4-methyl-2-oxovaleric acid

Analogously to the process that is described for 4-(5-fluoro-2-methylphenyl)-4-methyl-2-oxovaleric acid, 4-(3-fluorophenyl)-4-methyl-2-oxovaleric acid is obtained as an oil.

4-(3-Fluorophenyl)-4-methyl-2-oxovaleric acid-ethyl ester 5.6 g of 4-(3-fluorophenyl)-4-methyl-2-oxovaleric acid and 0.197 ml of sulfuric acid in 150 ml of ethanol are refluxed for 3 hours. The solvent is distilled off. The residue is taken up in ethyl acetate, washed with saturated sodium bicarbonate solution, dried (Na₂SO₄) and concentrated by evaporation. After bulb tube distillation, 5.6 g of 4-(3-fluorophenyl)-4-methyl-2-oxovaleric acid-ethyl ester with a boiling point of 130° C./0.04 hPA is obtained.

4-(3-Fluorophenyl)-2-hydroxy-4-methyl-2-trifluoromethylvaleric acid ethyl ester 5.3 g of 4-(3-fluorophenyl)-4-methyl-2-oxovaleric acid-ethyl ester in 60 ml of dimethylformamide is combined at 0° C. with 3.25 g of cesium carbonate and 4.63 ml of trifluoromethyl(trimethyl)-silane. After 1 hour at 0° C. and 16 hours at room temperature, it is cooled again to 0° C. and mixed with 20 ml of a 1 M tetrabutylammonium fluoride solution in tetrahydrofuran. After 30 minutes at 0° C., 2N sulfuric acid and ethyl acetate are added to it, the ethyl acetate phase is washed with water, dried (Na₂SO₄) and concentrated by evaporation. After chromatography on silica gel hexane-ethyl acetate (20:1) and bulb tube distillation, 4.45 g of 4-(3-fluorophenyl)-2-hydroxy-4-methyl-2-trifluoromethylvaleric acid-ethyl ester is obtained (boiling point 100° C./0.04 hpa).

4-(5-Fluoro-2-nitrophenyl)-2-hydroxy-4-methyl-2-trifluoromethylvaleric acid ethyl ester 4-(3-Fluoro-4-nitrophenyl)-2-hydroxy-4-methyl-2-trifluoromethylvaleric acid ethyl ester 3.3 g of 4-(3-fluorophenyl)-2-hydroxy-4-methyl-2-trifluoromethylvaleric acid ethyl ester is dissolved in 20 ml of trifluoroacetic acid and mixed at 0° C. with 0.84 ml of 100% nitric acid. After 3 hours at 0° C. and 16 hours at room temperature, the batch is poured onto ice, the crystallizate is suctioned off, washed with water and dried. By recrystallization from hexane, 2.5 g of 4-(5-fluoro-2-nitrophenyl)-2-hydroxy-4-methyl-2-trifluoromethylvaleric acid-ethyl ester of flash point 66–67° C. is obtained.

From the mother liquor, after chromatography on silica gel with hexane-ethyl acetate (8:1), another 500 mg of 4-(5-fluoro-2-nitrophenyl)-2-hydroxy-4-methyl-2-trifluoromethylvaleric acid-ethyl ester accumulates as a first fraction, and 800 mg of 4-(3-fluoro-4-nitrophenyl)-2-hydroxy-4-methyl-2-trifluoromethylvaleric acid-ethyl ester as an oil accumulates as a second fraction.

4-(5-Fluoro-2-nitrophenyl)-2-hydroxy-4-methyl-2-trifluoromethylvaleric acid 2.4 g of 4-(5-fluoro-2-nitrophenyl)-2-hydroxy-4-methyl-2-trifluoromethylvaleric acid-ethyl ester is dissolved in 30 ml of ethanol and purified with 60 ml of 1 M sodium hydroxide solution. After 2 days at room temperature, it is concentrated by evaporation, the residue is dissolved in water, acidified at 0° C. and extracted with ethyl acetate. The ethyl acetate phase is washed neutral with water, dried (Na₂SO₄) and concentrated by evaporation. After crystallization from diisopropyl ether, 4-(5-fluoro-2-nitrophenyl)-2-hydroxy-4-methyl-2-trifluoromethylvaleric acid with a flash point of 130–131° C. is obtained.

5-[4-(5-Fluoro-2-nitrophenyl)-2-hydroxy-4-methyl-2-trifluoromethylvaleroylamino]phthalide

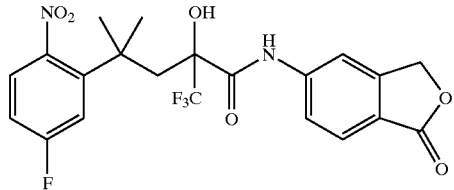

255 mg of 4-(5-fluoro-2-nitrophenyl)-2-hydroxy-4-methyl-2-trifluoromethylvaleric acid in 3 ml of dimethyl acetamide is mixed at 0° C. with 0.105 ml of thionyl chloride, stirred for 30 minutes at 0° C. and 45 minutes at room temperature and combined with 300 mg of 5-aminophthalide. After 16 hours at room temperature, it is mixed with 2 M hydrochloric acid and ethyl acetate, the organic phase is washed neutral with water, dried (Na$_2$SO$_4$) and concentrated by evaporation. After chromatography on silica gel with hexane-ethyl acetate (3:2) and recrystallization from diisopropyl ether, 80 mg of 5-[4-(5-fluoro-2-nitrophenyl)-2-hydroxy-4-methyl-2-trifluoromethylvaleroylamino]phthalide is obtained, flash point 200–201° C.

6-[4-(5-Fluoro-2-nitrophenyl)-2-hydroxy-4-methyl-2-trifluoromethylvaleroylamino]-4-methyl-2,3-benzoxazin-1-one

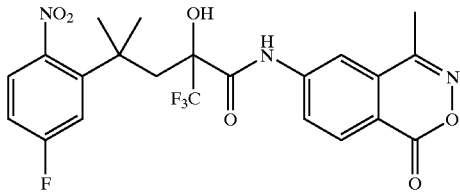

is obtained analogously to Example 4 from 4-(5-fluoro-2-nitrophenyl)-2-hydroxy-4-methyl-2-trifluoromethylvaleric acid and 6-amino-2,3-benzoxazin-1-one, flash point 208–210° C.

EXAMPLE 6

5-[4-(3-Fluoro-4-nitrophenyl)-2-hydroxy-4-methyl-2-trifluoromethylvaleroyl-amino]phthalide
4-(3-Fluoro-4-nitrophenyl)-2-hydroxy-4-methyl-2-trifluoromethylvaleric acid
is obtained from 4-(3-fluoro-4-nitrophenyl)-2-hydroxy-4-methyl-2-trifluoromethylvaleric acid-ethyl ester as an oil as described under Example 4 for 4-(5-fluoro-2-nitrophenyl)-2-hydroxy-4-methyl-2-trifluoromethylvaleric acid.
5-[4-(3-Fluoro-4-nitrophenyl)-2-hydroxy-4-methyl-2-trifluoromethylvaleroyl-amino]phthalide

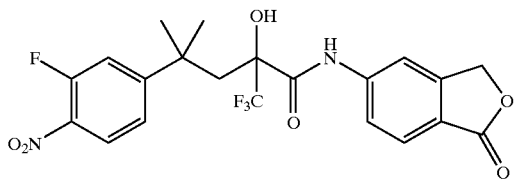

is obtained analogously to Example 4 from 4-(3-fluoro-4-nitrophenyl)-2-hydroxy-4-methyl-2-trifluoromethylvaleric acid and 5-aminophthalide, flash point 188–189° C.

EXAMPLE 7

6-[4-(3-Fluoro-4-nitrophenyl)-2-hydroxy-4-methyl-2-trifluoromethylvaleroylamino]-4-methyl-2,3-benzoxazin-1-one

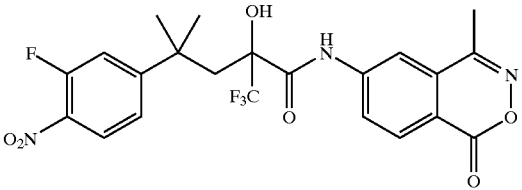

is obtained analogously to Example 4 from 4-(3-fluoro-4-nitrophenyl)-2-hydroxy-4-methyl-2-trifluoromethylvaleric acid and 6-amino-2,3-benzoxazin-1-one, flash point 236–237° C.

EXAMPLE 8

6-[4-(2-Bromo-5-fluorophenyl)-2-hydroxy-4-methyl-2-trifluoromethylvaleroyl-amino]-4-methyl-2,3-benzoxazin-1-one
Precursors
3-Methyl-2-butenoic acid-(4-fluorophenyl)amide
A solution of 10.0 g (0.1 mol) of 3-methyl-2-butenoic acid in 200 ml of THF is mixed with 9.4 ml (0.1 mol) of ethyl chloroformate and 14.1 ml (0.1 mol) of triethylamine at 0° C. After 10 minutes at room temperature, 10.6 ml (0.11 mol) of 4-fluoroaniline is added to it. The batch is stirred for 1 hour at room temperature, diluted with water and extracted with ethyl acetate (1 l). The organic phase is washed with saturated NaCl, dried (Na$_2$SO$_4$) and concentrated by evaporation in a vacuum. The residue is purified by column chromatography on silica gel with hexane-ethyl acetate. Yield 18.8 g.
$^1$H-NMR (CDCl$_3$), δ (ppm)=1.92 (d, 3H), 2.25 (d, 3H), 5.71 (sept, 1H), 7.02 (t, 2H), 7.13 (br., 1H), 7.50 (br., 2H).
3,4-Dihydro-4,4-dimethyl-6-fluoro-2-quinolone
9.4 g (48.7 mmol) of 3-methyl-2-butenoic acid-(4-fluorophenyl)amide is heated to 130–140° C. and mixed in portions with 9.6 g (73.5 mmol) of aluminum trichloride. After the addition is completed, the temperature is kept at 80° C. for 30 more minutes. It is allowed to cool to room temperature and carefully treated with 60 ml of ice water. After 150 ml of chloroform is added, the batch is stirred for 15 minutes, acidified with dilute hydrochloric acid and extracted with chloroform (3×150 ml). The combined organic extracts are washed with saturated NaCl, dried (Na$_2$SO$_4$) and concentrated by evaporation in a vacuum. Column chromatography on silica gel with hexane-ethyl acetate yields 6.0 g.
$^1$H-NMR (CDCl$_3$), δ (ppm)=1.34 (s, 6H), 2.48 (s, 2H), 6.80 (dd, 1H), 6.88 (td, 1H), 7.02 (dd, 1H), 9.02 (br., 1H).
1-tert-Butoxycarbonyl-3,4-dihydro-4,4-dimethyl-6-fluoro-2-quinolone
A solution of 6.0 g (30.9 mmol) of 3,4-dihydro-4,4-dimethyl-6-fluoro-2-quinolone in 200 ml of THF is mixed with 8.8 g (40.2 mmol) of di-tert-butyldicarbonate and 4.9 g (40.2 mmol) of DMAP. After 24 hours at room temperature, it is concentrated by evaporation, and the residue is purified by column chromatography on silica gel with hexane-ethyl acetate. Yield: 9.0 g.
$^1$H-NMR (CDCl$_3$), δ (ppm)=1.34 (s, 6H), 1.61 (s, 9H), 2.50 (s, 2H), 6.91 (m, 2H), 7.03 (dd, 1H).
3-(2-tert-Butoxycarbonylamino-5-fluorophenyl)-3-methyl-1-butanol
375 ml (0.75 mol) of an aqueous 2 M lithium hydroxide solution is added to a solution of 44 g (0.15 mol) of 1-tert-butoxycarbonyl-3,4-dihydro-4,4-dimethyl-6-fluoro-2-quinolone in 1 l of THF. After 24 hours at room temperature, the batch is concentrated by evaporation, brought to pH 4 with 10% citric acid and extracted with ether. The combined organic extracts are washed with saturated NaCl, dried (Na$_2$SO$_4$) and concentrated by evaporation in a vacuum. Column chromatography of the residue on silica gel with hexane-ethyl acetate yields 34.0 g of 3-(2-tert-butoxycarbonylamino-5-fluorophenyl)-3-methylbutyric acid [$^1$H-NMR (CDCl$_3$) δ (ppm)=1.62 (br.s, 15 H), 2.77 (s, 2H), 6.41 (br, 1H), 6.93 (td, 1H), 7.07 (dd, 1H), 7.20 (br, 1H)], which dissolves in 1 l of THF and is mixed at 0° C. with 17 ml (121 mmol) of triethylamine and 11.5 ml (121 mmol) of ethyl chloroformate. After 10 minutes at 0° C., 20.7 g (546 mmol) of sodium borohydride is added to it, and 1 l of MeOH is slowly added in drops to it. The batch is stirred for another 30 minutes at 0° C., concentrated by evaporation and diluted with ethyl acetate. It is washed with saturated NaCl, dried on $Na_2SO_4$ and purified by column chromatography on silica gel with hexane-ethyl acetate. Yield: 6.7 g.

$^1$H-NMR ($CDCl_3$), δ (ppm)=1.40 (s, 6H), 1.51 (s, 9H), 2.06 (t, 2H), 3.49 (q, 2H), 6.32 (br.s, 1H), 6.91 (ddd, 1H), 7.05 (dd, 1H), 7.28 (br., 1H).

2,2-Dimethylpropionic acid-[3-(2-amino-5-fluorophenyl)-3-methyl]butyl ester

A solution of 6.7 g (22.7 mmol) of 3-(2-tert-butoxycarbonylamino-5-fluorophenyl)-3-methyl-1-butanol in 200 ml of pyridine is mixed at 0° C. with 5.6 ml of pivaloyl chloride. After 24 hours at room temperature, water is added to it, and it is stirred for 2 hours at room temperature. The batch is diluted with ethyl acetate, washed with 10% citric acid, water, saturated $NaHCO_3$ and saturated NaCl, dried ($Na_2SO_4$) and concentrated by evaporation in a vacuum. Column chromatography on silica gel with hexane-ethyl acetate yields 9.0 g of 2,2-dimethylpropionic acid-[3-(2-tert-butoxycarbonylamino-5-fluorophenyl)-3-methyl] butyl ester. 6.1 g (16 mmol) of it is dissolved in 100 ml of dichloromethane and mixed with 30 ml of trifluoroacetic acid. After 30 minutes at room temperature, the batch is diluted with ethyl acetate, washed with water, saturated $NaHCO_3$ and saturated NaCl, dried ($Na_2SO_4$) and concentrated by evaporation in a vacuum. Purification by column chromatography on silica gel with hexane-ethyl acetate yields 4.0 g of product.

$^1$H-NMR ($CDCl_3$), δ (ppm)=1.15 (s, 9H), 1.46 (s, 6H), 2.15 (t, 2H), 3.67 (br, 2H), 3.92 (t, 2H), 6.57 (dd, 1H), 6.75 (ddd, 1H), 6.92 (dd, 1H).

2,2-Dimethylpropionic acid-[3-(2-bromo-5-fluorophenyl)-3-methyl]butyl ester

A solution of 1.9 g (8.5 mmol) of copper(II) bromide and 1.4 ml (7.0 mmol) of tert-butyl nitrite in 10 ml of acetonitrile is heated to 65° C. and mixed within 10 minutes with a solution of 2.0 g (7.1 mmol) of 2,2-dimethylpropionic acid-[3-(2-amino-5-fluorophenyl)-3-methyl]butyl ester in 10 ml of acetonitrile. After 5 minutes at 65° C., it is allowed to cool to room temperature, concentrated by evaporation, and the residue is purified by column chromatography on silica gel with hexane-ethyl acetate: Yield 1.6 g.

$^1$H-NMR ($CDCl_3$), δ (ppm)=1.12 (s, 9H), 1.52 (s, 6H), 2.41 (t, 2H), 3.88 (t, 2H), 6.79 (ddd, 1H), 7.12 (dd, 1H), 7.53 (dd, 1H).

3-(2-Bromo-5-fluorophenyl)-3-methylbutanol

At −20° C., a solution of 1.97 g (5.7 mmol) of 2,2-dimethylpropionic acid-[3-(2-bromo-5-fluorophenyl)-3-methyl]butyl ester in 20 ml of toluene is mixed with 11.9 ml (14.3 mmol) of a 1.2 M diisobutylaluminum hydride-toluene solution. After 30 minutes at −20° C., the batch is cooled to −70° C. and mixed with 4 ml of isopropanol and 6 ml of water. After 2 hours at room temperature, the batch is filtered, and the filtrate is concentrated by evaporation in a vacuum. Column chromatography on silica gel with hexane-ethyl acetate yields 1.25 g of product.

$^1$H-NMR ($CDCl_3$), δ (ppm)=1.52 (s, 6H), 2.37 (t, 2H), 3.45 (q, 2H), 6.80 (ddd, 1H), 7.12 (dd, 1H), 7.54 (dd, 1H).

2-[1-Benzoyl-3-(2-bromo-5-fluorophenyl)-3-methylbutyl]furan

A solution of 1.0 g (3.8 mmol) of 3-(2-bromo-5-fluorophenyl)-3-methylbutanol in 24 ml of dichloromethane is treated with 8.5 ml of DMSO, 2.66 ml (19.2 mmol) of triethylamine and 1.23 g (7.7 mmol) of pyridine-sulfur trioxide complex. After 1 hour at room temperature, the batch is mixed with 30 ml of saturated $NH_4Cl$, and after 15 minutes, it is extracted with 400 ml of ether. The extract is washed with saturated NaCl, dried ($Na_2SO_4$) and concentrated by evaporation in a vacuum. The residue (1.1 g) is dissolved in 8 ml of THF and added at −70° C. within 30 minutes to a solution of 2-furyllithium in 38 ml of THF, which is produced from 0.85 ml of furan (11.5 mmol) and 7.7 ml (12.3 mmol) of a 1.6 M nBuLi-hexane solution according to A. Dondoni et al., J. Org. Chem. 1997, 62, 5484. After 1.5 hours at −70° C., the batch is poured into 50 ml of saturated $NH_4Cl$ and extracted with 400 ml of MTBE. The organic phase is dried ($Na_2SO_4$) and concentrated by evaporation in a vacuum. The residue (1.1 g) is dissolved in 40 ml of pyridine and mixed first with 0.9 ml (7.7 mmol) of benzoyl chloride at 0° C. After 2 hours at 0° C. and 2 hours at room temperature, 30 mg of DMAP is added to it, and after another 2 hours at room temperature, a further 0.9 ml (7.7 mmol) of benzoyl chloride. After 18 hours at room temperature, the batch is mixed with 3 ml of water and concentrated by evaporation in a vacuum. The residue is taken up in 400 ml of MTBE, and the resulting solution is washed with 10% citric acid and saturated NaCl, dried ($Na_2SO_4$) and concentrated by evaporation in a vacuum. Column chromatography on silica gel with hexane-ethyl acetate yields 1.46 g of product.

$^1$H-NMR ($CDCl_3$), δ (ppm)=1.52 (s, 3H), 1.58 (s, 3H), 2.53 (dd, 1H), 3.33 (dd, 1H), 6.10 (dd, 1H), 6.26 (m, 2H), 6.49 (ddd, 1H), 6.97 (dd, 1H), 7.34 (m, 4H), 7.48 (m, 1H), 7.81 (m, 2H).

2-Benzoyl-4-(2-bromo-5-fluorophenyl)-4-methylvaleric acid-methyl ester

A suspension of 10.9 g (50.8 mmol) of sodium periodate in 140 ml of water-acetonitrile-tetrachloromethane (4:2:1) is mixed with 45 mg (0.34 mmol) of ruthenium(IV)oxide-hydrate. After 10 minutes, a solution of 2-[1-benzoyl-3-(2-bromo-5-fluorophenyl)-3-methylbutyl]furan in 40 ml of acetonitrile is added to it, it is stirred for another 10 minutes, and the batch is poured into 400 ml of saturated $Na_2SO_3$. A pH of 5 is set with 10% citric acid, and the batch is extracted with ethyl acetate. The combined extracts are dried ($Na_2SO_4$) and concentrated by evaporation in a vacuum. The residue is taken up in 8 ml of DMF and treated with 0.42 ml (6.8 mmol) of methyl iodide and 2.21 g (6.8 mmol) of cesium carbonate. After 5 hours at room temperature, the batch is diluted with 600 ml of MTBE, washed with 10% sulfuric acid and saturated NaCl, dried ($Na_2SO_4$) and concentrated by evaporation in a vacuum. Column chromatography on silica gel with hexane-ethyl acetate yields 0.9 g of product.

$^1$H-NMR ($CDCl_3$), δ (ppm)=1.58 (s, 3H), 1.62 (s, 3H), 2.55 (dd, 1H), 3.10 (dd, 1H), 3.72 (s, 3H), 5.21 (dd, 1H), 6.58 (ddd, 1H), 7.03 (dd, 1H), 7.35–7.47 (m, 3H), 7.55 (m, 1H), 7.83 (m, 2H).

4-(2-Bromo-5-fluorophenyl)-2-hydroxy-4-methylvaleric acid-methyl ester

A solution of 0.9 g (2.13 mmol) of 2-benzoyl-4-(2-bromo-5-fluorophenyl)-4-methylvaleric acid-methyl ester in 50 ml of MeOH is mixed with 1.47 g (10.6 mmol) of potassium carbonate and stirred for 3 hours at room temperature. The batch is acidified (pH 3) with 10% sulfuric acid, and it is extracted with ethyl acetate. The combined extracts are washed with saturated NaCl, dried ($Na_2SO_4$) and concentrated by evaporation in a vacuum. The residue is taken up in 8 ml of DMF and stirred with 1.92 g (5.9 mmol) of cesium carbonate and 0.38 ml (5.9 mmol) of methyl iodide for 3 hours at room temperature. The batch is mixed with 10% citric acid and extracted with MTBE. The organic phase is washed with saturated NaCl, dried ($Na_2SO_4$) and concentrated by evaporation in a vacuum. Column chromatography on silica gel with hexane-ethyl acetate yields 250 mg of product.

¹H-NMR (CDCl₃), δ (ppm)=1.57 (s, 3H), 1.61 (s, 3H), 2.10 (dd, 1H), 2.51 (d, 1H), 2.82 (dd, 1H), 3.74 (s, 3H), 3.96 (ddd, 1H), 6.81 (dd, 1H), 7.22 (dd, 1H), 7.55 (dd, 2H).

6-[4-(2-Bromo-5-fluorophenyl)-4-methyl-2-oxovaleroylamino]-4-methyl-2,3-benzoxazin-1-one 663 mg (1.56 mol) of 1,1,1-triacetoxy-1,1-dihydro-1,2-benziodoxol-3(1H)-one (Dess-Martin-periodinane, cf. D. B. Dess, J. C. Martin, J. Am. Chem. Soc. 1991, 113, 7277) is added to a solution of 250 mg (0.78 mmol) of 4-(2-bromo-5-fluorophenyl)-2-hydroxy-4-methylvaleric acid-methyl ester in 10 ml of dichloromethane. After 1.5 hours at room temperature, the batch is diluted with 150 ml of MTBE, washed with a solution of 1.2 g of NaHCO₃ and 4.0 g of Na₂SO₃ in 50 ml of water, saturated NaHCO₃ and saturated NaCl, dried (Na₂SO₄) and concentrated by evaporation in a vacuum. The residue (250 mg) is taken up in 16 ml of THF-EtOH (1:1) and mixed with 3.9 ml (3.9 mmol) of a 1 M sodium hydroxide solution. After 30 minutes, the batch is concentrated in a vacuum, diluted with 20 ml of water and washed with MTBE. The aqueous phase is acidified with 10% sulfuric acid (pH 2) and extracted with 100 ml of ethyl acetate and 100 ml of dichloromethane. The combined extracts are dried (NaSO₄) and concentrated by evaporation in a vacuum. 0.06 ml (0.92 mmol) of thionyl chloride is added in drops at −6° C. to the solution of the residue (230 mg) in 5 ml of dimethyl acetamide. After 20 minutes at −6° C., 201 mg (1.14 mmol) of 6-amino-4-methyl-2,3-benzoxazin-1-one is added to it. The batch is stirred for 15 hours at room temperature, acidified with 50 ml of 10% citric acid and shaken out with 150 ml of MTBE. The organic phase is washed with saturated NaCl, dried (Na₂SO₄) and concentrated by evaporation in a vacuum. Column chromatography on silica gel with hexane-ethyl acetate yields 290 mg of product.

¹H-NMR ([D₆]-DMSO), δ (ppm)=1.57 (s, 6H), −2.5 (s, 3H; under the DMSO signal), 3.89 (s, 2H), 7.03 (ddd, 1H), 7.34 (dd, 1H), 7.62 (dd, 1H), 8.25 (d, 1H), 8.33 (m, 2H), 11.03 (br., 1H);

MS (Cl) m/z=461, 463 (M⁺).

6-[4-(2-Bromo-5-fluorophenyl)-2-hydroxy-4-methyl-2-trifluoromethylvaleroylamino]-4-methyl-2,3-benzoxazin-1-one

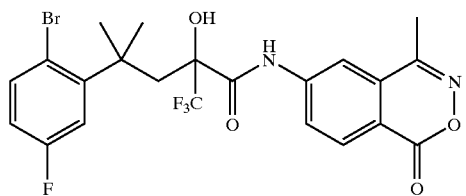

0.23 ml (1.25 mmol) of trifluoromethyl(trimethyl)silane and 256 mg (0.79 mmol) of cesium carbonate are added at 0° C. to a solution of 290 mg (0.63 mmol) of 6-[4-(2-bromo-5-fluorophenyl)-4-methyl-2-oxovaleroylamino]-4-methyl-2,3-benzoxazin-1-one in 7 ml of DMF. After 24 hours, the same amount of silane and base are added and stirred for another 24 hours at room temperature. The batch is diluted with 150 ml of ethyl acetate, washed with water and saturated NaCl, dried (Na₂SO₄) and concentrated by evaporation in a vacuum. Purification by column chromatography of the residue on silica gel yields 230 mg of product.

¹H-NMR (CDCl₃), δ (ppm)=1.55 (s, 3H), 1.63 (s, 3H), 2.58 (s, 3H), 3.10 (br. s, 1H), 6.63 (ddd, 1H), 7.11 (dd, 1H), 7.40 (dd, 1H), 7.62 (dd, 1H), 8.14 (d, 1H), 8.33 (d, 1H), 8.52 (br.s, 1H);

MS (Cl) m/z=531, 533 (M⁺).

EXAMPLE 9

6-[4-(Indan-4'-yl)-2-hydroxy-4-methyl-2-trifluoromethylvaleroylamino]-4-methyl-2,3-benzoxazin-1-one Precursors 4-(1-Hydroxy-1-methylethyl)indane 10 ml (14 mmol) of a 1.4 M methylmagnesium bromide solution in toluene-THF (3:1) is added in drops at 0° C. to a solution of 1.6 g (10 mmol) of 4-acetylindane (F. Dallacker, J. Van Wersch, Chem. Ber. 1972, 105, 2565) in 40 ml of THF. After 30 minutes at 0° C. and 1.5 hours at room temperature, the batch is diluted with 200 ml of ethyl acetate, washed with 1 M hydrochloric acid and saturated NaCl, dried (Na₂SO₄) and concentrated by evaporation in a vacuum. Column chromatography of the residue on silica gel with hexane-ethyl acetate yields 0.64 g of product.

¹H-NMR (CDCl₃), δ (ppm)=1.64 (s, 6H), 1.74 (s, 1H), 2.07 (pent, 2H), 2.90 (t, 2H), 3.16 (t, 2H), 7.11–7.19 (m, 2H), 7.29 (m, 1H).

6-[4-(Indan-4'-yl)-4-methyl-2-oxovaleric acid 0.63 g (3.4 mmol) of 4-{1-hydroxy-1-methylethyl)indane is introduced with 0.96 g (5.1 mmol) of 2-trimethylsiloxyacrylic acid-ethyl ester (H. Sugimura, K. Yoshida, Bull. Chem. Soc. Jpn. 1992, 65, 3209) into 20 ml of dichloromethane and treated at −70° C. with 0.31 ml (2.6 mmol) of tin(IV) chloride. After 20 minutes at −70° C., the batch is poured into semiconcentrated potassium carbonate solution and extracted with ethyl acetate. The combined extracts are washed with saturated NaCl, dried (Na₂SO₄) and concentrated by evaporation in a vacuum. 0.89 g of an oil, which is dissolved in 30 ml of EtOH-THF (2:1) and is reacted with 12.8 ml (12.8 mmol) of 1 M NaOH, is obtained. After 2 hours at room temperature, the batch is concentrated by evaporation in a vacuum, and the residue is taken up in 30 ml of water. The aqueous phase is washed with ether and acidified with 50 ml of 1 M hydrochloric acid. Extraction with ethyl acetate, drying (Na₂SO₄) and concentration by evaporation yields 0.64 g of acid.

¹H-NMR (CDCl₃), δ (ppm)=1.52 (s, 6H), 2.07 (pent, 2H), 2.85 (t, 2H), 3.08 (t, 2H), 3.42 (s, 2H), 5.02 (br.), 7.04–7.17 (m, 3H).

6-[4-(Indan-4'-yl)-4-methyl-2-oxovaleroylamino]-4-methyl-2,3-benzoxazin-1-one 0.63 g (2.6 mmol) of 6-[4-(indan-4'-yl)-4-methyl-2-oxovaleric acid and 0.69 g (3.9 mmol) of 6-amino-4-methyl-2,3-benzoxazin-1-one are converted into 0.31 g of product as described in Example 1.

¹H-NMR (CDCl₃), δ (ppm)=1.56 (s, 6H), 2.08 (pent, 2H), 2.59 (s, 3H), 2.83 (t, 2H), 3.12 (t, 2H), 3.52 (s, 2H), 7.07–7.17 (m, 3H), 7.72 (dd, 1H), 8.20 (d, 1H), 8.36 (d, 1H), 8.87 (br. s, 1H).

6-[4-(Indan-4'-yl)-2-hydroxy-4-methyl-2-trifluoromethylvaleroylamino]-4-methyl-2,3-benzoxazin-1-one

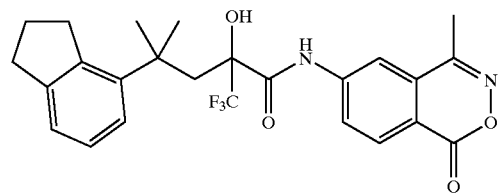

In a way similar to the instructions of Example 1, 0.31 g (0.77 mmol) of 6-[4-(indan-4'-yl)-4-methyl-2-oxovaleroylamino]-4-methyl-2,3-benzoxazin-1-one is reacted with 0.56 ml (3.1 mol) of trifluoromethyl(trimethyl)

silane and 626 mg (1.9 mmol) of cesium carbonate in 9 ml of DMF. After column chromatography on silica gel with hexane-ethyl acetate, 90 mg of product is obtained.

$^1$H-NMR (CDCl$_3$), δ (ppm)=1.47 (s, 3H), 1.49 (s, 3H), 2.11 (m, 2H), 2.62 (s, 3H), 2.76–2.92 (m, 4H), 2.96 (s, 1H), 3.17 (t, 2H), 7.14 (m, 4H), 7.63 (dd, 1H), 8.28 (d, 1H), 8.35 (d, 1H), 8.88 (br. s, 1H);

MS (Cl) m/z=475 (MH$^+$).

Separation of Enantiomers of Example 9

The enantiomer mixture of Example 9 is separated by chromatography on chiral support medium (CHIRALPAK AD$^{(R)}$, DAICEL Company) with hexane/ethanol (95:5, vv). Thus obtained from 830 mg of racemate are:

(−) 6-[4-(Indan-4'-yl)-2-hydroxy-4-methyl-2-trifluoromethylvaleroylamino]-4-methyl-2,3-benzoxazin-1-one as a first fraction: 310 mg, [MS (Cl) m/z=475 (MH$^+$), α$_D$=−55.7° (c=0.5 in tetrahydrofuran)] and (+) 6-[4-(Indan-4'-yl)-2-hydroxy-4-methyl-2-trifluoromethylvaleroylamino]-4-methyl-2,3-benzoxazin-1-one as a second fraction: 280 mg, [Flash point 196–197° C., α$_D$=+55.7° (c=0.5 in tetrahydrofuran)]

EXAMPLE 10

6-[4-(5-Fluoro-2-vinylphenyl)-2-hydroxy-4-methyl-2-trifluoromethylvaleroylamino]-4-methyl-2,3-benzoxazin-1-one 2-Benzoyl-4-(5-fluoro-2-vinylphenyl)-4-methylvaleric acid-methyl ester A solution of 0.53 g (1.25 mmol) of 2-benzoyl-4-(2-bromo-5-fluorophenyl)-4-methylvaleric acid-methyl ester and 77 mg (0.07 mmol) of tetrakis(triphenylphosphine) palladium in 40 ml of toluene is refluxed with vinyl(tributyl) stannane for 8 hours. Then, it is concentrated by evaporation and purified by column chromatography on silica gel with hexane-ethyl acetate: 320 mg of product.

$^1$H-NMR (CDCl$_3$), δ (ppm)=1.51 (s, 3H), 1.55 (s, 3H), 2.44 (dd, 1H), 2.66 (dd, 1H), 3.70 (s, 3H), 5.14 (dd, 1H), 5.33 (dd, 1H), 5.43 (dd, 1H), 6.77 (td, 1H), 6.97 (dd, 1H), 7.22–7.33 (m, 2H), 7.48 (m, 2H), 7.55 (m, 1H), 7.80 (d, 2H).

4-(5-Fluoro-2-vinylphenyl)-2-hydroxy-4-methylvaleric acid-methyl ester

Produced analogously to Example 8.

$^1$H-NMR (CDCl$_3$), δ (ppm)=1.48 (s, 3H), 1.53 (s, 3H), 1.98 (dd, 1H), 2.46 (dd, 1H), 2.50 (d, 1H), 3.70 (s, 3H), 3.96 (ddd, 1H), 5.28 (dd, 1H), 5.41 (dd, 1H), 6.90 (td, 1H), 7.12 (dd, 1H), 7.25 (dd, 1H), 7.33 (dd, 1H).

6-[4-(5-Fluoro-2-vinylphenyl)-4-methyl-2-oxovaleroylamino]-4-methyl-2,3-benzoxazin-1-one Produced analogously to Example 8.

$^1$H-NMR (CDCl$_3$), δ (ppm)=1.56 (s, 6H), 2.58 (s, 3H), 3.65 (s, 2H), 5.28 (dd, 1H), 5.34 (dd, 1H), 6.91 (td, 1H), 7.13 (dd, 1H), 7.20–7.30 (m, 2H), 7.78 (dd, 1H), 8.22 (d, 1H), 8.35 (d, 1H), 8.98 (br., 1H).

6-[4-(5-Fluoro-2-vinylphenyl)-2-hydroxy-4-methyl-2-trifluoromethylvaleroylamino]-4-methyl-2,3-benzoxazin-1-one

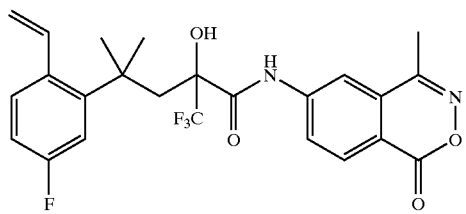

Produced analogously to Example 8.

$^1$H-NMR (CDCl$_3$), δ (ppm)=1.47 (s, 3H), 1.54 (s, 3H), 2.60 (s, 3H), 2.87 (m, 3H), 5.45 (dd, 1H), 5.50 (dd, 1H), 6.85 (td, 1H), 7.06 (dd, 1H), 7.25–7.37 (m, 2H), 7.67 (dd, 1H), 8.18 (d, 1H), 8.34 (d, 1H), 8.73 (br.s, 1H);

MS (ES+) m/z=479 (MH$^+$).

EXAMPLE 11

6-[2-Hydroxy-4-methyl-2-trifluoromethyl-4-(4-trifluoromethylphenyl)-valeroylamino]-4-methyl-2,3-benzoxazin-1-one 2-Methyl-2-(4-trifluomethylphenyl)propionitrile A solution of 6.80 g (41.4 mmol) of 4-fluorobenzotrifluoride in 250 m of toluene is mixed at 0° C. with 124 ml (62 mmol) of a 0.5 M potassium hexamethyldisilazide-THF solution and 9.44 g (137 mmol) of isobutyric acid nitrile. The batch is stirred for 4 hours at 60° C. and diluted after cooling with water and ethyl acetate. The organic phase is separated, washed with 10% H$_2$SO$_4$ and saturated NaCl, dried (Na$_2$SO$_4$) and concentrated by evaporation in a vacuum.

Column chromatography on silica gel with hexane-ethyl acetate yields 7.68 g of product.

$^1$H-NMR (CDCl$_3$) δ (ppm)=1.76 (s, 6H), 7.62 (d, 2H), 7.68 (d, 2H).

4-Methyl-4-(4-trifluomethylphenyl)-2-pentenoic acid-ethyl ester

A solution of 7.6 g (36 mmol) of 2-methyl-2-(4-trifluomethylphenyl)propionitrile in 250 ml of toluene is mixed at −70° C. with 57 ml (68 mmol) of a 1.2 M diisobutylaluminum hydride-toluene solution. After 1 hour at −70° C., 10% tartaric acid is added in drops to it, and it is stirred for 15 minutes at room temperature. The batch is diluted with ether, the organic phase is separated and washed with saturated NaCl, dried (Na$_2$SO$_4$) and concentrated by evaporation in a vacuum: 7.96 g of crude 2-methyl-2-(4-trifluomethylphenyl)propionaldehyde. 2.05 g (9.25 mmol) thereof is dissolved in 6 ml of DME and added in drops to a solution that was prepared from 3.10 g (13.9 mmol) of phosphonoacetic acid-triethyl ester and 0.55 g (13.9 mmol) of 60% sodium hydride in 12 ml of DME. After 1 hour at room temperature, the batch is mixed with saturated NH$_4$Cl and diluted with ethyl acetate and water. The phases are separated, the aqueous phase is extracted with ethyl acetate, and the combined organic extracts are washed with saturated NaCl, dried (Na$_2$SO$_4$) and concentrated by evaporation in a vacuum. The residue is purified on silica gel with hexane-ethyl acetate: 1.72 g of product.

$^1$H-NMR (CDCl$_3$), δ (ppm)=1.30 (t, 3H), 1.49 (s, 6H), 4.21 (q, 2H), 5.82 (d, 1H), 7.10 (d, 1H), 7.43 (d, 2H), 7.59 (d, 2H).

2-Hydroxy-4-methyl-4-(4-trifluoromethylphenyl)valeric acid-ethyl ester 1.72 g (6.0 mmol) of 4-methyl-4-(4-trifluomethylphenyl)-2-pentenoic acid-ethyl ester is stirred in ethyl acetate in the presence of 0.17 g of 10% palladium/activated carbon catalyst for 15 hours in a hydrogen atmosphere (1 atm). The batch is filtered on Celite and concentrated by evaporation in a vacuum: 1.72 g of 4-methyl-4-(4-trifluomethylphenyl) valeric acid-ethyl ester. 0.57 g (2.0 mmol) thereof is dissolved in 7 ml of THF and treated at −78° C. with 5.6 ml (2.8 mmol) of potassium hexamethyldisilazide-toluene solution. After 25 minutes, 0.73 g (2.8 mmol) of 3-phenyl-2-phenylsulfonyloxaziridine (F. A. Davis, S. Chattopadhyay, J.

C. Towson, S. Lal, T. Reddy J. Org. Chem. 1988, 53, 2087) in 7 ml of THF is added in drops to it and stirred for 30 minutes at −78° C. The batch is mixed with saturated NH₄Cl and heated within 1 hour to room temperature. THF is removed in a vacuum, the residue is taken up in ether, the solid is filtered off, the phases are separated, and the aqueous phase is extracted with ether. The combined organic extracts are washed with saturated NaCl, dried (Na₂SO₄) and concentrated by evaporation in a vacuum. Column chromatography on silica gel with hexane-ethyl acetate yields 0.14 g of product.

¹H-NMR (CDCl₃), δ (ppm)=1.26 (t, 3H), 1.42 (s, 3H), 1.50 (s, 3H), 1.90 (dd, 1H), 2.10 (br., 1H), 2.24 (dd, 1H), 3.94 (dd, 1H), 4.15 (m, 2H), 7.53 (d, 2H), 7.60 (d, 2H).

6-[4-Methyl-2-oxo-4-(4-trifluoromethylphenyl)-valeroylamino]-4-methyl-2,3-benzoxazin-1-one Produced analogously to Example 8.

¹H-NMR (CDCl₃), δ (ppm)=1.53 (s, 6H), 2.58 (s, 3H), 3.47 (s, 2H), 7.50 (d, 2H), 7.58 (d, 2H), 7.78 (dd, 1H), 8.21 (d, 1H), 8.35 (d, 1H), 8.98 (br., 1H);

MS (CI) m/z=433 (MH⁺).

6-[2-Hydroxy-4-methyl-2-trifluoromethyl-4-(4-trifluoromethylphenyl)-valeroyl-amino]-4-methyl-2,3-benzoxazin-1-one

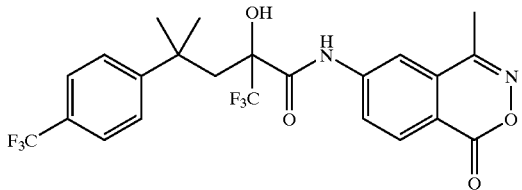

Produced analogously to Example 8.

¹H-NMR (CDCl₃), δ (ppm)=1.47 (s, 3H), 1.50 (s, 3H), 2.53 (d, 1H), 2.58 (s, 3H), 2.91 (s, 1H ), 2.95 (d, 1H), 7.55 (s, 4H), 7.62 (dd, 1H), 8.18 (d, 1H), 8.33 (d, 1H), 8.73 (br.s, 1H);

MS (ES+) m/z=503 (MH⁺).

EXAMPLE 12

6-[4-(2-Bromo-3,5-difluorophenyl)-2-hydroxy-4-methyl-2-trifluoromethylvaleroylamino]-4-methyl-2,3-benzoxazin-1-one

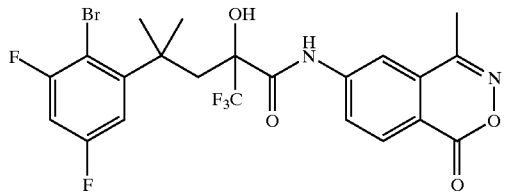

Produced analogously to Example 8.

¹H-NMR (CDCl₃), δ (ppm)=1.56 (s, 3H), 1.64 (s, 3H), 2.58 (s, 3H), 3.00 (d, 1H), 3.22 (d, 1H), 3.31 (br. s, 1H), 6.58 (td, 1H), 6.97 (dt, 1H), 7.64 (dd, 1H), 8.11 (d, 1H), 8.34 (d, 1H), 8.43 (br.s, 1H).

EXAMPLE 13

6-[4-(3,5-Difluorophenyl)-2-hydroxy-4-methyl-2-trifluoromethylvaleroylamino]-4-methyl-2,3-benzoxazin-1-one

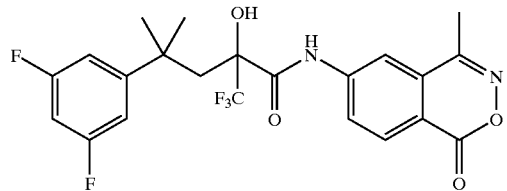

Example 13 accumulates as by-product in the synthesis of Example 12.

¹H-NMR (CDCl₃), δ (ppm)=1.41 (s, 3H), 1.44 (s, 3H), 2.44 (d, 1H), 2.60 (s, 3H), 2.80 (br. s, 1H), 2.89 (d, 1H), 6.53 (tt, 1H), 6.92 (m, 2H), 7.66 (dd, 1H), 8.24 (d, 1H), 8.35 (d, 1H), 8.70 (br.s, 1H).

EXAMPLE 14

6-[4-(5-Fluoro-2-trifluoromethylphenyl)-2-hydroxy-4-methyl-2-trifluoromethylvaleroylamino]-4-methyl-2,3-benzoxazin-1-one 2-(5-Fluoro-2-trifluoromethylphenyl)-acetonitrile 1.95 g (30 mmol) of potassium cyanide is added to a solution of 5.14 g (20 mmol) of 5-fluoro-2-trifluoromethylbenzyl bromide in 45 ml of ethanol/8 ml of water, and it is stirred for 64 hours at room temperature. The reaction solution is diluted with ethyl acetate and extracted with saturated sodium bicarbonate solution. The organic phase is washed with water, dried and concentrated by evaporation. The remaining residue is purified by bulb tube distillation and recrystallized. Yield: 3.6 g (89%).

Flash point 41–42° C.

2-(5-Fluoro-2-trifluoromethylphenyl)-2-methyl-propionitrile

Analogously to the process that is described for 2-(5-fluoro-2-methylphenyl)-2-methylpropionitrile, 2-(5-fluoro-2-trifluoromethylphenyl)-2-methyl-propionitrile is obtained as a colorless oil, boiling point 90° C./0.04 hPa.

2-(5-Fluoro-2-trifluoromethylphenyl)-2-methyl-propionaldehyde

Analogously to the process that is described for 2-(5-fluoro-2-methylphenyl)-2-methylpropionaldehyde, 2-(5-fluoro-2-trifluoromethylphenyl)-2-methyl-propionaldehyde is obtained as a colorless oil, boiling point 80° C./0.05 hPa.

4-(5-Fluoro-2-trifluoromethylphenyl)-4-methyl-oxovaleric acid

Analogously to the process that is described for 4-(5-fluoro-2-methylphenyl)-4-methyl-oxovaleric acid, 4-(5-fluoro-2-trifluoromethylphenyl)-4-methyl-oxovaleric acid is obtained as a viscous oil.

6-[4-(5-Fluoro-2-trifluoromethylphenyl)-4-methyl-2-oxovaleroylamino]-4-methyl-2,3-benzoxazin-1-one Analogously to the process that is described for 6-[4-(5-fluoro-2-methylphenyl)-4-methyl-2-oxovaleroylamino]-4-methyl-2,3-benzoxazin-1-one, 6-[4-(5-fluoro-2-trifluoromethylphenyl)-4-methyl-2-oxovaleroylamino]-4-methyl-2,3-benzoxazin-1-one is synthesized.

¹H-NMR (CDCl₃+DMSO), δ (ppm)=1.47 (s, 6H), 2.44 (s, 3H), 3.59 (s, 2H), 6.92 (dt, 1H), 7.33 (dd, 1H), 7.61 (dd, 1H), 8.03 (dd, 1H), 8.16 (d, 1H), 8.30 (d, 1H), 10.34 (bs, 1H).

6-[4-(5-Fluoro-2-trifluoromethylphenyl)-2-hydroxy-4-methyl-2-trifluoromethyl-valeroylamino]-4-methyl-2,3-benzoxazin-1-one

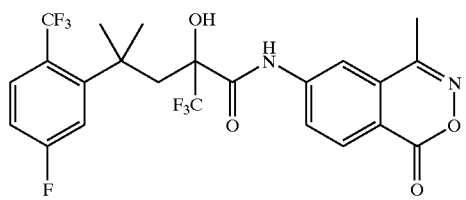

Analogously to the process that is described for 6-[4-(5-fluoro-2-methylphenyl)-2-hydroxy-4-methyl-2-trifluoromethylvaleroylamino]-4-methyl-2,3-benzoxazin-1-one, 6-[4-(5-fluoro-2-trifluoromethylphenyl)-2-hydroxy-4-methyl-2-trifluoromethylvaleroylamino]-4-methyl-2,3-benzoxazin-1-one is synthesized.

$^1$H-NMR (CDCl$_3$) δ (ppm)=1.42 (s, 3H), 1.55 (s, 3H), 2.56 (d, 1H), 2.57 (s, 3H), 2.91 (d, 1H), 3.28 (bs, 1H), 6.85 (dt, 1H), 7.32 (dd, 1H), 7.56–7.66 (m, 2H), 8.13 (d, 1H), 8.34 (d, 1H), 8.51 (bs, 1H);

MS (EI) m/z=520 (M$^+$).

Separation of the Enantiomers of Example 14

The enantiomer mixture of Example 14 is separated by chromatography on chiral support medium (CHIRALPAK AD$^{(R)}$, DAICEL Company) with hexane/ethanol (19:1, vv). Thus obtained from 100 mg of racemate are:

(−)-6-[4-(5-Fluoro-2-trifluoromethylphenyl)-2-hydroxy-4-methyl-2-trifluoromethyl-valeroylamino]-4-methyl-2,3-benzoxazin-1-one as a first fraction: 40 mg, [flash point 162–165° C., α$_D$=−45.5° (c=0.5 in tetrahydrofuran)] and (+)-6-[4-(5-Fluoro-2-trifluoromethylphenyl)-2-hydroxy-4-methyl-2-trifluoromethyl-valeroylamino]-4-methyl-2,3-benzoxazin-1-one as a second fraction: 38 mg, [flash point 160–165° C.]

Analogously to Example 14, the compounds of Table 4 are d.

Trifluoromethyl Compounds

TABLE 4

| Compound | R5 | R6 | R7 | R8 | R1/R2 | Flash point [° C.] | Isomerism or [α]$_D$ |
|---|---|---|---|---|---|---|---|
| 1 | H | H | H | H | CH$_3$ | 154–156 | racemate |
| 2 | H | H | H | H | CH$_3$ | 164–170 | −72.8 |
| 3 | H | H | H | H | CH$_3$ | 188–190 | +69.0 |
| 4 | H | F | H | H | CH$_3$ | 170–172 | racemate |
| 5 | H | F | H | H | CH$_3$ | 173–175 | −67.5 |
| 6 | H | F | H | H | CH$_3$ | 174–177 | (+)-form |
| 7 | H | H | F | H | CH$_3$ | 170 | racemate |
| 8 | H | H | F | H | CH$_3$ | 162–166 | −45.5 |
| 9 | H | H | F | H | CH$_3$ | 160–165 | (+)-form |
| 10 | H | H | Cl | H | CH$_3$ | 172 | racemate |
| 11 | H | H | Cl | H | CH$_3$ | 178–181 | −143.1 |
| 12 | H | H | Cl | H | CH$_3$ | 180–182 | (+)-form |

EXAMPLE 15

6-Hydroxy-4-methyl-2-trifluoromethyl-4-(1-naphthyl)-valeroylamino]-4-methyl-2,3-benzoxazin-1-one 2-Methyl-2-(1-naphthyl)-propionitrile A solution of 16.7 g (100 mmol) of 1-naphthylacetonitrile in 200 m of DMF and 15 ml (240 mmol) of methyl iodide is mixed at 0° C. with 10.4 g (260 mmol) of sodium hydride (addition within 2.5 hours). The batch is stirred for 3 hours at 0° C. and for 18 hours at 25° C. It is mixed with ice and ethyl acetate. The organic phase is acidified with 10% H$_2$SO$_4$, washed three times with water, dried (Na$_2$SO$_4$) and concentrated by evaporation in a vacuum. A large-scale purification is carried out by bulb tube distillation (boiling range 60–130° C.) in an oil pump vacuum; yield: 18.8 g.

$^1$H-NMR (CDCl$_3$), δ (ppm)=2.00 (s, 6H), 7.41–7.60 (m, 3H), 7.64 (ddd, 1H), 7.87 (d br., 1H), 7.93 (dd, 1H), 8.55 (d, 1H).

4-Methyl-4-(1-naphthyl)-2-pentenoic acid-ethyl ester

Analogously to the production of 4-methyl-4-(4-trifluomethylphenyl)-2-pentenoic acid-ethyl ester of Example 11, 7.62 g of the product is obtained from 8.81 g (45.1 mmol) of 2-methyl-2-(1-naphthyl)-propionitrile.

$^1$H-NMR (CDCl$_3$), δ (ppm)=1.25 (t, 3H), 1.70 (s, 6H), 4.16 (q, 2H), 5.73 (d, 1H), 7.38–7.50 (m, 4H), 7.53 (dd, 1H), 7.78 (d, 1H), 7.81–7.89 (m, 1H), 8.00–8.08 (m, 1H).

2-Hydroxy-4-methyl-4-(1-naphthyl)-valeric acid-ethyl ester

Analogously to the production of 2-hydroxy-4-methyl-4-(4-trifluomethylphenyl)-valeric acid-ethyl ester of Example 11, 3.52 g of the product is obtained from 7.62 g (28.4 mmol) of 4-methyl-4-(1-naphthyl)-2-pentenoic acid-ethyl ester.

$^1$H-NMR (CDCl$_3$), δ (ppm)=1.14 (t, 3H), 1.72 (s, 3H), 1.74 (s, 3H), 2.27 (dd, 1H), 2.52 (dd, 1H), 2.76 (dd, 1H), 3.95–4.08 (m, 3H), 7.38–7.51 (m, 3H), 7.57 (d, 1H), 7.75 (d, 1H), 7.88 (dd, 1H), 8.40 (d, 1H).

6-[4-Methyl-2-oxo-4-(1-naphthyl)-valeroylamino]-4-methyl-2,3-benzoxazin-1-one

Produced analogously to Example 11. 861 mg of the product is obtained.

$^1$H-NMR (CDCl$_3$), δ (ppm)=1.59 (s, 3H), 1.78 (s, 6H), 2.57 (s, 3H), 3.88 (s, 2H), 7.44 (m, 2H), 7.54 (m, 2H), 7.69 (dd, 1H), 7.75 (d br., 1H), 7.87 (dd, 1H), 8.15 (d, 1H), 8.32 (d, 1H), 8.46 (d br., 1H).

6-[2-Hydroxy-4-methyl-2-trifluoromethyl-4-(1-naphthyl)-valeroylamino]-4-methyl-2,3-benzoxazin-1-one

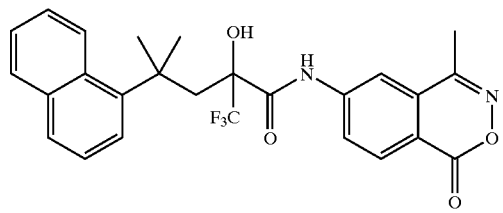

Produced analogously to Example 8. 77.1 mg of the product is obtained.

$^1$H-NMR (CDCl$_3$), δ (ppm)=1.57 (s, 3H), 1.67 (s, 3H), 1.78 (s, 3H), 2.54 (s, 2H), 3.10 (d, 1H), 3.23 (d, 1H), 5.30 (s, 2H), 7.25–7.38 (m, 2H), 7.46 (dd, 1H), 7.51 (d, 1H), 7.60 (m, 2H), 7.76 (d, 1H), 7.97 (d br., 1H), 8.24 (d, 1H), 8.42 (d, 1H).

EXAMPLE 16

6-[3-{1-(2-Chlorophenyl)-cyclopropyl}-2-hydroxy-2-trifluoromethylpropionyl]-amino-4-methyl-2,3-benzoxazin-1-one Precursors 1-(2-Chlorophenyl)-cyclopropane-carbonitrile A solution of 13.1 g of 2-chlorophenylacetonitrile and 20.3 g of 1,2-dibromopropane in 142 ml of DMF is mixed with 9 g of sodium hydride [55–65% in oil] at room temperature. It is stirred for several hours and carefully added to water. After extraction with ethyl acetate and filtration by silica gel, the desired product is obtained: 13.1 g MS (ei): $M^{(+)}$=177

1-(2-Chlorophenyl)-1-cyclopropane carbaldehyde 13.1 g of (1-(2-chlorophenyl)-1-cyclopropane carbaldehyde in 116 ml of toluene is mixed at −70° C. drop by drop with 64.5 ml of diisobutylaluminum hydride. After 4 hours at −70° C., 343 ml of ethyl acetate is added. It is allowed to come to room temperature overnight. Water and ethyl acetate are added, filtered on diatomaceous earth, ethyl acetate solution is washed with water, dried ($Na_2SO_4$) and concentrated by evaporation. After flash chromatography on silica gel with hexane-ethyl acetate (8:2), 9.7 g of the product is obtained.

MS (ei): $M^{(+)}$=180

2-Ethoxy-3-[1-(2-chlorophenyl)-1-cyclopropyl]-acrylic acid ethyl ester 14.3 g of phosphonate in 40 ml of tetrahydrofuran is mixed at 0° C. with 29 ml of lithium diisopropylamide. It is stirred for 20 more minutes at 0° C. 9.7 g of 1-(2-chlorophenyl)-1-cyclopropane carbaldehyde in 40 ml of tetrahydrofuran is added in drops. After 24 hours at room temperature, it is mixed with water, extracted with ethyl acetate, ethyl acetate solution is washed with water and dried ($Na_2SO_4$). After concentration by evaporation, 15.5 g of the product is obtained.

MS (ei): $M^{(+)}$=294

2-Ethoxy-3-[1-(2-chlorophenyl)-1-cyclopropyl]-acrylic acid 15.4 g of 2-ethoxy-3-[1-(2-chlorophenyl)-1-cyclopropyl]-acrylic acid ethyl ester in 350 ml of 1 M sodium hydroxide solution (ethanol-water 2:1) is stirred for 24 hours at room temperature. Solvent is distilled off, residue is distributed between water and diethyl ether, water solution is acidified with 2N hydrochloric acid, and extracted with diethyl ether. After the organic phase is washed with water, dried (Na2SO4) and concentrated by evaporation, 11.2 g of the product is obtained.

MS (ei): $M^{(+)}$=266

3-[1-(2-Chlorophenyl)-1-cyclopropyl]-2-oxo-propionic acid 11.2 g of 2-ethoxy-3-[1-(2-chlorophenyl)-1-cyclopropyl]-acrylic acid is stirred in 230 ml of 1 M sulfuric acid and 42 ml of concentrated acetic acid for 24 hours at 110° C. Water is added, it is extracted with ethyl acetate, and ethyl acetate solution is washed with water. After drying (Na2SO4) and concentration by evaporation, 10.7 g of the product is obtained.

MS (ei): $M^{(+)}$=238

$^1$H-NMR (CDCl$_3$), a (ppm)=0.98 (m, 4H), 3.28 (s, 2H), 7.13–7.22 (m, 2H), 7.29–7.35 (m, 1H), 7.43–7.49 (m, 1H)

6-{3-[1-(2-Chlorophenyl)-cyclopropyl]-2-oxopropionylamino}-4-methyl-2,3-benzoxazin-1-one 10.7 g of 3-[1-(2-chlorophenyl)-1-cyclopropyl]-2-oxopropionic acid in 175 ml of dimethyl acetamide is mixed at −5° C. with 4.1 ml of thionyl chloride, and it is stirred for 20 minutes. Then, 5.0 g of MBO is added in solid form. After 20 hours at room temperature, water and ethyl acetate are added, ethyl acetate solution is washed with water, dried (Na2SO4) and concentrated by evaporation. After chromatography on silica gel with hexane-ethyl acetate (0%–30%), 9.6 g of the product is obtained.

MS (ei) $M^{(+)}$=397

6-{3-[1-(2-Chlorophenyl)-cyclopropyl]-2-hydroxy-2-trifluoromethylpropionylamino}-4-methyl-2,3-benzoxazin-1-one 9.5 g of 6-{3-[1-(2-chlorophenyl)-cyclopropyl]-2-oxopropionylamino}-4-methyl-2,3-benzoxazin-1-one in 140 ml of dimethylformamide is mixed at 0° C. with 16.9 ml of trifluoromethyl-trimethylsilane and 9.65 g of cesium carbonate. After 24 hours at room temperature, a spatula tip full of tetrabutylammonium fluoride hydrate is added, and it is stirred for 30 more minutes. It is mixed with water and ethyl acetate, ethyl acetate solution is washed with water, dried (Na2SO4) and concentrated by evaporation. After chromatography on silica gel with hexane-ethyl acetate (0%–30%), 2.98 g of the product is obtained.

Flash point 195–196° C.

Separation of the Enantiomers of Example 16

The enantiomer mixture of Example 16 is separated by chromatography on chiral support medium (CHIRALPAK AD$^{(R)}$, DAICEL Company) with hexane/ethanol. Thus obtained from 2.68 g of racemate are:

(−)-6-[3-{1-(2-Chlorophenyl)-cyclopropyl}-2-hydroxy-2-trifluoromethylpropionyl]-amino-4-methyl-2,3-benzoxazin-1-one as a first fraction: 1.3 g, [flash point 233–235° C., $\alpha_D$=−81.4° (c=0.5 in chloroform)] and (+)-6-[3-{1-(2-Chlorophenyl)-cyclopropyl}-2-hydroxy-2-trifluoromethylpropionyl]-amino-4-methyl-2,3-benzoxazin-1-one as a second fraction: 1.25 g, [flash point 238–240° C.]

Analogously to Example 16, the compounds of Tables 5–8 are obtained.

Chlorine Compounds

TABLE 5

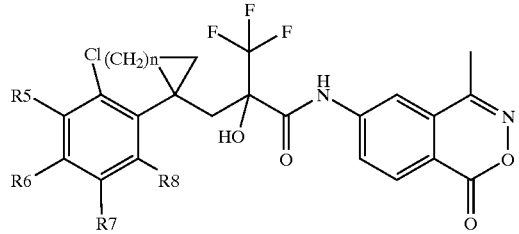

| Compound | R5 | R6 | R7 | R8 | n = | Flash point [° C.] | Isomerism or [α]$_D$ |
|---|---|---|---|---|---|---|---|
| 1 | H | H | H | H | 2 | 231–233 | −47.1 |
| 2 | H | H | H | H | 2 | 230–232 | (+)-form |
| 3 | H | H | H | H | 3 | 195–197 | −70.5 |
| 4 | H | H | H | H | 3 | 202–203 | (+)-form |
| 5 | H | F | H | H | 1 | 228–230 | racemate |
| 6 | H | F | H | H | 1 | 218–219 | −88.6 |
| 7 | H | F | H | H | 1 | 217–219 | (+)-form |
| 8 | H | F | H | H | 2 | 212–214 | racemate |
| 9 | H | F | H | H | 2 | 236–238 | +74.2 |
| 10 | H | F | H | H | 2 | 235–237 | −75.0 |
| 11 | H | H | F | H | 1 | 196 | racemate |
| 12 | H | H | F | H | 1 | 239–240 | −95.4 |
| 13 | H | H | F | H | 1 | 239–240 | (+)-form |
| 14 | H | H | F | H | 2 | 222–223 | racemate |
| 15 | H | H | F | H | 2 | 247–249 | 77.6 |
| 16 | H | H | F | H | 2 | 247–249 | +79.6 |
| 17 | H | Cl | H | H | 1 | 235–239 | −81.6 |

TABLE 5-continued

[Structure: Chlorophenyl compound with R5, R6, R7, R8 substituents, (CH2)n-cyclopropyl bearing CF3, connected via hydroxyl/amide to methyl-benzoxazinone]

| Compound | R5 | R6 | R7 | R8 | n = | Flash point [°C.] | Isomerism or [α]_D |
|---|---|---|---|---|---|---|---|
| 18 | H | Cl | H | H | 1 | 199–201 | (+)-form |
| 19 | H | Cl | H | H | 2 | 232 | −46.7 |
| 20 | H | Cl | H | H | 2 | 232–234 | (+)-form |

Trifluoromethyl Compounds

TABLE 6

[Structure: Trifluoromethylphenyl compound analog]

| Compound | R5 | R6 | R7 | R8 | n = | Flash point [°C.] | Isomerism or [α]_D |
|---|---|---|---|---|---|---|---|
| 21 | H | H | H | H | 1 | 205 | racemate |
| 22 | H | H | H | H | 1 | 222–223 | −96.5 |
| 23 | H | H | H | H | 1 | 219–221 | (+)-form |
| 24 | H | H | H | H | 2 | 218–222 | racemate |
| 25 | H | H | H | H | 2 | 220–221 | −16.4 |
| 26 | H | H | H | H | 2 | 220–222 | (+)-form |
| 27 | H | H | H | H | 4 | 150–153 | racemate |
| 28 | H | H | F | H | 1 | 242–245 | racemate |
| 29 | H | H | F | H | 1 | 235–246 | −40.1 |
| 30 | H | H | F | H | 1 | 244–246 | (+)-form |
| 31 | H | H | F | H | 2 | 241–244 | racemate |
| 32 | H | H | F | H | 2 | 242–244 | −82.7 |
| 33 | H | H | F | H | 2 | 242–244 | (+)-form |

Fluorine Compounds

TABLE 7

[Structure: Fluorophenyl compound analog]

| Compound | R5 | R6 | R7 | R8 | n = | Flash point [°C.] | Isomerism or [α]_D |
|---|---|---|---|---|---|---|---|
| 34 | H | H | H | H | 1 | 215–216 | racemate |
| 35 | H | H | H | H | 1 | 260–262 | −113.3 |
| 36 | H | H | H | H | 1 | 260–263 | (+)-form |
| 37 | H | H | H | H | 2 | 190–191 | racemate |

TABLE 7-continued

| Compound | R5 | R6 | R7 | R8 | n = | Flash point [°C.] | Isomerism or [α]_D |
|---|---|---|---|---|---|---|---|
| 38 | H | H | H | H | 2 | 198–201 | −103.4 |
| 39 | H | H | H | H | 2 | 207–209 | +103 |
| 40 | H | H | H | H | 3 | 168–171 | −117.6 |
| 41 | H | H | H | H | 3 | 167–170 | +112.3 |
| 42 | H | H | H | H | 4 | 90–93 | racemate |
| 43 | H | H | H | H | 4 | 178–184 | −105 |
| 44 | H | H | H | H | 4 | 185–187 | +102.6 |
| 45 | F | H | H | H | 1 | 230–232 | racemate |
| 46 | F | H | H | H | 1 | 238–250 | −106.3 |
| 47 | F | H | H | H | 1 | 254–256 | (+)-form |
| 48 | F | H | H | H | 2 | 182–185 | racemate |
| 49 | H | H | F | H | 1 | 198–199 | racemate |
| 50 | H | H | F | H | 1 | 240 | −130.2 |
| 51 | H | H | F | H | 1 | 241 | (+)-form |
| 52 | F | H | F | H | 1 | 215 | racemate |
| 53 | F | H | F | H | 2 | 205 | racemate |

Bromine Compounds

TABLE 8

[Structure: Bromophenyl compound analog]

| Compound | R5 | R6 | R7 | R8 | n = | Flash point [°C.] | Isomerism or [α]_D |
|---|---|---|---|---|---|---|---|
| 54 | H | H | H | H | 1 | 196–200 | racemate |
| 55 | H | H | H | H | 1 | 239–241 | −56.6 |
| 56 | H | H | H | H | 1 | 240–241 | +56.0 |

EXAMPLE 17

6-[2-Hydroxy-4-methyl-4-(3-methyl-2-nitrophenyl)-2-trifluoromethylvaleroylamino]-4-methyl-2,3-benzoxazin-1-one Precursors 2-Methyl-2-(3-methyl-2-nitrophenyl)-propionitrile Analogously to the process that is described for 2-(5-fluoro-2-methylphenyl)-2-methylpropionitrile, 2-methyl-2-(3-methyl-2-nitrophenyl)-propionitrile is synthesized, boiling point 140° C./0.05 hPa.

2-Methyl-2-(3-methyl-2-nitrophenyl)-propionaldehyde

Analogously to the process that is described for 2-(5-fluoro-2-methylphenyl)-2-methylpropionaldehyde, 2-methyl-2-(3-methyl-2-nitrophenyl)-propionaldehyde, boiling point 140° C./0.05 hPa, is obtained.

4-Methyl-4-(3-methyl-2-nitrophenyl)-2-oxovaleric acid

Analogously to the process that is described for 4-(5-fluoro-2-methylphenyl)-4-methyl-2-oxovaleric acid, 4-methyl-4-(3-methyl-2-nitrophenyl)-2-oxovaleric acid is obtained as an oil.

6-[4-Methyl-4-(3-methyl-2-nitrophenyl)-2-oxovaleroylamino]-4-methyl-2,3-benzoxazin-1-one is obtained analogously to 5-[4-(5-fluoro-2-methylphenyl)-4-methyl-2-oxovaleroylamino]phthalide from 4-methyl-4-(3-methyl-2-nitrophenyl)-2-oxovaleric acid and 6-amino-2,3-benzoxazin-1-one, flash point 184–187° C.

6-[2-Hydroxy-4-methyl-4-(3-methyl-2-nitrophenyl)-2-trifluoromethylvaleroylamino]-4-methyl-2,3-benzoxazin-1-one

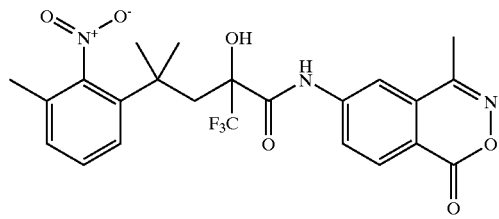

was obtained analogously to Example 1 from 6-[4-methyl-4-(3-methyl-2-nitrophenyl)-2-oxovaleroylamino]-4-methyl-2,3-benzoxazin-1-one, flash point 201–203° C.

EXAMPLE 18

5-[4-(2-Amino-5-fluorophenyl)-2-hydroxy-4-methyl-2-trifluoromethylvaleroyl-amino]-phthalide

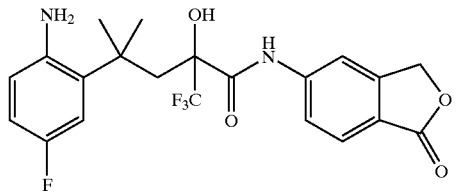

65.8 mg (5-fluoro-2-nitrophenyl)-2-hydroxy-4-methyl-2-trifluoromethylvaleroylamino]-phthalide in 15 ml of methanol is reduced at normal pressure within 3 hours in the presence of 20 mg of palladium/carbon (10%) with hydrogen, suctioned off on diatomaceous earth and concentrated by evaporation. After recrystallization from ethyl acetate/diisopropyl ether, 51 mg of 5-[4-(2-amino-5-fluorophenyl)-2-hydroxy-4-methyl-2-trifluoromethylvaleroylamino]-phthalide of flash point 174° C. is obtained.

EXAMPLE 19

6-[4-(2-Amino-5-fluorophenyl)-2-hydroxy-4-methyl-2-trifluoromethylvaleroyl-amino]-4-methyl-2,3-benzoxazin-1-one

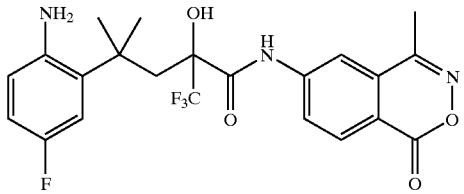

42 mg of 6-[4-(5-fluoro-2-nitrophenyl)-2-hydroxy-4-methyl-2-trifluoromethylvaleroylamino]-4-methyl-2,3-benzoxazin-1-one is dissolved in 1 ml of acetic acid and 1 ml of tetrahydrofuran b, mixed with 22.5 mg of iron powder and stirred for 16 hours at room temperature. It is suctioned off on diatomaceous earth, concentrated by evaporation, the residue is taken up in ethyl acetate and washed with a saturated sodium hydrogen carbon solution. After chromatography on silica gel with hexane/ethyl acetate (1.5+1) and recrystallization from diisopropyl ether, 10 mg of 6-[4-(2-amino-5-fluorophenyl)-2-hydroxy-4-methyl-2-trifluoromethylvaleroylamino]-4-methyl-2,3-benzoxazin-1-one is obtained, flash point 208° C.

EXAMPLE 20

6-[4-(2-Acetylamino-5-fluorophenyl)-2-hydroxy-4-methyl-2-trifluoromethyl-valeroylamino]-4-methyl-2,3-benzoxazin-1-one

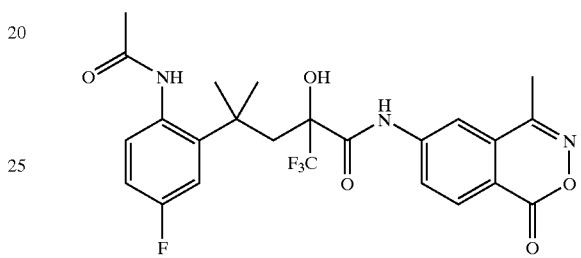

9.4 mg of 6-[4-(2-amino-5-fluorophenyl)-2-hydroxy-4-methyl-2-trifluoromethylvaleroylamino]-4-methyl-2,3-benzoxazin-1-one and 0.04 ml of acetic acid anhydride in 0.5 ml of tetrahydrofuran are stirred for 2 days at room temperature, and mixed with ethyl acetate and sodium bicarbonate solution. The ethyl acetate solution is dried and concentrated by evaporation. After chromatography on silica gel, 8 mg of 6-[4-(2-acetylamino-5-fluorophenyl)-2-hydroxy-4-methyl-2-trifluoromethylvaleroylamino]-4-methyl-2,3-benzoxazin-1-one is obtained.

MS (ei): M$^{(+)}$=510

EXAMPLE 21

5-[4-(2-Acetylamino-5-fluorophenyl)-2-hydroxy-4-methyl-2-trifluoromethyl-valeroylamino]-phthalide

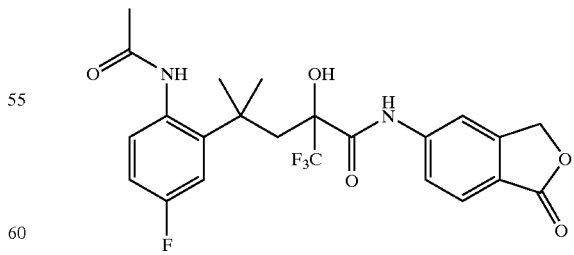

is obtained analogously to Example 20 from 5-[4-(2-amino-5-fluorophenyl)-2-hydroxy-4-methyl-2-trifluoromethylvaleroylamino]-phthalide, flash point 125° C.

EXAMPLE 22

5-[4-(5-Fluoro-2-mesylaminophenyl)-2-hydroxy-4-methyl-2-trifluoromethyl-valeroylamino]-phthalide

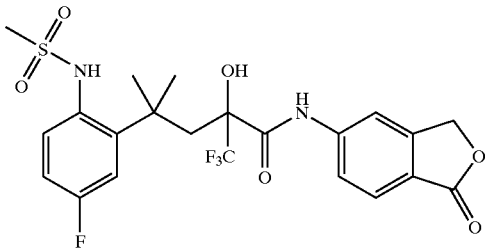

17.7 mg of 5-[4-(2-amino-5-fluorophenyl)-2-hydroxy-4-methyl-2-trifluoromethylvaleroylamino]-phthalide, 0.4 ml of pyridine and 0.078 ml of mesyl chloride are stirred for 17 hours at room temperature, mixed with ethyl acetate, and washed three times with 1N hydrochloric acid. The ethyl acetate solution is dried and concentrated by evaporation. After chromatography on silica gel with ethyl acetate/hexane (1:1), 11 mg of 5-[4-(5-fluoro-2-mesylaminophenyl)-2-hydroxy-4-methyl-2-trifluoromethylvaleroyl-amino]-phthalide is obtained, flash point 218° C.

EXAMPLE 23

6-[4-(2-Bromo-3-methoxyphenyl)-2-hydroxy-4-methyl-2-trifluoromethyl-valeroylamino]-4-methyl-2,3-benzoxazin-1-one is obtained analogously to Example 3 from 6-[4-(2-bromo-3-methoxyphenyl)-4-methyl-2-oxovaleroylamino]-4-methyl-2,3-benzoxazin-1-one, MS (esi): M$^{(+)}$+1=543 ($^{79}$Br) and 545 ($^{81}$Br)

Separation of the Enantiomers of Example 23

The enantiomer mixture of Example 23 is separated by chromatography on chiral support medium (CHIRALPAK AD$^{(R)}$, DAICEL Company) with hexane/ethanol (93:7, vv). Thus obtained from 200 mg of racemate are:

(−)-6-[4-(2-Bromo-3-methoxyphenyl)-2-hydroxy-4-methyl-2-trifluoromethyl-valeroylamino]-4-methyl-2,3-benzoxazin-1-one as a first fraction: 86 mg, [flash point 233–235° C., $\alpha_D$=−81.40° (c=0.5 in chloroform)] and (+)-6-[4-(2-Bromo-3-methoxyphenyl)-2-hydroxy-4-methyl-2-trifluoromethyl-valeroylamino]-4-methyl-2,3-benzoxazin-1-one as a second fraction: 82 mg.

EXAMPLE 24

(+)-6-[4-(2-Bromo-3-hydroxyphenyl)-2-hydroxy-4-methyl-2-trifluoromethyl-valeroylamino]-4-methyl-2,3-benzoxazin-1-one

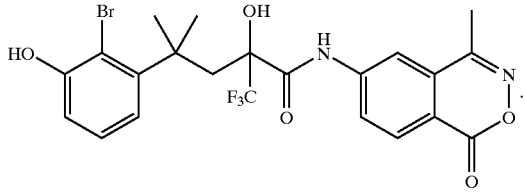

78 mg of (+)-6-[4-(2-bromo-3-methoxyphenyl)-2-hydroxy-4-methyl-2-trifluoromethyl-valeroylamino]-4-methyl-2,3-benzoxazin-1-one is mixed in 1.4 ml of dichloromethane at 0° C. with 0.71 ml of a 1 molar solution of boron tribromide in dichloromethane. After 2 hours of stirring at 0° C., the mixture is added to water, extracted with ethyl acetate, the organic phase is dried (Na$_2$SO$_4$) and concentrated by evaporation. After the residue is triturated with hexane, the title compound is obtained in crystalline form, flash point 226–231° C., [α]$_D$=+91.1° (c=0.5 in chloroform)

EXAMPLE 25

(−)-6-[4-(2-Bromo-3-hydroxyphenyl)-2-hydroxy-4-methyl-2-trifluoromethyl-valeroylamino]-4-methyl-2,3-benzoxazin-1-one

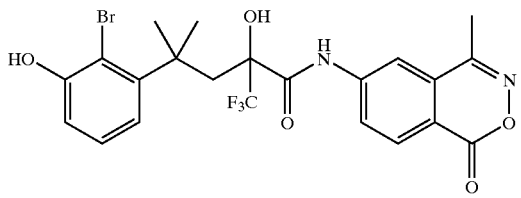

Example 25 is produced analogously to Example 24 starting form the corresponding (−)-6-[4-(2-bromo-3-methoxyphenyl)-2-hydroxy-4-methyl-2-trifluoromethyl-valeroylamino]-4-methyl-2,3-benzoxazin-1-one. Flash point 227–231° C., [α]$_D$=−94.3° (c=0.5 in chloroform).

EXAMPLE 26

6-[4-(2,3-Difluorophenyl)-2-hydroxy-4-methyl-2-trifluoromethylcaproylamino]-4-methyl-2,3-benzoxazin-1-one Precursors 2-Methyl-2-(2,3-difluorophenyl)butyronitrile and 2-methyl-2-(2,6-difluorophenyl)butyronitrile

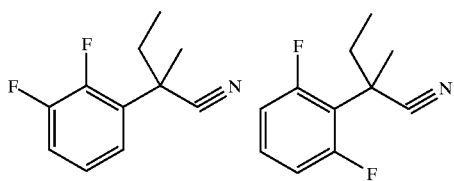

A solution of 5.0 g (37.85 mmol) of 1,2,3-trifluorobenzene, 3.30 g (39.74 mmol) of 2-methylbutylnitrile and 75.7 ml (0.5 M in toluene) of potassium-bis-trimethylsilylamide in 182 ml of toluene is heated for 3 hours at 60° C. It is mixed with ice water and ether. The organic phase is acidified with 10% H$_2$SO$_4$ and washed three times with water, dried (Na$_2$SO$_4$) and concentrated by evaporation in a vacuum. After chromatography on silica gel with 0–4% ether-hexane, 3.8 g of 2-methyl-2-(2,3-difluorophenyl)butyronitrile and 1.6 g of 2-methyl-2-(2,6-difluorophenyl)butyronitrile are obtained.

2-Methyl-2-(2,3-difluorophenyl)butyronitrile:

$^1$H-NMR (CDCl$_3$), δ (ppm)=0.88 (t, 3H), 1.81 (s, 3H), 1.95–2.1 (m, 1H), 2.1–2.25 (m, 1H), 7.05–7.2 (m, 2H), 7.3–7.4 (m, 1H).

2-Methyl-2-(2,6-difluorophenyl)butyronitrile:

$^1$H-NMR (CDCl$_3$), δ (ppm)=1.06 (t, 3H), 1.89 (t, 3H), 1.95–2.1 (m, H), 2.15–2.3 (m, H), 6.85–6.95 (m, 2H), 7.2–7.3 (m, 1H).

2-(2,3-Difluorophenyl)-2-methylbutyraldehyde

Analogously to the process that is described for 2-(5-fluoro-2-methylphenyl)-2-methylpropionaldehyde, 2-(2,3-difluorophenyl)-2-methylbutyronitrile is obtained as a colorless oil.

$^1$H-NMR (CDCl$_3$), δ (ppm)=0.79 (t, 3H), 1.41 (s, 3H), 1.85–2.0 (m, 1H), 2.0–2.15 (m, 1H), 7.0–7.3 (m, 3H), 9.68 (d, 1H).

4-(2,3-Difluorophenyl)-4-methyl-2-oxocaproic acid

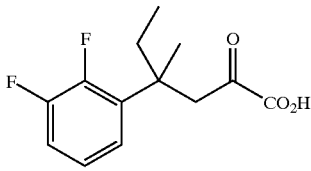

Analogously to the process that is described for 4-(5-fluoro-2-methyphenyl)-4-methyl-2-oxovaleric acid, 4-(2,3-difluorophenyl)-4-methyl-2-oxocaproic acid is obtained:
$^1$H-NMR (CDCl$_3$), δ (ppm)=0.71 (t, 3H), 1.47 (s, 3H), 1.7 (m, H), 2.0 (m, 1H), 3.26 (d, 1H), 3.74 (d, 1H), 6.9–7.1 (m, 3H).

6-[4-(2,3-Difluorophenyl)-4-methyl-2-oxocaproylamino]-4-methyl-2,3-benzoxazin-1-one

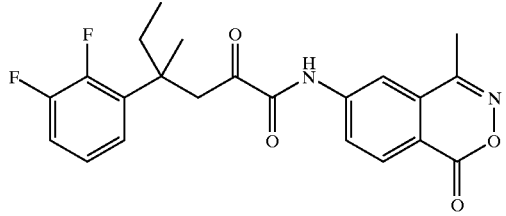

Analogously to the process that is described for 6-[4-(5-fluoro-2-methylphenyl)-4-methyl-2-oxovaleroylamino]-4-methyl-2,3-benzoxazin-1-one, 6-[4-(2,3-difluorophenyl)-4-methyl-2-oxocaproylamino]-4-methyl-2,3-benzoxazin-1-one is obtained:

$^1$H-NMR (CDCl$_3$), δ (ppm)=0.73 (t, 3H), 1.5 (s, 3H), 1.7 (m, 1H), 2.05 (m, 1H), 2.58 (s, 3H), 3.37 (d, 1H), 3.84 (d, 1H), 7.0 (m, 3H), 7.72 (dd, 1H), 8.24 (d, 1H), 8.33 (d, 1H), 9.0 (bs, 1H).

6-[4-(2,3-Difluorophenyl)-2-hydroxy-4-methyl-4-trifluoromethylcaproylamino]-4-methyl-2,3-benzoxazin-1-one

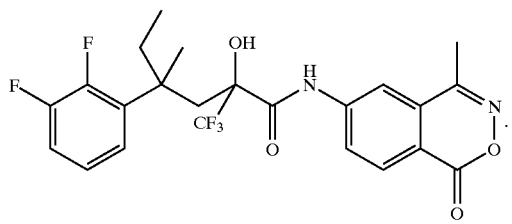

Analogously to the process that is described for 6-[4-(5-fluoro-2-methylphenyl)-2-hydroxy-4-methyl-2-trifluoromethylvaleroylamino]-4-methyl-2,3-benzoxazin-1-one, 6-[4-(2,3-difluorophenyl)-2-hydroxy-4-methyl-4-trifluoromethylcaproylamino]-4-methyl-2,3-benzoxazin-1-one is obtained. The diastereomer mixture is separated by chromatography on silica gel with 20–100% ethyl acetate/hexane.

Diastereomer 1: $^1$H-NMR (CDCl$_3$), δ (ppm)=0.66 (t, 3H), 1.39 (s, 3H), 1.7 (m, 1H), 2.1 (m, 1H), 2.61 (s, 3H), 2.7 (m, 2H), 6.9–7.2 (m, 3H), 7.67 (dd, 1H), 8.31 (d, 1H), 8.37 (d, 1H), 8.8 (s, 1H)

Diastereomer 2: $^1$H-NMR (CDCl$_3$), δ (ppm)=0.62 (t, 3H), 1.59 (s, 3H), 1.6 (m, 1H), 2.15 (m, 1H), 2.23 (d, 1H), 2.55 (s, 3H), 3.07 (d, 1H), 6.58 (m, 1H), 6.71 (m, 1H), 6.92 (m, 1H), 7.46 (dd, 1H), 8.01 (d, 1H), 8.27 (d, 1h), 8.3 (s, 1H)

EXAMPLE 27

6-[4-(2,6-Difluorophenyl)-2-hydroxy-4-methyl-4-trifluoromethylcaproylamino]-4-methyl-2,3-benzoxazin-1-one Precursors 2-(2,6-Difluorophenyl)-2-methylbutyraldehyde

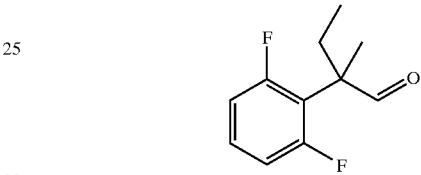

Analogously to the process that is described for 2-(5-fluoro-2-methylphenyl)-2-methylpropionaldehyde, 2-(2,6-difluorophenyl)-2-methylbutyronitrile is obtained as a colorless oil.

$^1$H-NMR (CDCl$_3$), δ (ppm)=0.83 (t, 3H), 1.49 (t, 3H), 1.9–2.1 (m, 2H), 6.85–6.95 (m, 2H), 7.2–7.3 (m, 1H), 9.69 (t, 1H).

4-(2,6-Difluorophenyl)-4-methyl-2-oxocaproic acid

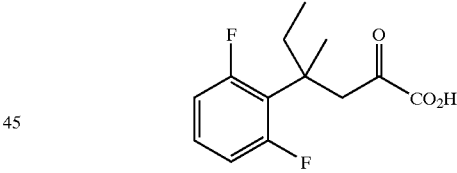

Analogously to the process that is described for 4-(5-fluoro-2-methylphenyl)-4-methyl-2-oxovaleric acid, 4-(2,6-difluorophenyl)-4-methyl-2-oxocaproic acid is obtained:
$^1$H-NMR (CDCl$_3$), δ (ppm)=0.76 (t, 3H), 1.62 (t, 3H), 1.7 (m, H), 1.9 (m, 1H) 3.0 (dt, 1H), 4.0 (d, 1H), 6.8 (m, 2H), 7.13 (m, 1H).

6-[4-(2,6-Difluorophenyl)-4-methyl-2-oxocaproylamino]-4-methyl-2,3-benzoxazin-1-one

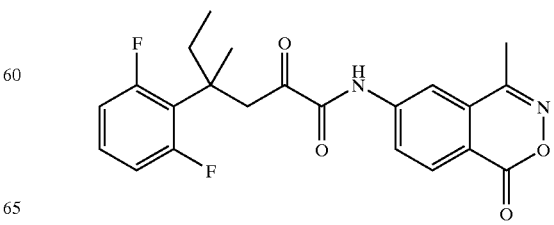

Analogously to the process that is described for 6-[4-(5-fluoro-2-methylphenyl)-4-methyl-2-oxovaleroylamino]-4-methyl-2,3-benzoxazin-1-one, 6-[4-(2,6-difluorophenyl)-4-methyl-2-oxocaproylamino]-4-methyl-2,3-benzoxazin-1-one is obtained:

$^1$H-NMR (CDCl$_3$), δ (ppm)=0.81 (t, 3H), 1.64 (t, 3H), 1.77 (m, 1H), 1.96 (m, 1H), 2.5 (s, 3H), 3.12 (dt, 1H), 4.09 (d, 1H), 6.8 (m, 2H), 7.15 (m, 1H), 7.77 (dd, 1H), 8.30 (d, 1H), 8.34 (d, 1H), 9.1 (bs, 1H).

6-[4-(2,6-Difluorophenyl)-2-hydroxy-4-methyl-4-trifluoromethylcaproylamino]-4-methyl-2,3-benzoxazin-1-one

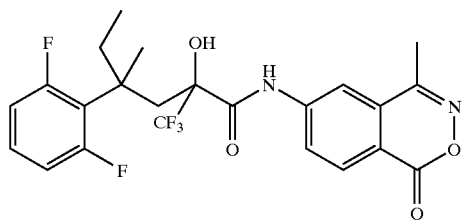

Analogously to the process that is described for 6-[4-(5-fluoro-2-methylphenyl)-2-hydroxy-4-methyl-2-trifluoromethylvaleroylamino]-4-methyl-2,3-benzoxazin-1-one, 6-[4-(2,6-difluorophenyl)-2-hydroxy-4-methyl-4-trifluoromethylcaproylamino]-4-methyl-2,3-benzoxazin-1-one is obtained as a diastereomer mixture: $^1$H-NMR (CDCl$_3$), δ (ppm)=0.7 (m, 3H), 1.4 (m, 1H), 1.5, 1.7, (2t, 3H), 2.0–3.2 (m, 6H), 6.4–7.3 (m, 3H), 7.4–8.4 (m, 3H), 8.5, 8.9 (2bs, 1H).

EXAMPLE 28

6-{3-[4-(2-Chloro-5-fluorophenyl)-tetrahydropyran-4-yl]-2-hydroxy-2-trifluoromethylpropionylamino}-4-methyl-2,3-benzoxazin-1-one Precursors 4-(2-Chloro-5-fluorophenyl)-tetrahydropyran-4-carbonitrile 6.76 g of (2-chloro-5-fluorophenyl)-acetonitrile and 5.7 ml of 2,2-dichlorodiethyl ether are dissolved in 100 ml of dimethylformamide and mixed within 2.5 hours with 3.7 g of sodium hydride (60%) while being cooled with ice. After 3 hours at 0° C. and 16 hours at room temperature, it is mixed with ice water and ethyl acetate, acidified with 1 M hydrochloric acid, and the ethyl acetate phase is washed with water, dried (Na$_2$SO$_4$) and concentrated by evaporation. After chromatography on silica gel, 6.2 g of 4-(2-chloro-5-fluorophenyl)-4-pyranylcarbonitrile, flash point 91–93° C., is obtained.

4-(2-Chloro-5-fluorophenyl)-tetrahydropyran-4-carbaldehyde

Analogously to the process that is described for 2-(5-fluoro-2-methylphenyl)-2-methylpropionaldehyde, 4-(2-chloro-5-fluorophenyl)-tetrahydropyran-4-carbaldehyde is obtained as a colorless oil, boiling point 145° C./0.04 hPa.

3-[4-(2-Chloro-5-fluorophenyl)-tetrahydropyran-4-yl]-2-oxopropionic acid

Analogously to the process that is described for 4-(5-fluoro-2-methylphenyl)-4-methyl-oxavaleric acid, 3-[4-(2-chloro-5-fluorophenyl)-tetrahydropyran-4-yl]-2-oxo-propionic acid is obtained, flash point 158° C.

6-{3-[4-(2-Chloro-5-fluorophenyl)-tetrahydropyran-4-yl]-2-oxopropionylamino}-4-methyl-2,3-benzoxazin-1-one Analogously to the process that is described for 6-[4-(5-fluoro-2-methylphenyl)-4-methyl-2-oxovaleroylamino]-4-methyl-2,3-benzoxazin-1-one, 6-{3-[4-(2-chloro-5-fluorophenyl)-tetrahydropyran-4-yl]-2-oxopropionylamino}-4-methyl-2,3-benzoxazin-1-one is synthesized. Flash point 206–208° C.

6-{3-[4-(2-Chloro-5-fluorophenyl)-tetrahydropyran-4-yl]-2-hydroxy-2-trifluoromethylpropionylamino}-4-methyl-2,3-benzoxazin-1-one

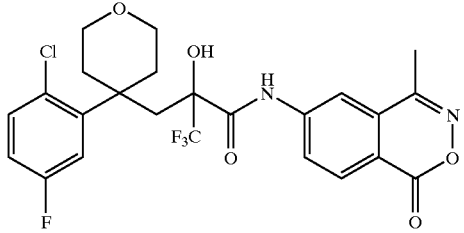

Analogously to the process that is described for 6-[4-(5-fluoro-2-methylphenyl)-2-hydroxy-4-methyl-2-trifluoromethyl-valeroylamino]-4-methyl-2,3-benzoxazin-1-one, 6-{3-[4-(2-chloro-5-fluorophenyl)-tetrahydropyran-4-yl]-2-hydroxy-2-trifluoro-methylpropionylamino}-4-methyl-2,3-benzoxazin-1-one is synthesized. Flash point 224–226° C.

Separation of Enantiomers of Example 28

The enantiomer mixture of Example 28 is separated by chromatography on chiral support medium (CHIRALPAK AD$^{(R)}$, DAICEL Company) with hexane/ethanol (9:1, vv). Thus obtained from 300 mg of racemate are:

(−)-6-{3-[4-(2-Chloro-5-fluorophenyl)-tetrahydropyran-4-yl]-2-hydroxy-2-trifluoromethylpropionylamino}-4-methyl-2,3-benzoxazin-1-one as a first fraction, 129 mg, flash point 181–183° C., [α$_D$=−83.20° (c=0.5 in tetrahydrofuran)] and (+)-6-{3-[4-(2-Chloro-5-fluorophenyl)-tetrahydropyran-4-yl]-2-hydroxy-2-trifluoromethylpropionylamino}-4-methyl-2,3-benzoxazin-1-one as a second fraction, 129 mg, flash point 181–183° C.

EXAMPLE 29

In the glucocorticoid receptor-(GR)-binding test with use of cytosol preparations of Sf9 cells that have been infected with recombinant baculoviruses, which code for the GR, and with use of 10 nM of [$^3$H]-dexamethasone as a reference substance, (cf. Lefebvre et al. J. Steroid Biochem., 33, 557–563, 1989), the compounds of formula 1 show a high to very high affinity to the GR (see Table 9).

TABLE 9

| GR-Binding Test** | |
|---|---|
| Compound | IC$_{50}$ [mol/l] |
| Example 38 | <3.0 × 10$^{-10}$ |
| Example 16, compound 26 | 1.6 × 10$^{-8}$ |
| Example 16, compound 33 | 1.1 × 10$^{-9}$ |
| Example 3, compound 9 | <3.0 × 10$^{-10}$ |
| Example 16, compound 16 | 6.2 × 10$^{-10}$ |
| Example 16, compound 13 | <3.0 × 10$^{-10}$ |
| Dexamethasone | 2.8 × 10$^{-8}$ |
| Prednisolone | 4.0 × 10$^{-8}$ |

EXAMPLE 30

The potency of the antiinflammatory action is determined in a cell test by the inhibition of the secretion of cytokine IL-8. The compounds of general formula I according to the invention inhibit the secretion of cytokine IL-8 in the human monocyte cell line THP-1 that is triggered by lipopolysaccharide (LPS). The concentration of the cytokines was determined in the supernatant by means of commercially available ELISA kits. In this connection, the compounds of formula 1 show a high to very high potency and action in inhibition (see Table 10).

TABLE 10

IL-8 Values

| Compounds | Inhibition of IL-8 Secretion IC50 [mol/l] | Inhibition of IL-8 Secretion Effectiveness [%] |
|---|---|---|
| Example 38 | $8.6 \times 10^{-9}$ | 56 |
| Example 16, compound 26 | $4.3 \times 10^{-9}$ | 77 |
| Example 16, compound 33 | $3.0 \times 10^{-8}$ | 45 |
| Example 3, compound 9 | $6.5 \times 10^{-8}$ | 51 |
| Example 16, compound 16 | $1.0 \times 10^{-8}$ | 80 |
| Example 16, compound 13 | $9.6 \times 10^{-9}$ | 58 |
| Prednisolone | $2.4 \times 10^{-8}$ | 95 |

EXAMPLE 31

The antiinflammatory actions of the compounds of general formula I were tested in the animal experiment in the croton oil-induced inflammation in rats and mice (J. Exp. Med. (1995), 182, 99–108). In this respect, croton oil in an ethanolic solution was administered topically to the ears in the animals. The test substances were systemically administered two hours before the croton oil. After 16–24 hours, the ear weight was measured as a yardstick of the inflammatory edema. In this connection, the compounds of general formula I show an inhibition of the croton-oil-induced inflammation that is comparable to the standard (prednisolone) and is sometimes also stronger (see Table 11).

TABLE 11

Inhibition of Edema Formation

| Compounds | Edema inhibition [%] with 3 mg/kg | Edema inhibition [%] with 30 mg/kg |
|---|---|---|
| Example 38 | 58 | 101 |
| Example 16, compound 26 | 11 | 81 |
| Example 16, compound 33 | 77 | 86 |
| Example 3, compound 9 | 50 | 92 |
| Example 16, compound 16 | 54 | 78 |
| Example 16, compound 13 | 47 | 106 |
| Prednisolone | 35 | 84 |

EXAMPLE 32

As a parameter for the side effects of the steroid-induced catabolic metabolism, the activity of the enzyme tyrosinamino transferase (TAT) was determined from liver homogenates by photometry. The activity represents a good yardstick of the undesirable metabolic actions of the glucocorticoids. To measure the TAT induction, the animals are sacrificed 8 hours after the test substances are administered, the livers are removed, and the TAT activity in the homogenate is measured. In this test, at doses at which they have an antiinflammatory action, the compounds of general formula I induce little or no tyrosinamino transferase in comparison to the steroids (Table 12).

TABLE 12

Induction of the Tyrosinamino Transferase Activity

| Compounds | Induction factor* for TAT with 3 mg/kg | Induction factor* for TAT with 30 mg/kg |
|---|---|---|
| Example 38 | 1.2 | 6.0 |
| Example 16, compound 26 | 1.4 | 3.7 |
| Example 16, compound 16 | 1.3 | 2.0 |
| Prednisolone | 2.6 | 8.0 |

*The induction factor stands for the corresponding n-fold increase in the tyrosinamino transferase enzyme activity in treated animals compared to untreated animals.

It is claimed:
1. A method for treating inflammation in a patient comprising administering a therapeutically effective amount of a compound of formula I or a physiologically compatible salt thereof to said patient

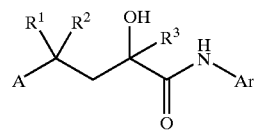

I in which
$R^1$ and $R^2$ are the same or different and stand for a hydrogen atom, a $C_1$–$C_5$ alkyl group, or, together with the C-atom of the chain, stand for a ring with a total of 3–7 links,
$R^3$ stands for a straight-chain or branched $C_1$–$C_5$ alkyl group or a straight-chain or branched, partially or completely fluorinated $C_1$–$C_5$ alkyl group,
A stands for the group

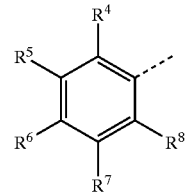

(the dashed line means the interface site), in which
$R^4$ to $R^8$ are the same or different from one another and mean a hydrogen atom, a halogen atom, a cyano group, a nitro group, a $COOR^9$ group
whereby $R^9$ stands for a hydrogen atom, a straight-chain or branched $C_1$–$C_5$ alkyl group or a benzyl group,
a $CONR^{10}$ group,
whereby $R^{10}$ stands for a hydrogen atom or a straight-chain or branched $C_1$–$C_5$ alkyl group,
an $NHR^{11}$ group,
whereby $R^{11}$ stands for a hydrogen atom, a straight-chain or branched $C_1$–$C_5$ alkyl group, a straight-chain or branched, partially or completely fluorinated $C_1$–$C_5$ alkyl group, a $C_1$–$C_5$ acyl group, an —$SO_2$—($C_1$–$C_5$) alkyl group or an —$SO_2$-phenyl group that is optionally substituted by halogen or a $C_1$–$C_5$ alkyl group, a straight-chain or branched $C_1$–$C_5$ alkyl group, a straight-chain or branched $C_2$–$C_5$ alkenyl group, a straight-chain or branched $C_2$–$C_5$ alkinyl group, a straight-chain or branched $C_1$–$C_5$ alkyl group that is partially or completely substituted by fluorine atoms, a $C_1$–$C_5$ acyl group, an aryl radical or a heteroaryl radical, or $R^4$ and $R^5$ together with the two carbon atoms of ring A mean a saturated or unsaturated carbocyclic ring with a total of 5–7 links, Ar stands for a ring system, selected from the group of general partial formula 1 or 2,

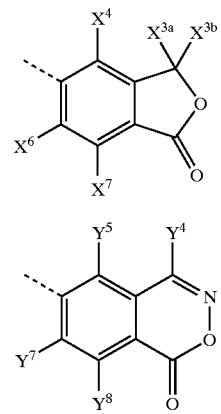

in which
radicals $X^{3a}$, $X^{3b}$, $X^4$, $X^6$, $X^7$ (in partial formula 1) and $Y^4$,
$Y^5$, $Y^7$, and $Y^8$ (in partial formula 2) are the same or different and mean a hydrogen atom, a straight-chain or branched $C_1$–$C_5$ alkyl group, or a straight-chain or branched, partially or completely fluorinated $C_1$–$C_5$ alkyl group,
radicals $X^4$, $X^6$, $X^7$ (in partial formula 1) or $Y^5$, $Y^7$, $Y^8$ (in partial formula 2) in addition are the same or different and mean a hydrogen atom, a halogen atom, a hydroxy group, a $C_1$–$C_5$ alkoxy group or a $C_1$–$C_5$ alkanoyloxy group,
as well as their racemates or separately present stereoisomers.

2. A method for treating an inflammatory, allergic or proliferative process in a patient comprising administering to said patient a therapeutically effective amount of a compound of formula I

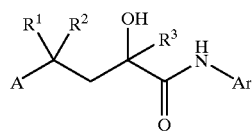

I in which
$R^1$ and $R^2$ are the same or different and stand for a hydrogen atom, a $C_1$–$C_5$ alkyl group, or, together with the C-atom of the chain, stand for a ring with a total of 3–7 links, $R^3$ stands for a straight-chain or branched $C_1$–$C_5$ alkyl group or a straight-chain or branched, partially or completely fluorinated $C_1$–$C_5$ alkyl group, A stands for the group

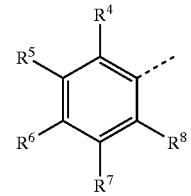

(the dashed line means the interface site), in which
$R^4$ to $R^8$ are the same or different from one another and mean a hydrogen atom, a halogen atom, a cyano group, a nitro group, a $COOR^9$ group whereby $R^9$ stands for a hydrogen atom, a straight-chain or branched $C_1$–$C_5$ alkyl group or a benzyl group,
a $CONR^{10}$ group, whereby $R^{10}$ stands for a hydrogen atom or a straight-chain or branched $C_1$–$C_5$ alkyl group,
an $NHR^{11}$ group, whereby $R^{11}$ stands for a hydrogen atom, a straight-chain or branched $C_1$–$C_5$ alkyl group, a straight-chain or branched, partially or completely fluorinated $C_1$–$C_5$ alkyl group, a $C_1$–$C_5$ acyl group, an —$SO_2$—($C_1$–$C_5$) alkyl group or an —$SO_2$-phenyl group that is optionally substituted by halogen or a $C_1$–$C_5$ alkyl group,
a straight-chain or branched $C_1$–$C_5$ alkyl group, a straight-chain or branched $C_2$–$C_5$ alkenyl group, a straight-chain or branched $C_2$–$C_5$ alkinyl group, a straight-chain or branched $C_1$–$C_5$ alkyl group that is partially or completely substituted by fluorine atoms, a $C_1$–$C_5$ acyl group, an aryl radical or a heteroaryl radical, or $R^4$ and $R^5$ together with the two carbon atoms of ring A mean a saturated or unsaturated carbocyclic ring with a total of 5–7 links, Ar stands for a ring system, selected from the group of general partial formula 1 or 2,

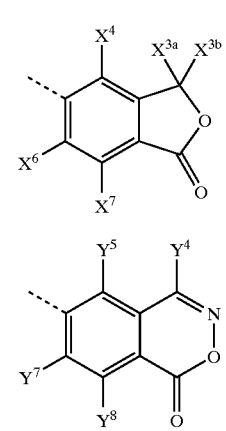

in which
radicals $X^{3a}$, $X^{3b}$, $X^4$, $X^6$, $X^7$ (in partial formula 1) and $Y^4$, $Y^5$, $Y^7$, and $Y^8$ (in partial formula 2) are the same or different and mean a hydrogen atom, a straight-chain or branched $C_1$–$C_5$ alkyl group, or a straight-chain or branched, partially or completely fluorinated $C_1$–$C_5$ alkyl group, radicals X⁴, X⁶, X⁷ (in partial formula 1) or Y⁵, Y⁷, Y⁸ (in partial formula 2) in addition are the same or different and mean a hydrogen atom, a halogen atom, a hydroxy group, a $C_1$–$C_5$ alkoxy group or a $C_1$–$C_5$ alkanoyloxy group, as well as their racemates or separately present stereoisomers, and wherein said process is a lung disease, rheumatic disease, auto-immune disease, degenerative joint disease, allergy, vascular disease, dermatological disease, nephropathy, liver disease, gastrointestinal disease, proctological disease, eye disease, disease of the ear-nose-throat, neurological disease, blood disease, tumor disease, endocrine disease, transplant, severe shock condition, vomiting, substitution therapy with suprarenal insufficiency, or pain with inflammatory origins.

3. A method according to claim 1, wherein said compound is

6-[4-(5-Fluoro-2-methylphenyl)-2-hydroxy-4-methyl-2trifluoromethylvaleroylamino]-4-methyl-2,3-benzoxazin-1-one 5-[4-(5-fluoro-2-methylphenyl)-2-hydroxy-4-methyl-2-trifluoromethylvaleroylamino]-phthalide 6-[4-(2-chloro-5-fluorophenyl)-2-hydroxy-4-methyl-2-trifluoromethylvaleroylamino]-4-methyl-2,3-benzoxazin-1-one 5-[4-(5-fluoro-2-nitrophenyl)-2-hydroxy-4-methyl-2-trifluoromethylvaleroylamino]-phthalide 6-[4-(5-fluoro-2-nitrophenyl)-2-hydroxy-4-methyl-2-trifluoromethylvaleroylamino]-4-methyl-2,3-benzoxazin-1-one 5-[4-(3-fluoro-4-nitrophenyl)-2-hydroxy-4-methyl-2-trifluoromethylvaleroylamino]-phthalide 6-[4-(3-fluoro4-nitrophenyl)-2-hydroxy-4-methyl-2-trifluoromethylvaleroylamino]-4-methyl-2,3-benzoxazin-1-one 6-[4-(2-bromo-5-fluorophenyl)-2-hydroxy-4-methyl-2-trifluoromethylvaleroylamino]-4-methyl-2,3-benzoxazin-1-one 6-[4-(indan-4'-yl)-2hydroxy-4methyl-2-trifluromethylvaleroylamino]-4-methyl-2,3-benzoxazin-1-one (−) 6-[4-(indan-4'-yl)-2-hydroxy-4-methyl-2-trifluoromethylvaleroylamino]-4-methyl-2,3-benzoxazin-1-one (+) 6-[4-(indan-4'-yl)-2-hydroxy-4-methyl-2-trifluoromethylvaleroylamino]-4-methyl-2,3-benzoxazin-1-one 6-[4-(5-fluoro-2-vinylphenyl)-2-hydroxy-4-methyl-2-trifluoromethylvaleroylamino]-4-methyl-2,3-benzoxazin-1-one (−) 6-[4-(5-fluoro-2-vinylphenyl)-2-hydroxy-4-methyl-2-trifluoromethylvaleroylamino]-4-methyl-2,3-benzoxazin-1-one (+) 6-[4-(5-fluoro-2-vinylphenyl)-2-hydroxy-4-methyl-2-trifluoromethylvaleroylamino]-4-methyl-2,3-benzoxazin-1-one 6-[2-hydroxy-4-methyl-2-trifluorometbyl-4-(4-trifluoromethylphenyl)-valeroylamino]-4-methyl-2,3-benzoxazin-1-one (−) 6-[2-hydroxy-4-methyl-2-trifluoromethyl-4-(4-trifluoromethylphenyl)-valeroylamino]-4-methyl-2,3-benzoxazin-1-one (+) 6-[2-hydroxy-4-methyl-2-trifluoromethyl-4-(4-trifluoromethylphenyl)-valeroylamino]-4-methyl-2,3-benzoxazin-1-one 6-[4-(2-bromo-3,5-difluorophenyl)-2-hydroxy-4-methyl-2-trifluoromethylvaleroylamino]-4-methyl-2,3-benzoxazin-1-one (−) 6-[4-(2-bromo-3,5-difluorophenyl)-2-hydroxy-4-methyl-2-trifluoromethylvaleroylamino]-4-methyl-2,3-benzoxazin-1-one (+) 6-[4-(2-bromo-3,5-difluorophenyl)-2-hydroxy-4-methyl-2-trifluoromethylvaleroylamino]-4-methyl-2,3-benzoxazin-1-one 6-[4-(3,5-difluorophenyl)-2-hydroxy-4-methyl-2-trifluoromethylvaleroylamino]-4-methyl-2,3-benzoxazin-1-one (−) 6-[4-(3,5-difluorophenyl)-2-hydroxy-4-methyl-2-trifluoromethylvaleroylamino]-4-methyl-2,3-benzoxazin-1-one (+) 6-[4-(3,5-difluorophenyl)-2-hydroxy-4-methyl-2-trifluoromethylvaleroylamino]-4-methyl-2,3-benzoxazin-1-one 6-[4-(2-cyano-5-fluorophenyl)-2-hydroxy-4-methyl-2-trifluoromethylvaleroylamino]-4-methyl-2,3-benzoxazin-1-one 6-[4-(2-ethenyl-5-fluorophenyl)-2-hydroxy-4-methyl-2-trifluoromethylvaleroylamino]-4-methyl-2,3-benzoxazin-1-one 6-[4-(2-ethyl-5-fluorophenyl)-2-hydroxy-4-methyl-2-trifluoromethylvaleroylamino]-4-methyl-2,3-benzoxazin-1-one 6-[4-(5-fluoro-2-phenylphenyl)-2-hydroxy-4-methyl-2-trifluoromethylvaleroylamino]-4-methyl-2,3-benzoxazin-1-one 6-[4-{5-fluoro-2-(furan-2'-yl)phenyl}-2-hydroxy-4-methyl-2-trifluoromethylvaleroylamino]-4-methyl-2,3-benzoxazin-1-one 6-[4-(2-bromo-3,5-difluorophenyl)-2-hydroxy-4-methyl-2-trifluoromethylvaleroylamino]-4-methyl-2,3-benzoxazin-1-one 6-[2-hydroxy-4-methyl-2-trifluoromethyl-4-(1-naphthyl)-valeroylamino]-4-methyl-2,3-benzoxazin-1-one (−) 6-[2-hydroxy-4-methyl-2-trifluoromethyl-4-(1-naphthyl)-valeroylamino]-4-methyl-2,3-benzoxazin-1-one (+) 6-[2-hydroxy-4-methyl-2-trifluoromethyl-4-(1-naphthyl)-valeroylamino]-4-methyl-2,3-benzoxazin-1-one 6-[4-(2-chlorophenyl)-2-hydroxy-4-methyl-2-trifluoromethylvaleroyl]-amino-4-methyl-2,3-benzoxazin-1-one (−)-6-[4-(2-chlorophenyl)-2-hydroxy-4-methyl-2-trifluoromethylvaleroyl]-amino-4-methyl-2,3-benzoxazin-1-one (+)-6-[4-(2-chlorophenyl)-2-hydroxy-4-methyl-2-trifluoromethylvaleroyl]-amino-4-metbyl-2,3-benzoxazin-1-one 6-[4-(2-chloro-3-fluoro-phenyl)-2-hydroxy-4-methyl-2-trifluoromethylvaleroy]-amino-4-methyl-2,3-benzoxazin-1-one (−)-6-[4-(2-chloro-3-fluoro-phenyl)-2-hydroxy-4-metbyl-2-trifluoromethylvaleroyl]-amino-4-methyl-2,3-benzoxazin-1-one (+)-6-[4-(2-chloro-3-fluoro-phenyl)-2-hydroxy-4-methyl-2-trifluoromethylvaleroyl]-amino-4-methyl-2,3-benzoxazin-1-one 6-[4-(2-chloro-4-fluoro-phenyl)-2-hydroxy-4-methyl-2-trifluoromethylvaleroyl]-amino-4-methyl-2,3-benzoxazin-1-one (−)-6-[4-(2-chloro-4-fluoro-phenyl)-2-hydroxy-4-methyl-2-trifluoromethylvaleroyl]-amino-4-methyl-2,3-benzoxazin-1-one (+)-6-[4-(2-chloro-4-fluoro-phenyl)-2-hydroxy-4-methyl-2-trifluoromethylvaleroyl]-amino-4-methyl-2,3-benzoxazin-1-one 6-[4-(2-chloro-6-fluoro-phenyl)-2-hydroxy-4-methyl-2-trifluoromethylvaleroyl]-amino-4-methyl-2,3-benzoxazin-1-one (−)-6-[4-(2-chloro-6-fluoro-phenyl-2-hydroxy-4-methyl-2-trifluoromethylvaleroyl]-amino-4-methyl-2,3-benzoxazin-1-one (+)-6-[4-(2-chloro-6-fluoro-phenyl)-2-hydroxy-4-methyl-2-trifluoromethylvaleroyl]-amino-4-methyl-2,3-benzoxazin-1-one 6-[4-(2,3-dichlorophenyl)-2-hydroxy-4-methyl-2-trifluoromethylvaleroyl]-amino-4-methyl-2,3-benzoxazin-1-one (−)-6-[4-(2,3-dichlorophenyl)-2-hydroxy-4-methyl-2-trifluoromethylvaleroyl]-amino-4-methyl-2,3-benzoxazin-1-one (+)-6-[4-(2,3-dichlorophenyl)-2-hydroxy-4-methyl-2-trifluoromethylvaleroyl]-amino-4-methyl-2,3-benzoxazin-1-one 6-[4-(2,4-dichloropheny)-2-hydroxy-4-methyl-2-trifluoromethylvaleroyl]-amino-4-methyl-2,3-benzoxazin-1-one (−)-6-[4-(2,4-dichlorophenyl)-2-hydroxy-4-methyl-2-trifluoromethylvaleroyl]-amino-4-methyl-2,3-benzoxazin-1-one (+)-6-[4-(2,4-dichlorophenyl)-2-hydroxy-4-methyl-2-trifluoromethylvaleroyl]-amino-4-methyl-2,3-benzoxazin-1-one 6-[4(2,5-dichlorophenyl)-2-hydroxy-4-methyl-2trifluoromethylvaleroyl]-amino-4-methyl-2,3-benzoxazin-1-one (−)-6-[4(2,5-dichlorophenyl)-2-hydroxy-4-methyl-2-trifluoromethylvaleroyl]-amino-4-methyl-4methyl-2,3-benzoxazin-1-one (+)-6-[4-(2,5-dichlorophenyl)-2-hydroxy-2-trifluoromethylvaleroyl]-amino-4-methyl-2,3-benzoxazin-1one 6-[4-(4-bromo-2-chlorophenyl)-2-hydroxy-4-methyl-2-trifluoromethylvaleroyl]-amino-4-methyl-2,3-benzoxazin-1-one (−)-6-[4-(4-bromo-2-chlorophenyl)-2-hydroxy-4-methyl-2-trifluoromethylvaleroyl]-amino-4-methyl-2,3-benzoxazin-1-one (+)-6-[4-(4-bromo-2-chlorophenyl)-2-hydroxy-4-methyl-2-trifluoromethylvaleroyl]-amino-4-methyl-2,3-benzoxazin-1-one 6-[4-(2-chloro-3-methoxyphenyl)-2-hydroxy-4-methyl-2-trifluoromethylvaleroyl]-amino-4-methyl-2,3-benzoxazin-1-one (−)-6-[4-(2-chloro-3-methoxyphenyl)-2-hydroxy-4-methyl-2-trifluoromethylvaleroyl]-amino-4-methyl-2,3-benzoxazin-1-one (+)-6-[4-(2-chloro-3-methoxyphenyl)-2-hydroxy-4-methyl-2-trifluoromethylvaleroyl]-amino-4-methyl-2,3-benzoxazin-1-one 6-[4-(2-chloro-3-hydroxyphenyl)-2-hydroxy-4-methyl-2-trifluoromethylvaleroyl]-amino-4-methyl-2,3-benzoxazin-1-one (−)-6-[4-(2-chloro-3-hydroxyphenyl)-2-hydroxy-4-methyl-2-trifluoromethylvaleroyl]-amino-4-methyl-2,3-benzoxazin-1-one (+)-6-[4-(2-chloro-3-hydroxyphenyl)-2-hydroxy-4-methyl-2-trifluoromethylvaleroyl]-amino-4-methyl-2,3-benzoxazin-1-one 6-[4-(2-fluorophenyl)-2-hydroxy-4-methyl-2-trifluoromethylvaleroylamino]-4-methyl-2,3-benzoxazin-1-one (−)-6-[4-(2-fluorophenyl)-2-hydroxy-4-methyl-2-trifluoromethylvaleroylamino]-4-methyl-2,3-benzoxazin-1-one (+)-6-[4-(2-fluorophenyl)-2-hydroxy-4-methyl-2-trifluoromethylvaleroylamino]-4-methyl-2,3-benzoxazin-1-one 6-[4-(2,3-difluorophenyl)-2-hydroxy-4-nietliyl-2-trifluoromethylvaleroylamino]-4-methyl-2,3-benzoxazin-1-one (−)-6-[4-(2,3-difluorophenyl)-2-hydroxy-4-methyl-2-trifluoromethylvaleroylamino]-4-methyl-2,3-benzoxazin-1-one (+)-6-[4-(2,3-difluorophenyl)-2-hydroxy-4-methyl-2-trifluoromethylvaleroylamino]-4-methyl-2,3-benzoxazin-1-one (−)-6-[4-(2,3-difluorophenyl)-2-hydroxy-4-methyl-2-trifluoromethylhexanoylamino]-4-methyl-2,3-benzoxazin-1-one (+)-6-[4-(2,3-difluorophenyl)-2-hydroxy-4-methyl-2-trifluoromethylhexanoylamino]-4-methyl-2,3-benzoxazin-1-one 6-[4-(2,4-difluorophenyl)-2-hydroxy-4-methyl-2-trifluoromethylvaleroylamino]-4-methyl-2,3-benzoxazin-1-one (−)-6-[4-(2,4-difluorophenyl)-2-hydroxy-4-methyl-2-trifluoromethylvaleroylamino]-4-methyl-2,3-benzoxazin-1-one (+)-6-[4-(2,4-difluorophenyl)-2-hydroxy-4-methyl-2-trifluoromethylvaleroylamino]-4-methyl-2,3-benzoxazin-1-one 6-[4-(2,5-difluorophenyl)-2-hydroxy-4-methyl-2-trifluoromethylvaleroylamino]-4-methyl-2,3-benzoxazin-1-one (−)-6-[4-(2,5-difluorophenyl)-2-hydroxy-4-methyl-2-trifluoromethylvaleroylamino]-4-methyl-2,3-benzoxazin-1-one (+)-6-[4-(2,5-difluorophenyl)-2-hydroxy-4-methyl-2-trifluoromethylvaleroylamino]-4-methyl-2,3-benzoxazin-1-one 6-[4-(2,6-difluorophenyl)-2-hydroxy-4-methyl-2-trifluoromethylvaleroylamino]-4-methyl-2,3-benzoxazin-1-one (−)-6-[4-(2,6-difluorophenyl)-2-hydroxy-4-methyl-2-trifluoromethylvaleroylamino]-4-methyl-2,3-benzoxazin-1-one (+)-6-[4-(2,6-difluorophenyl)-2-hydroxy-4-methyl-2-trifluoromethylvaleroylamino]-4-methyl-2,3-benzoxazin-1-one 6-[4-(2,3,5-trifluorophenyl)-2-hydroxy-4-methyl-2-trifluoromethylvaleroylamino]-4-methyl-2,3-benzoxazin-1-one (−)-6-[4-(2,3,5-trifluorophenyl)-2-hydroxy-4-methyl-2-trifluoromethylvaleroylamino]-4-methyl-2,3-benzoxazin-1-one (+)-6-[4-(2,3,5-trifluorophenyl)-2-hydroxy-4-methyl-2-trifluoromethylvaleroylamino]-4-methyl-2,3-benzoxazin-1-one 6-[4-(2,3,4-trifluorophenyl)-2-hydroxy-4-methyl-2-trifluoromethylvaleroylamino]-4-methyl-2,3-benzoxazin-1-one (−)-6-[4-(2,3,4-trifluorophenyl)-2-hydroxy-4-methyl-2-trifluoromethylvaleroylamino]-4-methyl-2,3-benzoxazin-1-one (+)-6-[4-(2,3,4-trifluorophenyl)-2-hydroxy-4-methyl-2-trifluoromethylvaleroylamino]-4-methyl-2,3-benzoxazin-1-one 6-[4-(3-chloro-2-fluorophenyl)-2-hydroxy-4-methyl-2-trifluoromethylvaleroylamino]-4-methyl-2,3-benzoxazin-1-one (−)-6-[4-(3-chloro-2-fluorophenyl)-2-hydroxy-4-methyl-2-trifluoromethylvaleroyl-amino]-4-methyl-2,3-benzoxazin-1-one (+)-6-[4-(3-chloro-2-fluorophenyl)-2-hydroxy-4-methyl-2-trifluoromethylvaleroylamino]-4-methyl-2,3-benzoxazin-1-one 6-[4-(4-chloro-2-fluorophenyl)-2-hydroxy-4-methyl-2-trifluoromethylvaleroylamino]-4-methyl-2,3-benzoxazin-1-one (−)-6-[4-(4-chloro-2-fluorophenyl)-2-hydroxy-4-methyl-2-trifluoromethylvaleroyl-amino]-4-methyl-2,3-benzoxazin-1-one (+)-6-[4-(4-chloro-2-fluorophenyl)-2-hydroxy-4-methyl-2-trifluoromethylvaleroyl-amino]-4-methyl-2,3-benzoxazin-1-one 6-[4-(2-fluoro-3-methoxyphenyl)-2-hydroxy-4-methyl-2-trifluoromethylvaleroylamino]-4-methyl-2,3-benzoxazin-1-one (−) 6-[4-(2-fluoro-3-methoxyphenyl)-2-hydroxy-4-methyl-2-trifluoromethylvaleroyl-amino]-4-methyl-2,3-benzoxazin-1-one (+) 6-[4-(2-fluoro-3-methoxyphenyl)-2-hydroxy-4-methyl-2-trifluoromethylvaleroylamino]-4-methyl-2,3-benzoxazin-1-one 6-[4-(2-bromophenyl)-2-hydroxy-4-methyl-2-trifluoromethylvaleroylamino]-4-methyl-2,3-benzoxazin-1-one (−)-6-[4-(2-bromophenyl)-2-hydroxy-4-methyl-2-trifluoromethylvaleroylamino]-4-methyl-2,3-benzoxazin-1-one (+)-6-[4-(2-bromophenyl)-2-hydroxy-4-methyl-2-trifluoromethylvaleroylamino]-4-methyl-2,3-benzoxazin-1-one 6-[4-(2-trifluoromethyl-phenyl)-2-hydroxy-4-methyl-2-trifluoromethylvaleroyl]-amino-4-methyl-2,3-benzoxazin-1-one (−)-6-[4-(2-trifluoromethyl-phenyl)-2-hydroxy-4-methyl-2-trifluoromethylvaleroyl]-amino-4-methyl-2,3-benzoxazin-1-one (+)-6-[4-(2-trifluoromethyl-phenyl)-2-hydroxy-4-methyl-2-trifluoromethylvaleroyl]-amino-4-methyl-2,3-benzoxazin-1-one 6-[4-(4-fluoro-2-trifluoromethyl-phenyl)-2-hydroxy-4-methyl-2-trifluoromethylvaleroyl]-amino-4-methyl-2,3-benzoxazin-1-one (−)-6-[4-(4-fluoro-2-trifluoromethyl-phenyl)-2-hydroxy-4-methyl-2-trifluoromethyl-valeroyl]-amino-4-methyl-2,3-benzoxazin-1-one (+)-6-[4-(4-fluoro-2-trifluoromethyl-phenyl)-2-hydroxy-4-methyl-2-trifluoromethyl-valeroyl]-amino-4-methyl-2,3-benzoxazin-1-one 6-[4-(5-fluoro-2-trifluoromethyl-phenyl)-2-hydroxy-4-methyl-2-trifluoromethylvaleroyl]-amino-4-methyl-2,3-benzoxazin-1-one (−)-6-[4-(5-fluoro-2-trifluoromethyl-phenyl)-2-hydroxy-4-methyl-2-trifluoromethyl-valeroyl]-amino-4-methyl-2,3-benzoxazin-1-one (+)-6-[4-(5-fluoro-2-trifluoromethyl-phenyl)-2-hydroxy-4-methyl-2-trifluoromethyl-valeroyl]-amino-4-methyl-2,3-benzoxazin-1-one 6-[4-(5-chloro-2-trifluoromethyl-phenyl)-2-hydroxy-4-methyl-2-trifluoromethyl-valeroyl]-amino-4-methyl-2,3-benzoxazin-1-one (−)-6-[4-(5-chloro-2-trifluoromethyl-phenyl)-2-hydroxy-4-methyl-2-trifluoromethyl-valeroyl]-amino-4-methyl-2,3-benzoxazin-1-one (+)-6-[4-(5-chloro-2-trifluoromethyl-phenyl)-2-hydroxy-4-methyl-2-trifluoromethyl-valeroyl]-amino-4-methyl-2,3-benzoxazin-1-one 6-[3-{1-(2-chlorobenyl)-cyclopropyl}-2-hydroxy-2-trifluoromethylpropionyl]-amino-4-methyl-2,3-benzoxazin-1-one (−) 6-[3-{1-(2-chlorophenyl)-cyclopropyl}-2-hydroxy-2-trifluoromethylpropionyl]-amino-4-methyl-2,3-benzoxazin-1-one (+) 6-[3-{1-(2-chlorophenyl)-cyclopropyl}-2-hydroxy-2-trifluoromethylpropionyl]-amino-4-methyl-2,3-benzoxazin-1-one 6-[3-{1-(2-chlorophenyl)-cyclobutyl}-2-hydroxy-2-trifluoromethylpropionyl]-amino-4-methyl-2,3-benzoxazin-1-one (−)-6-[3-{1-(2-chlorophenyl}-cyclobutyl)-2-hydroxy-2-trifluoromethylpropionyl]-amino-4-methyl-2,3-benzoxazin-1-one (+)-6-[3-{1-(2-chlorophenyl)-cyclobutyl}-2-hydroxy-2-trifluoromethylpropionyl]-amino-4-methyl-2,3-benzoxazin-1-one 6-[3-{1-(2-chlorophenyl)-cyclopentyl}-2-hydroxy-2-trifluoromethylpropionyl]-amino-4-methyl-2,3-benzoxazin-1-one (−)-6-[3-{1-(2-chlorophenyl)-cyclopentyl}-2-hydroxy-2-trifluoromethylpropionyl]-amino-4-methyl-2,3-benzoxazin-1-one (+)-6-[3-{1-(2-chlorophenyl)-cyclopentyl}-2-hydroxy-2-trifluoromethylpropionyl]-amino-4-methyl-2,3-benzoxazin-1-one 6-[3-{1-(2-chloro-4-fluorophenyl)-cyclopropyl}-2-hydroxy-2-trifluoromethylpropionyl]-amino-4-methyl-2,3-benzoxazin-1-one (−)-6-[3-{1-(2-chloro-4-fluorophenyl)-cyclopropyl}-2-hydroxy-2-trifluromethylpropionyl]-amino-4-methyl-2,3-benzoxazin-1-one (+)-6-[3-{1-(2-chloro-4-fluorophenyl)-cyclopropyl}-2-hydroxy-2-trifluoromethylpropionylj]-amino-4-methyl-2,3-benzoxazin-1-one 6-[3-{1-(2-chloro-4-fluorophenyl)-cyclobutyl}-2-hydroxy-2-trifluoromethylpropionyl]-amino-4-methyl-2,3-benzoxazin-1-one (−)-6-[3-{1-(2-chloro-4-fluorophenyl)-cyclobutyl}-2-hydroxy-2-trifluoromethylpropionyl]-amino-4-methyl-2,3-benzoxazin-1-one (+)-6-[3-{1-(2-chloro-4-fluorophenyl)-cyclobutyl}-2-hydroxy-2-trifluoromethylpropionyl]-amino4-methyl-2,3-benzoxazin-1-one 6-[3-{1-(2-chloro-5-fluorophenyl)-cyclopropyl}-2-hydroxy-2-trifluoromethylpropionyl]-amino-4-methyl-2,3-benzoxazin-1-one (−)-6-[3-{1-(2-chloro-5-fluorophenyl)-cyclopropyl}-2-hydroxy-2-trifluoromethylpropionyl]-amino-4-methyl-2,3-benzoxazin-1-one (+)-6-[3-{1-(2-chloro-5-fluorophenyl)-cyclopropyl}-2-hydroxy-2-trifluoromethylpropionyl]-amino-4-methyl-2,3-benzoxazin-1-one 6-[3-{1-(2-chloro-5-fluorophenyl)-cyclobutyl}-2-hydroxy-2-trifluorornethylpropionyl]-amino-4-methyl-2,3-benzoxazin-1-one (−)-6-[3-{1-(2-chloro-5-fluorophenyl)-cyclobutyl}-2-hydroxy-2-trifluoromethylpropionyl]-amino-4-methyl-2,3-benzoxazin-1-one (+)-6-[3-{1-(2-chloro-5-fluorophenyl)-cyclobutyl}-2-hydroxy-2-trifluoromethylpropionyl]-amino-4-methyl-2,3-benzoxazin-1-one 6-[3-{1-(2,4-dichlorophenyl)-cyclopropyl}-2-hydroxy-2-trifluoromethylpropionyl]-amino-4-methyl-2,3-benzoxazin-1-one (−)-6-[3-{1-(2,4-dichlorophenyl)-cyclopropyl}-2-hydroxy-2-trifluoromethylpropionyl]-amino-4-methyl-2,3-benzoxazin-1-one (+)-6-[3-{1-(2,4-dichlorophenyl)-cyclopropyl}-2-hydroxy-2-trifluoromethylpropionyl]-amino-4-methyl-2,3-benzoxazin-1-one 6-[3-{1-(2,4-dichlorophenyl)-cyclobutyl}-2-hydroxy-2-trifluoromethylpropionyl]-amino-4-methyl-2,3-benzoxazin-1-one (−)-6-[3-{1-(2,4-dichlorophenyl)-cyclobutyl}-2-hydroxy-2-trifluoromethylpropionyl]-amino-4-methyl-2,3-benzoxazin-1-one (+)-6-[3-{1-(2,4-dichlorophenyl)-cyclobutyl}-2-hydroxy-2-trifluoromethylpropionyl]-amino-4-methyl-2,3-benzoxazin-1-one 6-[3-{1-(2-trifluoromethyl-phenyl)-cyclopropyl}-2-hydroxy-2-trifluoromethylpropionyl]-amino-4-metbyl-2,3-benzoxazin-1-one (−)-6-[3-{1-(2-trifluoromethyl-phenyl)-cyclopropyl}-2-hydroxy-2-trifluoromethylpropionyl]-amino-4-methyl-2,3-benzoxazin-1-one (+)-6-[3-{1-(2-trifluoromethyl-phenyl)-cyclopropyl}-2-hydroxy-2-trifluoromethylpropionyl]-amino-4-methyl-2,3-benzoxazin-1-one 6-[3-{1-(2-trifluoromethyl-phenyl)-cyclobutyl}-2-hydroxy-2-trifluoromethylpropionyl]-amino-4-methyl-2,3-benzoxazin-1-one (−)-6-[3-{1-(2-trifluoromethyl-phenyl)-cyclobutyl}-2-hydroxy-2-trifluoromethylpropionyl]-amino-4-methyl-2,3-benzoxazin-1-one (+)-6-[3-{1-(2-trifluoromethyl-phenyl)-cyclobutyl}-2-hydroxy-2-trifluoromethylpropionyl]-amino-4-methyl-2,3-benzoxazin-1-one 6-[3-{1-(2-trifluoromethyl-phenyl)-cyclohexyl}-2-hydroxy-2-trifluoromethylpropionyl]-amino-4-methyl-2,3-benzoxazin-1-one (−) 6-[3-{1-(2-trifluoromethyl-phenyl)-cyclohexyl}-2-hydroxy-2-trifluoromethylpropionyl]-amino-4-methyl-2,3-benzoxazin-1-one (+) 6-[3-{1-(2-trifluoromethyl-phenyl)-cyclohexyl}-2-hydroxy-2-trifluoromethylpropionyl]-amino-4-methyl-2,3-benzoxazin-1-one 6-[3-{1-(5-fluoro-2-trifluoromethyl-phenyl)-cyclopropyl)-2-hydroxy-2-trifluoromethylpropionyl]-amino-4-methyl-2,3-benzoxazin-1-one (−)-6-[3-{1-(5-fluoro-2-trifluoromethyl-phenyl)-cyclopropyl}-2-hydroxy-2-trifluoromethylpropionyl]-amino-4-methyl-2,3-benzoxazin-1-one (+)-6-[3-{1-(5-fluoro-2-trifluoromethyl-phenyl)-cyclopropyl}-2-hydroxy-2-triflúromethylpropionyl]-amino-4-methyl-2,3-bcnzoxazin-1-one 6-[3-{1-(5-fluoro-2-trifluoromethyl-phenyl)-cyclobutyl}-2-hydroxy-2-trifluoromethylpropionyl]-amino-4-methyl-2,3-benzoxazin-1-one (−)-6-[3-{1-(5-fluoro-2-trifluoromethyl-phenyl)-cyclobutyl}-2-hydroxy-2-trifluoromethylpropionyl]-amino-4-methyl-2,3-benzoxazin-1-one (+)-6-[3-{1-(5-fluoro-2-trifluoromethyl-phenyl)-cyclobutyl}-2-hydroxy-2-trifluoromethylpropionyl]-amino-4-methyl-2,3-benzoxazin-1-one 6-[3-{1-(2-fluorophenyl)-cyclopropyl}-2-hydroxy-2-trifluoromethylpropionylamino]-4-methyl-2,3-benzoxazin-1-one (−)-6-[3-{1-(2-fluorophenyl)-cyclopropyl}-2-hydroxy-2-trifluoromethylpropionylamino]-4-methyl-2,3-benzoxazin-1-one (+)-6-[3-{1-(2-fluorophenyl)-cyclopropyl}-2-hydroxy-2-trifluoromethylpropionylamino]-4-methyl-2,3-benzoxazin-1-one 6-[3-{1-(2-fluorophenyl)-cyclobutyl}-2-hydroxy-2-trifluoromethylpropionylamino]-4-methyl-2,3-bcnzoxazin-1-one (−)-6-[3-{1-(2-fluorophenyl)-cyclobutyl}-2-hydroxy-2-trifluoromethylpropionylamino]-4-methyl-2,3-benzoxazin-1-one (+)-6-[3-{1-(2-fluorophenyl)-cyclobutyl}-2-hydroxy-2-trifluoromethylpropionylamino]-4-methyl-2,3-benzoxazin-1-one 6-[3-{1-(2-fluorophenyl)-cyclopentyl}-2-hydroxy-2-trifluoromethylpropionylamino]-4-methyl-2,3-benzoxazin-1-one (−)-6-[3-{1-(2-fluoropbenyl)-cyclopentyl}-2-hydroxy-2-trifluoromethylpropionylamino]-4-methyl-2,3-benzoxazin-1-one (+)-6-[3-{1-(2-fluorophenyl)-cyclopentyl}-2-hydroxy-2-trifluoromethylpropionylamino]-4-methyl-2,3-benzoxazin-1-one 6-[3-{1-(2-fluorophenyl)-cyclohexyl}-2-hydroxy-2-trifluoromethylpropionylamino]-4-methyl-2,3-benzoxazin-1-one (−)-6-[3-{1-(2-fluorophenyl)-cyclohexyl}-2-hydroxy-2-trifluoromethylpropionylamino]-4-methyl-2,3-benzoxazin-1-one (+)-6-[3-{1-(2-fluorophenyl)-cyclohexyl}-2-hydroxy-2-trifluoromethylpropionylaminol-4-methyl-2,3-benzoxazin-1-one 6-[3-Δ1-(2,3-difluorophenyl)-cyclopropyl}-2-hydroxy-2-trifluoromethylpropionylamino]-4-methyl-2,3-benzoxazin-1-one (−)-6-[3-{1-(2,3-difluorophenyl)-cyclopropyl}-2-hydroxy-2-trifluoromethylpropionylamino]-4-methyl-2,3-benzoxazin-1-one (+)-6-[3-{1-(2,3-difluorophenyl)-cyclopropyl}-2-hydroxy-2-trifluoromethylpropionyl-amino]-4-methyl-2,3-benzoxazin-1-one 6-[3-{1-(2,3-difluorophenyl)-cyclobutyl}-2-hydroxy-2-trifluoromethylpropionylamino]-4-methyl-2,3-benzoxazin-1-one (−) 6-[3-{1-(2,3-difluorophenyl)-cyclobutyl}-2-hydroxy-2-trifluoromethylpropionylamino]-4-methyl-2,3-benzoxazin-1-one (+) 6-[3-{1-(2,3-difluorophenyl)-cyclobutyl}-2-hydroxy-2-trifluoromethylpropionylamino]-4-methyl-2,3-benzoxazin-1-one 6-[3-{1-(2,5-difluorophenyl)-cyclopropyl}-2-hydroxy-2-trifluoromethylpropionylamino]-4-methyl-2,3-benzoxazin-1-one (−)-6-[3-{1-(2,5-difluorophenyl)-cyclopropyl}-2-hydroxy-2-trifluoromethylpropionylamino]-4-methyl-2,3-benzoxazin-1-one (+)-6-[3-{1-(2,5-difluorophenyl)-cyclopropyl}-2-hydroxy-2-trifluoromethylpropionylamino]-4-methyl-2,3-benzoxazin-1-one 6-[3-{1-(2,3,5-trifluorophenyl)-cyclopropyl}-2-hydroxy-2-trifluoromethylpropionylamino]-4-methyl-2,3-benzoxazin-1-one (−)-6-[3-{1-(2,3,5-trifluorophenyl)-cyclopropyl}-2-hydroxy-2-trifluoromethylpropionylamino]-4-methyl-2,3-benzoxazin-1-one (+)-6-[3-{1-(2,3,5-trifluorophenyl)-cyclopropyl}-2-hydroxy-2-trifluoromethylpropionyl-amino]-4-methyl-2,3-benzoxazin-1-one 6-[3-{1-(2,3,5-trifluorophenyl)-cyclobutyl}-2-hydroxy-2-trifluoromethylpropionylamino]-4-methyl-2,3-benzoxazin-1-one (−)-6-[3-{1-(2,3,5-trifluorophenyl)-cyclobutyl}-2-hydroxy-2-trifluoromethylpropionylamino]-4-methyl-2,3-benzoxazin-1-one (+)-6-[3-{1-(2,3,5-trifluorophenyl)-cyclobutyl}-2-hydroxy-2-trifluoromethylpropionyl-amino]-4-methyl-2,3-benzoxazin-1-one 6-[3-{1-(2-bromophenyl)-cyclopropyl}-2-hydroxy-2-trifluoromethylpropionylamino]-4-methyl-2,3-benzoxazin-1-one (−)-6-[3-{1-(2-bromophenyl)-cyclopropyl}-2-hydroxy-2-trifluoromethylpropionylamino]-4-methyl-2,3-benzoxazin-1-one (+)-6-[3-{1-(2-bromophenyl)-cyclopropyl}-2-hydroxy-2-trifluoromethylpropionylamino]-4-methyl-2,3-benzoxazin-1-one 6-[2-hydroxy-4-methyl-4-(3-methyl-2-nitrophenyl)-2-trifluoromethylvaleroylamino]-4-methyl-2,3-benzoxazin-1-one (−) 6-[2-hydroxy-4-methyl-4-(3-methyl-2-nitrophenyl)-2-trifluoromethylvaleroylamino]-4-methyl-2,3-benzoxazin-1-one (+) 6-[2-hydroxy-4-methyl-4-(3-methyl-2-nitrophenyl)-2-trifluoromethylvaleroylamino]-4-methyl-2,3-benzoxazin-1-one 5-[4-(2-amino-5-fluorophenyl)-2-hydroxy-4-methyl-2-trifluoromethylvaleroyl-amino]phthalide (−) 5-[4-(2-amino-5-fluorobenyl)-2-hydroxy-4-methyl-2-trifluoromethylvaleroyl-amino]-phthalide (+) 5-[4-(2-amino-5-fluorophenyl)-2-hydroxy-4-methyl-2-trifluoromethylvaleroyl-amino]-phthalide 6-[4-(2-amino-5-fluorophenyl)-2-hydroxy-4-methyl-2-trifluoromethylvaleroyl-amino]-4-methyl-2,3-benzoxazin-1-one (−) 6-[4-(2-amino-5-fluorophenyl)-2-hydroxy-4-methyl-2-trifluoromethylvaleroyl-amino]-4-methyl-2,3-benzoxazin-1-one (+) 6-[4-(2-amino-5-fluorophenyl)-2-hydroxy-4-methyl-2-trifluoromethylvaleroylamino]-4-methyl-2,3-benzoxazin-1-one 6-[4-(2-acetylamino-5-fluorophenyl)-2-hydroxy-4-methyl-2-trifluoromethyl-valeroylamino]-4-methyl-2,3-benzoxazin-1-one (−) 6-[4-(2-acetylamino-5-fluorophenyl)-2-hydroxy-4-methyl-2-trifluoromethyl-valeroylamino]-4-metbyl-2,3-benzoxazin-1-one (+) 6-[4-(2-acetylamino-5-fluorophenyl)-2-hydroxy-4-methyl-2-trifluoromethyl-valeroylamino]-4-methyl-2,3-benzoxazin-1-one 5-[4-(2-acetylamino-5-fluorophenyl)-2-hydroxy-4-methyl-2-trifluoromethyl-valeroylamino]-phthalide (−) 5-[4-(2-acetylamino-5-fluorophenyl)-2-hydroxy-4-methyl-2-trifluoromethyl-valeroylamino]-phthalide (+) 5-[4-(2-acetylamino-5-fluorophenyl)-2-hydroxy-4-methyl-2-trifluoromethyl-valeroylamino]-phthalide 5-[4-(5-fluoro-2-mesylaminophenyl)-2-hydroxy-4-methyl-2-trifluoromethyl-valeroylamino]-phthalide (−) 5-[4-(5-fluoro-2-mesylaminophenyl)-2-hydroxy-4-methyl-2-trifluoromethyl-valeroylamino]-phthalide (+) 5-[4-(5-fluoro-2-mesylaminophenyl)-2-hydroxy-4-methyl-2-trifluoromethyl-valeroylamino]-phthalide 6-[4-(2-bromo-3-methoxyphenyl)-2-hydroxy-4-methyl-2-trifluoromethyl-valeroylamino]-4-methyl-2,3-benzoxazin-1-one (−) 6-[4-(2-bromo-3-methoxyphenyl)-2-hydroxy-4-methyl-2-trifluoromethyl-valeroylamino]-4-methyl-2,3-benzoxazin-1-one (+) 6-[4-(2-bromo-3-methoxyphenyl)-2-hydroxy-4-methyl-2-trifluoromethyl-valeroylamino]-4-methyl-2,3-benzoxazin-1-one 6-[4-(2-bromo-3-hydroxyphenyl)-2-hydroxy-4-methyl-2-trifluoromethyl-valeroylamino]-4-methyl-2,3-benzoxazin-1-one (−) 6-[4-(2-bromo-3-hydroxyphenyl)-2-hydroxy-4-methyl-2-trifluoromethyl-valeroylamino]-4-methyl-2,3-benzoxazin-1-one (+) 6-[4-(2-bromo-3-hydroxyphenyl)-2-hydroxy-4-methyl-2-trifluoromethyl-valeroylamino]-4-methyl-2,3-benzoxazin-1-one 6-[4-(2-bromo-3-hydroxyphenyl)-2-hydroxy-4-methyl-2-trifluoromethyl-valeroylamino]-4-methyl-2,3-benzoxazin-1-one (−)-6-[4-(2-bromo-3-hydroxyphenyl)-2-hydroxy-4-methyl-2-trifluoromethyl-valeroylamino]-4-methyl-2,3-benzoxazin-1-one (+)-6-[4-(2-bromo-3-hydroxyphenyl)-2-hydroxy-4-methyl-2-trifluoromethyl-valeroylamino]-4-methyl-2,3-benzoxazin-1-one 6-[4-(2,3-difluorophenyl)-2-hydroxy-4-methyl-2-trifluoromethylcaproylamino]-4-methyl-2,3-benzoxazin-1-one (−) 6-[4-(2,3-difluorophenyl)-2-hydroxy-4-methyl-2-trifluoromethylcaproylamino]-4-methyl-2,3-benzoxazin-1-one (+) 6-[4-(2,3-difluorophenyl)-2-hydroxy-4-methyl-2-trifluoromethylcaproylamino]-4-methyl-2,3-benzoxazin-1-one 6-[4-(2,6-difluorophenyl)-2-hydroxy-4-methyl-4-trifluoromethylcaproylamino]-4-methyl-2,3-benzoxazin-1-one (−) 6-[4-(2,6-difluorophenyl)-2-hydroxy-4-methyl-4-trifluoromethylcaproylamino]-4-methyl-2,3-benzoxazin-1-one (+) 6-[4-(2,6-difluorophenyl)-2-hydroxy-4-methyl-4-trifluoromethylcaproylamino]-4-methyl-2,3-benzoxazin-1-one 6-{3-[4-(2-chloro-5-fluorophenyl)-tetrahydropyran-4-yl]-2-hydroxy-2-trifluoromethylpropionylamino}-4-methyl-2,3-benzoxazin-1-one (−) 6-{3-[4-(2-chloro-5-fluorophenyl)-tetrahydropyran-4-yl]-2-hydroxy-2-trifluoromethylpropionylamino}-4-methyl-2,3-benzoxazin-1-one (+) 6-{3-[4-(2-chloro-5-fluorophenyl)-tetrahydropyran-4-yl]-2-hydroxy-2-trifluoromethyipropionylamino}-4-methyl-2,3-benzoxazin-1-one or physiologically compatible salts thereof.

4. A method according to claim 2, wherein said compound is

6-[4-(5-Fluoro-2-methylphenyl)-2-hydroxy-4-methyl-2-trifluoromethylvaleroylamino]-4-methyl-2,3-benzoxazin-1-one 5-[4-(5-fluoro-2-methylphenyl)-2-hydroxy-4-methyl-2-trifluoromethylvaleroylamino]-phthalide 6-[4-(2-chloro-5-fluorophenyl)-2-hydroxy-4-methyl-2-trifluoromethylvaleroylamino]-4-methyl-2,3-benzoxazin-1-one 5-[4-(5-fluoro-2-nitrophenyl)-2-hydroxy-4-methyl-2-trifluoromethylvaleroylamino]-phthalide 6-[4-(5-fluoro-2-nitrophenyl)-2-hydroxy-4-methyl-2-trifluoromethylvaleroylamino]-4-methyl-2,3-benzoxazin-1-one 5-[4-(3-fluoro-4-nitrophenyl)-2-hydroxy-4-methyl-2-trifluoromethylvaleroylamino]-phthalide 6-[4-(3-fluoro-4-nitrophenyl)-2-hydroxy-4-methyl-2trifluoromethylvaleroylamino]-4-methyl-2,3-benzoxazin-1-one 6-[4-(2-bromo-5-fluorophenyl)-2-hydroxy-4-methyl-2-trifluoromethylvaleroylamino]-4-methyl-2,3-benzoxazin-1-one 6-[4-(indan-4'-yl)-2-hydroxy-4-methyl-2-trifluoromethylvaleroylamino]-4-methyl-2,3-benzoxazin-1-one (−) 6-[4-(indan-4'-yl)-2-hydroxy-4-methyl-2-trifluoromethylvaleroylamino]-4-methyl-2,3-benzoxazin-1-one (+) 6-(4-(indan-4'-yl)-2-hydroxy-4-melhyl-2-trifluoromethylvaleroylamino]-4-methyl-2,3-benzoxazin-1-one 6-[4-(5-fluoro-2-vinylphenyl)-2-hydroxy-4-methyl-2-trifluoromethylvaleroylamino]-4-methyl-2,3-benzoxazin-1-one (−) 6-[4-(5-fluoro-2-vinylphenyl)-2-hydroxy-4-methyl-2-trifluoromethylvaleroylamino]-4-methyl-2,3-benzoxazin-1-one (+) 6-[4-(5-fluoro-2-vinylphenyl)-2-hydroxy-4-methyl-2-trifluoromethylvaleroylamino]-4-methyl-2,3-benzoxazin-1-one 6-[2-hydroxy-4-methyl-2-trifluoromethyl-4-(4-trifluoromethylphenyl)-valeroylamino]-4-methyl-2,3-benzoxazin-1-one (−) 6-[2-hydroxy-4-methyl-2-trifluoromethyl-4-(4-trifluoromethylphenyl)-valeroylamino]-4-methyl-2,3-benzoxazin-1-one (+) 6-[2-hydroxy-4-methyl-2-trifluoromethyl-4-(4-trifluoromethylphenyl)-valeroylamino]-4-methyl-2,3-benzoxazin-1-one 6-[4-(2-bromo-3,5-difluorophenyl)-2-hydroxy-4-methyl-2-trifluoromethylvaleroylamino]-4-methyl-2,3-benzoxazin-1-one (−) 6-[4-(2-bromo-3,5-difluorophenyl)-2-hydroxy-4-methyl-2-trifluoromethylvaleroylamino]-4-methyl-2,3-benzoxazin-1-one (+) 6-[4-(2-bromo-3,5-difluorophenyl)-2-hydroxy-4-methyl-2-trifluoromethylvaleroylamino]-4-methyl-2,3-benzoxazin-1-one 6-[4-(3,5-difluorophenyl)-2-hydroxy-4-methyl-2-trifluoromethylvaleroylamino]-4-methyl-2,3-benzoxazin-1-one (−) 6-[4-(3,5-difluorophenyl)-2-hydroxy-4-methyl-2-trifluoromethylvaleroylamino]-4-methyl-2,3-benzoxazin-1-one (+) 6-[4-(3,5-difluorophenyl)-2-hydroxy-4-methyl-2-trifluoromethylvaleroylamino]-4-methyl-2,3-benzoxazin-1-one 6-[4-(2-cyano-5-fluorophenyl)-2-hydroxy-4-methyl-2-trifluoromethylvaleroylamino]-4-methyl-2,3-benzoxazin-1-one 6-[4-(2-ethenyl-5-fluorophenyl)-2-hydroxy-4-methyl-2-trifluoromethylvaleroylamino]-4-methyl-2,3-benzoxazin-1-one 6-[4-(2-ethyl-5-fluorophenyl)-2-hydroxy-4-methyl-2-trifluoromethylvaleroylamino]-4-methyl-2,3-benzoxazin-1-one 6-[4-(5-fluoro-2-phenylphenyl)-2-hydroxy-4-methyl-2-trifluoromethylvaleroylamino]-4-methyl-2,3-benzoxazin-1-one 6-[4-{5-fluoro-2-(furan-2'-yl)phenyl}-2-hydroxy-4-methyl-2-trifluoromethylvaleroylamino]-4-methyl-2,3-benzoxazin-1-one 6-[4-(2-bromo-3,5-difluorophenyl)-2-hydroxy-4-methyl-2-trifluoromethylvaleroylamino]-4-methyl-2,3-benzoxazin-1-one 6-[2-hydroxy-4-methyl-2-trifluoromethyl-4-(1-naphthyl)-valeroylamino]-4-methyl-2,3-benzoxazin-1-one (−) 6-[2-hydroxy-4-methyl-2-trifluoromethyl-4-(1-naphthyl)-valeroylamino]-4-metbyl-2,3-benzoxazin-1-one (+) 6-[2-hydroxy-4-methyl-2-trifluoromethyl-4-(1-naphthyl)-valeroylarnino]-4-methyl-2,3-benzoxazin-1-one 6-[4-(2-chlorophenyl)-2-hydroxy-4-methyl-2-trifluoromethylvaleroyl]-amino-4-methyl-2,3-benzoxazin-1-one (−)-6-[4-(2-chlorophenyl)-2-hydroxy-4-methyl-2-trifluoromethylvaleroyl]-amino-4-methyl -2,3-benzoxazin-1-one (+)-6-[4-(2-chlorophenyl)-2-hydroxy-4-methyl-2-trifluoromethylvaleroyl]-amino-4-methyl-2,3-benzoxazin-1-one 6-[4-(2-chloro-3-fluoro-phenyl)-2-hydroxy-4-methyl-2-trifluoromethylvaleroyl]-amino-4-methyl-2,3-benzoxazin-1-one (−)-6-[4-(2-chloro-3-fluoro-phenyl)-2-hydroxy-4-methyl-2-trifluoromethylvaleroyl]-amino-4-methyl-2,3-benzoxazin-1-one (+)-6-[4-(2-chloro-3-fluoro-phenyl)-2-hydroxy-4-methyl-2-trifluoromethylvaleroyl]-amino-4-methyl-2,3-benzoxazin-1-one 6-[4-(2-chloro-4-fluoro-phenyl)-2-hydroxy-4-methyl-2-trifluoromethylvaleroyl]-amino-4-methyl-2,3-benzoxazin-1-one (−)-6-[4-(2-chloro-4-fluoro-phenyl)-2-hydroxy-4-methyl-2-trifluoromethylvaleroyl]-amino-4-methyl-2,3-benzoxazin-1-one (+)-6-[4-(2-chloro-4-fluoro-phenyl)-2-hydroxy-4-methyl-2-trifluoromethylvaleroyl]-amino-4-methyl-2,3-benzoxazin-1-one 6-[4-(2-chloro-6-fluoro-phenyl)-2-hydroxy-4-methyl-2-trifluoromethylvaleroyl]-amino-4-methyl-2,3-benzoxazin-1-one (−)-6-[4-(2-chloro-6-fluoro-phenyl)-2-hydroxy-4-methyl-2-trifluoromethylvaleroyl]-amino-4-methyl-2,3-benzoxazin-1-one (+)-6-[4-(2-chloro-6-fluoro-phenyl)-2-hydroxy-4-methyl-2-trifluoromethylvaleroyl]-amino-4-methyl-2,3-benzoxazin-1-one 6-[4-(2,3-dichlorophenyl)-2-hydxoxy-4-methyl-2-trifluoromethylvaleroyl]-amino-4-methyl-2,3-benzoxazin-1-one (−)-6-[4-(2,3-dichlorophenyl)-2-hydroxy-4-methyl-2-trifluorometbylvaleroyl]-amino-4-methyl-2,3-benzoxazin-1-one (+)-6-[4-(2,3-dichlorophenyl)-2-hydroxy-4-methyl-2-trifluoromethylvaleroyl]-amino-4-methyl-2,3-benzoxazin-1-one 6-[4-(2,4-dichlorophenyl)-2-hydroxy-4-methyl-2-trifluoromethylvaleroyl]-amino-4-methyl-2,3-benzoxazin-1-one (−)-6-[4-(2,4-dichlorophenyl)-2-hydroxy-4-methyl-2-trifluoromethylvaleroyl]-amino-4-methyl-2,3-benzoxazin-1-one (+)-6-[4-(2,4-dichlorophenyl)-2-hydroxy-4-methyl-2-trifluoromethylvaleroyl]-amino-4-methyl-2,3-benzoxazin-1-one 6-[4-(2,5-dichlorophenyl)-2-hydroxy-4-methyl-2-trifluoromethylvaleroyl]-amino-4-methyl-2,3-benzoxazin-1-one (−)-6-[4-(2,5-dichlorophenyl)-2-hydroxy-4-methyl-2-trifluoromethylvaleroyl]-amino-4-methyl-2,3-benzoxazin-1-one (+)-6-[4-(2,5-dichlorophenyl)-2-hydroxy-4-methyl-2-trifluoromethyl]-amino-4-methyl-2,3-benzoxazin-1-one 6-[4-(4-bromo-2-chlorophenyl)-2-hydroxy-4-methyl-2-trifluoromethylvaleroyl]-amino-4-methyl-2,3-benzoxazin-1-one (−)-6-[4-(4-bromo-2-chlorophenyl)-2-hydroxy-4-methyl-2-trifluoromethylvaleroyl]-amino-4-methyl-2,3-benzoxazin-1-one (+)-6-[4-(4-bromo-2-chlorophenyl)-2-hydroxy-4-methyl-2-trifluoromethylvaleroyl]-amino-4-methyl-2,3-benzoxazin-1-one 6-[4-(2-chloro-3-methoxyphenyl)-2-hydroxy-4-methyl-2-trifluoromethylvaleroyl]-amino-4-methyl-2,3-benzoxazin-1-one (−)-6-[4-(2-chloro-3-methoxyphenyl)-2-hydroxy-4-methyl-2-trifluoromethylvaleroyl]-amino-4-methyl-2,3-benzoxazin-1-one (+)-6-[4-(2-chloro-3-methoxyphenyl)-2-hydroxy-4-methyl-2-trifluoromethylvaleroyl]-amino-4-methyl-2,3-benzoxazin-1-one 6-[4-(2-chloro-3-hydroxyphenyl)-2-hydroxy-4-methyl-2-trifluoromethylvaleroyl]-amino-4-methyl-2,3-benzoxazin-1-one (−)-6-[4-(2-chloro-3-hydroxyphenyl)-2-hydroxy-4-methyl-2-trifluoromethylvaleroyl]-amino-4-methyl-2,3-benzoxazin-1-one (+)-6-[4-(2-chloro-3-hydroxyphenyl)-2-hydroxy-4-methyl-2-trifluoromethylvaleroyl]-amino-4-methyl-2,3-benzoxazin-1-one 6-[4-(2-fluorophenyl)-2-hydroxy-4-methyl-2-trifluoromethylvaleroylamino]-4-methyl-2,3-benzoxazin-1-one (−)-6-[4-(2-fluorophenyl)-2-hydroxy-4-methyl-2-trifluoromethylvaleroylamino]-4-methyl-2,3-benzoxazin-1-one (+)-6-[4-(2-fluorophenyl)-2-hydroxy-4-methyl-2-trifluoromethylvaleroylamino]-4-methyl-2,3-benzoxazin-1-one 6-[4-(2,3-difluorophenyl)-2-hydroxy-4-methyl-2-trifluoromethylvaleroylamino]-4-methyl-2,3-benzoxazin-1-one (−)-6-[4-(2,3-difluorophenyl)-2-hydroxy-4-methyl-2-trifluoromethylvaleroylamino]-4-methyl-2,3-benzoxazin-1-one (+)-6-[4-(2,3-difluorophenyl)-2-hydroxy-4-methyl-2-trifluoromethylvaleroyl]-amino-4-methyl-2,3-benzoxazin-1-one (−)-6-[4-(2,3-difluorophenyl)-2-hydroxy-4-methyl-2-trifluoromethylhexanoylamino]-4-methyl-2,3-benzoxazin-1-one (+)-6-[4-(2,3-difluorophenyl)-2-hydroxy-4-methyl-2-trifluoromethylhexanoylamino]-4-methyl-2,3-benzoxazin-1-one 6-[4-(2,4-difluorophenyl)-2-hydroxy-4-methyl-2-trifluoromethylvaleroylamino]-4-methyl-2,3-benzoxazin-1-one (−)-6-[4-(2,4-difluorophenyl)-2-hydroxy-4-methyl-2-trifluoromethylvaleroylamino]-4-methyl-2,3-benzoxazin-1-one (+)-6-[4-(2,4-difluorophenyl)-2-hydroxy-4-methyl-2-trifluoromethylvaleroylamino]-4-methyl-2,3-benzoxazin-1-one 6-[4-(2,5-difluorophenyl)-2-hydroxy-4-methyl-2-trifluoromethylvaleroylamino]-4-methyl -2,3-benzoxazin-1-one (−)-6-[4-(2,5-difluorophenyl)-2-hydroxy-4-methyl-2-trifluoromethylvaleroylamino]-4-methyl-2,3-benzoxazin-1-one (+)-6-[4-(2,5-difluorophenyl)-2-hydroxy-4-methyl-2-trifluoromethylvaleroylamino]-4-methyl-2,3-benzoxazin-1-one 6-[4-(2,6-difluorophenyl)-2-hydroxy-4-methyl-2-trifluoromethylvaleroylamino]-4-methyl-2,3-benzoxazin-1-one (−)-6-[4-(2,6-difluorophenyl)-2-hydroxy-4-methyl-2-trifluoromethylvaleroylamino]-4-methyl-2,3-benzoxazin-1-one (+)-6-[4-(2,6-difluorophenyl)-2-hydroxy-4-methyl-2-trifluoromethylvaleroylamino]-4-methyl-2,3-benzoxazin-1-one 6-[4-(2,3,5-trifluorophenyl)-2-hydroxy-4-methyl-2-trifluoromethylvaleroylamino]-4-methyl-2,3-benzoxazin-1-one (−)-6-[4-(2,3,5-trifluorophenyl)-2-hydroxy-4-methyl-2-trifluoromethylvaleroylamino]-4-methyl-2,3-benzoxazin-1-one (+)-6-[4-(2,3,5-trifluorophenyl)-2-hydroxy-4-methyl-2-trifluoromethylvaleroylamino]-4-methyl-2,3-benzoxazin-1-one 6-[4-(2,3,4-trifluorophenyl)-2-hydroxy-4-methyl-2-trifluoromethylvaleroylamino]-4-methyl-2,3-benzoxazin-1-one (−)-6-[4-(2,3,4-trifluorophenyl)-2-hydroxy-4-methyl-2-trifluoromethylvaleroylamino]-4-methyl-2,3-benzoxazin-1-one (+)-6-[4-(2,3,4-trifluorophenyl)-2-hydroxy-4-methyl-2-trifluoromethylvaleroylamino]-4-methyl-2,3-benzoxazin-1-one 6-[4-(3-chloro-2-fluorophenyl)-2-hydroxy-4-methyl-2-trifluoromethylvaleroylamino]-4-methyl-2,3-beazoxazin-1-one (−)-6-[4-(3-chloro-2-fluorophenyl)-2-hydroxy-4-methyl-2-trifluoromethylvaleroyl-amino]-4-methyl-2,3-benzoxazin-1-one (+)-6-[4-(3-chloro-2-fluorophenyl)-2-hydroxy-4-methyl-2-trifluoromethylvaleroylamino]-4-methyl-2,3-benzoxazin-1-one 6-[4-(4-chloro-2-fluorophenyl)-2-hydroxy-4-methyl-2-trifluoromethylvaleroylamino]-4-methyl-2,3-benzoxazin-1-one (−)-6-[4-(4-chloro-2-fluorophenyl)-2-hydroxy-4-methyl-2-trifluoromethylvaleroyl-amino]-4-methyl-2,3-benzoxazin-1-one (+)-6-[4-(4-chloro-2-fluorophenyl)-2-hydroxy-4-methyl-2-trifluoromethylvaleroyl-amino]-4-methyl-2,3-benzoxazin-1-one 6-[4-(2-fluoro-3-methoxyphenyl)-2-hydroxy-4-methyl-2-trifluoromethylvaleroylamino]-4-methyl-2,3-benzoxazin-1-one (−) 6-[4-(2-fluoro-3-methoxyphenyl)-2-hydroxy-4-methyl-2-trifluoromethylvaleroyl-amino]-4-methyl-2,3-benzoxazin-1-one (+) 6-[4-(2-fluoro-3-methoxyphenyl)-2-hydroxy-4-methyl-2-trifluoromethylvaleroylamino]-4-methyl-2,3-benzoxazin-1-one 6-[4-(2-bromophenyl)-2-hydroxy-4-methyl-2-trifluoromethylvaleroylamino]-4-methyl-2,3-benzoxazin-1-one (−)-6-[4-(2-bromophenyl)-2-hydroxy-4-methyl-2-trifluoromethylvaleroylamino]-4-methyl-2,3-benzoxazin-1-one (+)-6-[4-(2-bromophenyl)-2-hydroxy-4-methyl-2-trifluoromethylvaleroylamino]-4-methyl-2,3-benzoxazin-1-one 6-[4-(2-trifluoromethyl-phenyl)-2-hydroxy-4-methyl-2-trifluoromethylvaleroyl]-amino-4-methyl-2,3-benzoxazin-1-one (−)-6-[4-(2-trifluoromethyl-phenyl)-2-hydroxy-4-methyl-2-trifluorometbylvaleroyl]-amino-4-methyl-2,3-benzoxazin-1-one (+)-6-[4-(2-trifluoromethyl-phenyl)-2-hydroxy-4-methyl-2-trifluoromethylvaleroyl]-amino-4-methyl-2,3-benzoxazin-1-one 6-[4-(4-fluoro-2-trifluoromethyl-phenyl)-2-hydroxy-4-methyl-2-trifluoromethyl-valeroyl]-amino-4-methyl-2,3-benzoxazin-1-one (−)-6-[4-(4-fluoro-2-trifluoromethyl-phenyl)-2-hydroxy-4-methyl-2trifluoromethyl-valeroyl]-amino-4-methyl-2,3-benzoxazin-1-one (+)-6-[4-(4-fluoro-2-trifluoromethyl-phenyl)-2-hydroxy-4-methyl-2-trifluoromethyl-valeroyl]-amino-4-methyl-2,3-benzoxazin-1-one 6-[4-(5-fluoro-2-trifluoromethyl-phenyl)-2-hydroxy-4-methyl-2-trifluoromethyl-valeroyl]-amino-4-methyl-2,3-benzoxazin-1-one (−)-6-[4-(5-fluoro-2-trifluoromethyl-pbenyl)-2-hydroxy-4-methyl-2-trifluoromethyl-valeroyl]-amino-4-methyl-2,3-benzoxazin-1-one (+)-6-[4-(5-fluoro-2-trifluoromethyl-phenyl)-2-hydroxy-4-methyl-2-trifluoromethyl-valeroyl]-amino-4-methyl-2,3-benzoxazin-1-one 6-[4-(5-chloro-2-trifluoromethyl-phenyl)-2-hydroxy-4-methyl-2-trifluoromethyl-valeroyl]-amino-4-methyl-2,3-benzoxazin-1-one (−)-6-[4-(5-chloro-2-trifluoromethyl-phenyl)-2-hydroxy-4-methyl-2-trifluoromethyl-valeroyl]-amino-4-methyl-2,3-benzoxazin-1-one (+)-6-[4-(5-chloro-2-trifluoromethyl-phenyl)-2-hydroxy-4-methyl-2-trifluoromethyl-valeroyl]-amino-4-methyl-2,3-benzoxazin-1-one 6-[3-{1-(2-chlorophenyl)-cyclopropyl}-2-hydroxy-2-trifluoromethylpropionyl]-amino-4-methyl-2,3-benzoxazin-1-one (−) 6-[3-{1-(2-chlorophenyl)-cyclopropyl}-2-hydroxy-2-trifluoromethylpropionyl]-amino-4-methyl-2,3-benzoxazin-1-one (+) 6-[3-{1-(2-chlorophenyl)-cyclopropyl}-2-hydroxy-2-trifluoromethylpropionyl]-amino-4-methyl-2,3-benzoxazin-1-one 6-[3-{1-(2-chlorophenyl)-cyclobutyl}-2-hydroxy-2-trifluoromethylpropionyl]-amino-4-methyl-2,3-benzoxazin-1-one (−)-6-[3-{1-(2-chlorophenyl)-cyclobutyl}-2-hydroxy-2-trifluoromethylpropionyl]-amino-4-methyl-2,3-benzoxazin-1-one (+)-6-[3-{1-(2-chlorophenyl)-cyclobutyl}-2-hydroxy-2-trifluoromethylpropionyl]-amino-4-methyl-2,3-benzoxazin-1-one 6-[3-{1-(2-chlorophenyl)-cyclopentyl}-2-hydroxy-2-trifluorometbylpropionyl]-amino-4-methyl-2,3-benzoxazin-1-one (−)-6-[3-{1-(2-chlorophenyl)-cyclopentyl}-2-hydroxy-2-trifluoromethylpropionyl]-amino-4-methyl-2,3-benzoxazin-1-one (+)-6-[3-{1-(2-chlorophenyl)-cyclopentyl}-2-hydroxy-2-trifluoromethylpropionyl]-amino-4-methyl-2,3-benzoxazin-1-one 6-[3-{1-(2-chloro-4-fluorophenyl)-cyclopropyl}-2-hydroxy-2-trifluoromethylpropionyl]-amino-4-methyl-2,3-benzoxazin-1-one (−)-6-[3-{1-(2-chloro-4-fluorophenyl)-cyclopropyl}-2-hydroxy-2-trifluoromethyl-propionyl]-amino-4-methyl-2,3-benzoxazin-1-one (+)-6-[3-{1-(2-chloro-4-fluorophenyl)-cyclopropyl}-2-hydroxy-2-trifluoromethyl-propionyl]-amino-4-methyl-2,3-benzoxazin-1-one 6-[3-{1-(2-chloro-4-fluorophenyl)-cyclobutyl}-2-hydroxy-2-trifluoromethylpropionyl]-amino-4-methyl-2,3-benzoxazin-1-one (−)-6-[3-{1-(2-chloro-4-fluorophenyl)-cyclobutyl}-2-hydroxy-2-trifluoromethyl-propionyl]-amino-4-methyl-2,3-benzoxazin-1-one (+)-6-[3-{1-(2-chloro-4-fluorophenyl)-cyclobutyl}-2-hydroxy-2-trifluoromethyl-propionyl]-amino-4-methyl-2,3-benzoxazin-1-one 6-[3-{1-(2-chloro-5-fluorophenyl)-cyclopropyl}-2-hydroxy-2-trifluoromethylpropionyl]-amino-4-methyl-2,3-benzoxazin-1-one (−)-6-[3-{1-(2-chloro-5-fluorophenyl)-cyclopropyl}-2-hydroxy-2-trifluoromethylpropionyl]-amino-4-methyl-2,3-benzoxazin-1-one (+)-6-[3-{1-(2-chloro-5-fluorophenyl)-cyclopropyl}-2-hydroxy-2-trifluoromethyl-propionyl]-amino-4-methyl-2,3-benzoxazin-1-one 6-[3-{1-(2-chloro-5-fluorophenyl)-cyclobutyl}-2-hydroxy-2-trifluoromethylpropionyl]-amino-4-methyl-2,3-benzoxazin-1-one (−)-6-[3-{1-(2-chloro-5-fluorophenyl)-cyclobutyl}-2-hydroxy-2-trifluoromethyl-propionyl]-amino-4-methyl-2,3-benzoxazin-1-one (+)-6-[3-{1-(2-chloro-5-fluorophenyl)-cyclobutyl}-2-hydroxy-2-trifluoromethyl-propionyl]-amino-4-methyl-2,3-benzoxazin-1-one 6-[3-{1(2,4-dichlorophenyl)-cyclopropyl}-2-hydroxy-2-trifluoromethylpropionyl]-amino-4-methyl-2,3-benzoxazin-1-one (−)-6-[3-{1-(2,4-dichlorophenyl)-cyclopropyl}-2-hydroxy-2-trifluoromethylpropionyl]-amino-4-methyl-2,3-benzoxazin-1-one (+)-6-[3-{1-(2,4-dichlorophenyl)-cyclopropyl}-2-hydroxy-2-trifluoromethylpropionyl]-amino-4-methyl-2,3-benzoxazin-1-one 6-[3-{1-(2,4-dichlorophenyl)-cyclobutyl}-2-hydroxy-2-trifluoromethylpropionyl]-amino-4-methyl-2,3-benzoxazin-1-one (−)-6-[3-{1-(2,4-dichlorophenyl)-cyclobutyl}-2-hydroxy-2-trifluoromethylpropionyl]-amino-4-methyl-2,3-benzoxazin-1-one (+)-6-[3-{1-(2,4-dichlorophenyl)-cyclobutyl}-2-hydroxy-2-trifluoromethylpropionyl]-amino-4-methyl-2,3-benzoxazin-1-one 6-[3-{1-(2-trifluoromethyl-phenyl)-cyclopropyl}-2-hydroxy-2-trifluoromethylpropionyl]-amino-4-methyl-2,3-benzoxazin-1-one (−)-6-[3-{1-(2-trifluoromethyl-phenyl)-cyclopropyl}-2-hydroxy-2-trifluoromethylpropionyl]-amino-4-methyl-2,3-benzoxazin-1-one (+)-6-[3-{1-(2-trifluoromethyl-phenyl)-cyclopropyl}-2-hydroxy-2-trifluoromethylpropionyl]-amino-4-methyl-2,3-benzoxazin-1-one 6-[3-{1-(2-trifluoromethyl-phenyl)-cyclobutyl}-2-hydroxy-2-trifluoromethylpropionyl]-amino-4-methyl-2,3-benzoxazin-1-one (−)-6-[3-{1-(2-trifluoromethyl-phenyl)-cyclobutyl}-2-hydroxy-2-trifluoromethylpropionyl]-amino-4-methyl-2,3-benzoxazin-1-one (+)-6-[3-{1-(2-trifluoromethyl-phenyl)-cyclobutyl}-2-hydroxy-2-trifluoromethylpropionyl]-amino-4-methyl-2,3-benzoxazin-1-one 6-[3-{1-(2-trifluoromethyl-phenyl)-cyclohexyl}-2-hydroxy-2-trifluoromethylpropionyl]-amino-4-methyl-2,3-benzoxazin-1-one (−) 6-[3-{1-(2-trifluoromethyl-phenyl)-cyclohexyl}-2-hydroxy-2-trifluoromethylpropionyl]-amino-4-methyl-2,3-benzoxazin-1-one (+) 6-[3-{1-(2-trifluoromethyl-phenyl)-cyclohexyl}-2-hydroxy-2-trifluoromethylpropionyl]-amino-4-methyl-2,3-benzoxazin-1-one 6-[3-{1-(5-fluoro-2-trifluoromethyl-phenyl)-cyclopropyl}-2-hydroxy-2-trifluoromethylpropionyl]-amino-4-methyl-2,3-benzoxazin-1-one (−)-6-[3-{1-(5-fluoro-2-trifluoromethyl-phenyl)-cyclopropyl}-2-hydroxy-2-trifluoromethylpropionyl]-amino-4-methyl-2,3-benzoxazin-1-one (+)-6-[3-{1-(5-fluoro-2-trifluoromethyl-phenyl)-cyclopropyl}-2-hydroxy-2-trifluromethylpropionyl]-amino-4-methyl-2,3-benzoxazin-1-one 6-[3-{1-(5-fluoro-2-trifluoromethyl-phenyl)-cyclobutyl}-2-hydroxy-2-trifluoromethylpropionyl]-amino-4-methyl-2,3-benzoxazin-1-one (−)-6-[3-{1-(5-fluoro-2-trifluoromethyl-phenyl)-cyclobutyl}-2-hydroxy-2-trifluoromethylpropionyl]-amino-4-methyl-2,3-benzoxazin-1-one (+)-6-[3-{1-(5-fluoro-2-trifluoromethyl-phenyl)-cyclobutyl}-2-hydroxy-2-trifluoromethylpropionyl]-amino4-methyl-2,3-benzoxazin-1-one 6-[3-{1-(2-fluorophenyl)-cyclopropyl}-2-hydroxy-2-trifluoromethylpropionylamino]-4-methyl-2,3-benzoxazin-1-one (−)-6-[3-{1-(2-fluorophenyl)-cyclopropyl}-2-hydroxy-2-trifluoromethylpropionylamino]-4-methyl-2,3-benzoxazin-1-one (+)-6-[3-{1-(2-fluorophenyl)-cyclopropyl}-2-hydroxy-2-trifluoromethylpropionylamino]-4-methyl-2,3-benzoxazin-1-one 6-[3-{1-(2-fluorophenyl)-cyclobutyl}-2-hydroxy-2-trifluoromethylpropionylamino]-4-methyl-2,3-benzoxazin-1-one (−)-6-[3-{1-(2-fluorophenyl)-cyclobutyl}-2-hydroxy-2-trifluoromethylpropionylamino]-4-methyl-2,3-benzoxazin-1-one (+)-6-[3-{1-(2-fluorophenyl)-cyclobutyl}-2-hydroxy-2-trifluoromethylpropionylamino]-4-methyl-2,3-benzoxazin-1-one 6-[3-{1-(2-fluorophenyl)-cyclopentyl}-2-hydroxy-2-trifluoromethylpropionylamino]-4-methyl-2,3-benzoxazin-1-one (−)-6-[3-{1-(2-fluorophenyl)-cyclopentyl}-2-hydroxy-2-trifluoromethylpropionylamino]-4-methyl-2,3-benzoxazin-1-one (+)-6-[3-{1-(2-fluorophenyl)-cyclopentyl}-2-hydroxy-2-trifluoromethylpropionylamino]-4-methyl-2,3-benzoxazin-1-one 6-[3-{1-(2-fluorophenyl)-cyclohexyl}-2-hydroxy-2-trifluoromethylpropionylamino]-4-methyl-2,3-benzoxazin-1-one (−)-6-[3-{1-(2-fluorophenyl)-cyclohexyl}-2-hydroxy-2-trifluoromethylpropionylamino]-4-methyl-2,3-benzoxazin-1-one (+)-6-[3-{1-(2-fluorophenyl)-cyclohexyl}-2-hydroxy-2-trifluorormethylpropionylamino]-4-methyl-2,3-benzoxazin-1-one 6-[3-{1-(2,3-difluorophenyl)-cyclopropyl}-2-hydroxy-2-trifluoromethylpropionylamino]-4-methyl-2,3-benzoxazin-1-one (−)-6-[3-{1-(2,3-difluorophenyl)-cyclopropyl}-2-hydroxy-2-trifluoromethylpropionylamino]-4-methyl-2,3-benzoxazin-1-one (+)-6-[3-{1-(2,3-difluorophenyl)-cyclopropyl}-2-hydroxy-2-trifluoromethylpropionyl-amino]-4-methyl-2,3-benzoxazin-1-one 6-[3-{1-(2,3-difluorophenyl)-cyclobutyl}-2-hydroxy-2-trifluoromethylpropionylamino]-4-methyl-2,3-benzoxazin-1-one (−) 6-[3-{1-(2,3-difluorophenyl)-cyclobutyl}-2-hydroxy-2-trifluoromethylpropionylamino]-4-methyl-2,3-benzoxazin-1-one (+) 6-[3-{1-(2,3-difluorophenyl)-cyclobutyl}-2-hydroxy-2-trifluoromethylpropionylamino]-4-methyl-2,3-benzoxazin-1-one 6-[3-{1-(2,5-difluorophenyl)-cyclopropyl}-2-hydroxy-2-trifluoromethylpropionylamino]-4-methyl-2,3-benzoxazin-1-one (−)-6-[3-{1-(2,5-difluorophenyl)-cyclopropyl}-2-hydroxy-2-trifluoromethylpropionylamino]-4methyl-2,3-benzoxazin-1-one (+)-6-[3-{1-(2,5-difluorophenyl)-cyclopropyl}-2-hydroxy-2-trifluoromethylpropionylamino]-4-methyl-2,3-benzoxazin-1-one 6-[3-{1-(2,3,5-trifluorophenyl)-cyclopropyl}-2-hydroxy-2-trifluoromethylpropionylamino]-4-methyl-2,3-benzoxazin-1-one (−)-6-[3-{1-(2,3,5-trifluorophenyl)-cyclopropyl}-2-hydroxy-2-trifluoromethylpropionylamino]-4-methyl-2,3-benzoxazin-1-one (+)-6-[3-{1-(2,3,5-trifluorophenyl)-cyclopropyl}-2-hydroxy-2-trifluoromethylpropionyl-amino]-4-methyl-2,3-benzoxazin-1-one 6-[3-{1-(2,3,5-trifluorophenyl)-cyclobutyl}-2-hydroxy-2-trifluoromethylpropionylamino]-4-methyl-2,3-benzoxazin-1-one (−)-6-[3-{1-(2,3 ,5-trifluorophenyl)-cyclobutyl}-2-hydroxy-2-trifluoromethylpropionylamino]-4-methyl-2,3-benzoxazin-1-one (+)-6-[3-{1-(2,3 ,5-trifluorophenyl)-cyclobutyl}-2-hydroxy-2-trifluoromethylpropionyl-amino]-4-methyl-2,3-benzoxazin-1-one 6-[3-{1-(2-bromopbenyl)-cyclopropyl}-2-hydroxy-2-trifluoromethylpropionylamino]-4-methyl-2,3-benzoxazin-1-one (−)-6-[3-{1-(2-bromophenyl)-cyclopropyl}-2-hydroxy-2-trifluoromethylpropionylamino]-4-methyl-2,3-benzoxazin-1-one (+)-6-[3-{1-(2-bromophenyl)-cyclopropyl}-2-hydroxy-2-trifluoromethylpropionylamino]-4-methyl-2,3-benzoxazin-1-one 6-[2-hydroxy-4-methyl-4-(3-methyl-2-nitrophenyl)-2-trifluoromethylvaleroylamino]-4-methyl-2,3-benzoxazin-1-one (−) 6-[2-hydroxy-4-methyl-4-(3-methyl-2-nitrophenyl)-2-trifluoromethylvaleroylamino]-4-methyl-2,3-benzoxazin-1-one (+) 6-[2-hydroxy-4-methyl-4-(3-methyl-2-nitrophenyl)-2-trifluoromethylvaleroylamino]-4-methyl-2,3-benzoxazin-1-one 5-[4-(2-amino-5-fluorophenyl)-2-hydroxy-4-methyl-2-trifluoromethylvaleroyl-amino]-phthalide (−) 5-[4-(2-amino-5-fluorophenyl)-2-hydroxy-4-methyl-2-trifluoromethylvaleroyl-amino]-phthalide (+) 5-[4-(2-amino-5-fluorophenyl)-2-hydroxy-4-methyl-2-trifluoromethylvaleroyl-amino]-phthalide 6-[4-(2-amino-5-fluorophenyl)-2-hydroxy-4-methyl-2-trifluoromethylvaleroyl-amino-]-4-methyl-2,3-benzoxazin-1-one (−) 6-[4-(2-amino-5-fluorophenyl)-2-hydroxy-4-methyl-2-trifluoromethylvaleroyl-amino-]-4-methyl-2,3-benzoxazin-1-one (+) 6-[4-(2-amino-5-fluorophenyl)-2-hydroxy-4-methyl-2-trifluoromethylvaleroylamino]-4-methyl-2,3-benzoxazin-1-one 6-[4-(2-acetylamino-5-fluorophenyl)-2-hydroxy-4-metbyl-2-trifluoromethyl-valeroylamino]-4-methyl-2,3-benzoxazin-1-one (−) 6-[4-(2-acetylamino-5-fluorophenyl)-2-hydroxy-4-methyl-2-trifluoromethyl-valeroylamino]-4-methyl-2,3-benzoxazin-1-one (+) 6-[4-(2-acetylamino-5-fluorophenyl)-2-hydroxy-4-methyl-2-trifluoromethyl-valeroylamino]-4-methyl-2,3-benzoxazin-1-one 5-[4-(2-acetylamino-5-fluorophenyl)-2-hydroxy-4-methyl-2-trifluoromethyl-valeroylamino]-phthalide (−) 5-[4-(2-acetylamino-5-fluorophenyl)-2-hydroxy-4-methyl-2-trifluoromethyl-valeroylamino]-phthalide (+) 5-[4-(2-acetylamino-5-fluorophenyl)-2-hydroxy-4-methyl-2-trifluoromethyl-valeroylamino]-phthalide 5-[4-(5-fluoro-2-mesylaminopheny)-2-hydroxy-4-methyl-2-trifluoromethyl-valeroylamino]-phthalide (−) 5-[4-(5-fluoro-2-mesylaminophenyl)-2-hydroxy-4-methyl-2-trifluoromethyl-valeroylamino]-phthalide (+) 5-[4-(5-fluoro-2-mesylaminophenyl)-2-hydroxy-4-methyl-2-trifluoromethul-valeroylamino]-phthalide 6-[4-(2-bromo-3-methoxyphenyl)-2-hydroxy-4-methyl-2-trifluoromethyl-valeroylamino]-4-methyl-2,3-benzoxazin-1one (−) 6-[4-(2-bromo-3-methoxyphenyl)-2-hydroxy-4-methyl-2-trifluoromethyl-valeroylamino]-4-methyl-2,3-benzoxazin-1-one (+) 6-[4-(2-bromo-3-methoxyphenyl)-2-hydroxy-4-methyl-2-trifluoromethyl-valeroylamino]-4-methyl-2,3-benzoxazin-1-one 6-[4-(2-bromo-3-hydroxyphenyl)-2-hydroxy-4-methyl-2-trifluoromethyl-valeroylamino]-4-methyl-2,3-benzoxazin-1-one (−) 6-[4-(2-bromo-3-hydroxyphenyl)-2-hydroxy-4-methyl-2-trifluoromethyl-valeroylamino]-4-methyl-2,3-benzoxazin-1-one (+) 6-[4-(2-bromo-3-hydroxyphenyl)-2-hydroxy-4-methyl-2-trifluoromethyl-valeroylamino]-4-methyl-2,3-benzoxazin-1-one 6-[4-(2-bromo-3-hydroxyphenyl)-2-hydroxy-4-methyl-2-trifluoromethyl-valeroylamino]-4-methyl-2,3-benzoxazin-1-one (−)-6-[4-(2-bromo-3-hydroxyphenyl)-2-hydroxy-4-methyl-2-trifluoromethyl-valeroylamino]-4-methyl-2,3-benzoxazin-1-one (+)-6-[4-(2-bromo-3-hydroxyphenyl)-2-hydroxy-4-methyl-2-trifluoromethyl-valeroylamino]-4-methyl-2,3-benzoxazin-1-one 6-[4-(2,3-difluorophenyl)-2-hydroxy-4-methyl-2-trifluoromethylcaproylamino]-4-methyl-2,3-benzoxazin-1-one (−) 6-[4-(2,3-difluorophenyl)-2-hydroxy-4-methyl-2-trifluoromethylcaproylamino]-4-methyl-2,3-benzoxazin-1-one (+) 6-[4-(2,3-difluorophenyl)-2-hydroxy-4-methyl-2-trifluoromethylcaproylamino]-4-methyl-2,3-benzoxazin-1-one 6-[4-(2,6-difluorophenyl)-2-hydroxy-4-methyl-4-trifluoromethylcaproylamino]-4-methyl-2,3-benzoxazin-1-one (−) 6-[4-(2,6-difluorophenyl)-2-hydroxy-4-methyl-4-trifluoromethylcaproylamino]-4-methyl-2,3-benzoxazin-1-one (+) 6-[4-(2,6-difluorophenyl)-2-hydroxy-4-methyl-4-trifluoromethylcaproylamino]-4-methyl-2,3-benzoxazin-1-one 6-{3-[4-(2-chloro-5-fluorophenyl)-tetrahydropyran-4-yl]-2-hydroxy-2-trifluoromethylpropionylamino}-4-methyl-2,3-benzoxazin-1-one (−) 6-{3-[4-(2-chloro-5-fluorophenyl)-tetrahydropyran-4-yl]-2-hydroxy-2-trifluoromethylpropionylamino}-4-methyl-2,3-benzoxazin-1-one (+) 6-{3-[4-(2-chloro-5-fluorophenyl)-tetrahydropyran-4-yl]-2-hydroxy-2-trifluoromethylpropionylamino}-4-methyl-2,3-benzoxazin-1-one or physiologically compatible salts thereof.

5. A method according to claim 1, wherein Ar is of partial formula 2, and $Y^4$ is methyl.

6. A method according to claim 1, wherein Ar is of partial formula 2, $Y^4$ is methyl, and $Y^5$, $Y^7$ and $Y^8$ are each hydrogen.

7. A method according to claim 1, wherein said compound is a 2,3-benzoxazin-1-one.

8. A method according to claim 1, Ar is 4-methyl-2,3-Benzoxazin-1-one.

9. A method according to claim 1, wherein $R^4$ is methyl, chloro, nitro, vinyl, bromo, cyano, ethenyl, ethyl, phenyl, furanyl, fluoro, trifluoromethyl, amino, acetylamino, or mesylamino.

10. A method according to claim 1, wherein $R^5$ is H, fluoro, chloro, methoxy, hydroxy, or methyl.

11. A method according to claim 1, wherein $R^5$ is H.

12. A method according to claim 10, wherein $R^5$ is H.

13. A method according to claim 1, wherein $R^6$ is H, nitro, trifluoromethyl, fluoro, chloro, or bromo.

14. A method according to claim 1, wherein $R^6$ is H.

15. A method according to claim 10, wherein $R^6$ is H.

16. A method according to claim 1, wherein $R^7$ is H, fluoro, or chloro.

17. A method according to claim 1, wherein $R^7$ is H.

18. A method according to claim 10, wherein $R^7$ is H.

19. A method according to claim 1, wherein $R^7$ is F.

20. A method according to claim 10, wherein $R^7$ is F.

21. A method according to claim 1, wherein $R^8$ is H or fluoro.

22. A method according to claim 1, wherein $R^8$ is H.

23. A method according to claim 10, wherein $R^8$ is H.

24. A method according to claim 1, wherein $R^6$, $R^7$, and $R^8$ are each H.

25. A method according to claim 1, wherein said compound is administered in an amount of 1 µg to 100,000 µg per kg of body weight.

26. A method according to claim 1, wherein said compound is administered in the form of a composition comprising said compound and a vehicle.

27. A method according to claim 2, wherein Ar is of partial formula 2, and $Y^4$ is methyl.

28. A method according to claim 2, wherein Ar is of partial formula 2, $Y^4$ is methyl, and $Y^5$, $Y^7$ and $Y^8$ are each hydrogen.

29. A method according to claim 2, wherein said compound is a 2,3-Benzoxazin-1-one.

30. A method according to claim 2, wherein said compound is a 4-methyl-2,3-Benzoxazin-1-one.

31. A method according to claim 2, wherein $R^4$ is methyl, chloro, nitro, vinyl, bromo, cyano, ethenyl, ethyl, phenyl, furanyl, fluoro, trifluoromethyl, amino, acetylamino, or mesylamino.

32. A method according to claim 2, wherein $R^5$ is H, fluoro, chloro, methoxy, hydroxy, or methyl.

33. A method according to claim 2, wherein $R^5$ is H.

34. A method according to claim 32, wherein $R^5$ is H.

35. A method according to claim 2, wherein $R^6$ is H, nitro, trifluoromethyl, fluoro, chloro, or bromo.

36. A method according to claim 2, wherein $R^6$ is H.

37. A method according to claim 32, wherein $R^6$ is H.

38. A method according to claim 2, wherein $R^7$ is H, fluoro, or chloro.

39. A method according to claim 2, wherein $R^7$ is H.

40. A method according to claim 32, wherein $R^7$ is H.

41. A method according to claim 2, wherein $R^7$ is F.

42. A method according to claim 32, wherein $R^7$ is F.

43. A method according to claim 2, wherein $R^8$ is H or fluoro.

44. A method according to claim 2, wherein $R^8$ is H.

45. A method according to claim 32, wherein $R^8$ is H.

46. A method according to claim 2, wherein $R^6$, $R^7$, and $R^8$ are each H.

47. A method according to claim 2, wherein said compound is administered in an amount of 1 µg to 100,000 µg per kg of body weight.

48. A method according to claim 2, wherein said compound is administered in the form of a composition comprising said compound and a vehicle.

* * * * *